US006995279B2

(12) United States Patent
Ushioda et al.

(10) Patent No.: US 6,995,279 B2
(45) Date of Patent: Feb. 7, 2006

(54) METALLOCENE COMPOUNDS, PROCESSES FOR THE PRODUCTION OF OLEFIN POLYMERS USING CATALYSTS CONTAINING THE COMPOUNDS, AND OLEFIN POLYMERS PRODUCED BY THE PROCESSES

(75) Inventors: Tsutomu Ushioda, Chiba (JP); Masato Nakano, Chiba (JP); Toshihiro Uwai, Chiba (JP)

(73) Assignees: Chisso Corporation, Osaka (JP); Chisso Petrochemical Corporation, Tokyo (JP)

( * ) Notice: Subject to any disclaimer, the term of this patent is extended or adjusted under 35 U.S.C. 154(b) by 51 days.

(21) Appl. No.: 10/630,666

(22) Filed: Jul. 31, 2003

(65) Prior Publication Data

US 2004/0127731 A1 Jul. 1, 2004

(30) Foreign Application Priority Data

| Aug. 2, 2002 | (JP) | ............................. 2002-225751 |
| Aug. 30, 2002 | (JP) | ............................. 2002-253298 |
| Dec. 12, 2002 | (JP) | ............................. 2002-361082 |
| Mar. 31, 2003 | (JP) | ............................. 2003-093233 |

(51) Int. Cl.
*C07F 17/00* (2006.01)
*B01J 31/00* (2006.01)
*C08F 4/44* (2006.01)

(52) U.S. Cl. ............................. 556/11; 556/12; 556/53; 526/127; 526/160; 526/943; 502/103; 502/117

(58) Field of Classification Search .................. 556/11, 556/12, 53; 526/127, 160, 943; 502/103, 502/117
See application file for complete search history.

(56) References Cited

U.S. PATENT DOCUMENTS

| 5,064,802 | A | 11/1991 | Stevens et al. ............. 502/155 |
| 5,278,264 | A | 1/1994 | Spaleck et al. ............. 526/127 |
| 6,169,051 | B1 | 1/2001 | Mitani et al. ................ 502/103 |
| 6,218,558 | B1 * | 4/2001 | Kato et al. ...................... 556/12 |
| 6,326,493 | B1 | 12/2001 | Mitani et al. ................... 546/4 |
| 6,344,530 | B2 * | 2/2002 | Sugano et al. ............... 526/160 |
| 6,479,646 | B1 | 11/2002 | Nakano et al. ................ 534/10 |
| 6,552,210 | B1 | 4/2003 | Göres et al. ................... 556/53 |
| 2001/0053833 | A1 | 12/2001 | Nakano et al. ............. 526/127 |

FOREIGN PATENT DOCUMENTS

| CA | 2084017 | 5/1993 |
| CA | 2099214 | 12/1993 |
| CA | 2395552 | 6/2002 |
| EP | 0 426 638 | 5/1991 |
| EP | 0 427 695 | 5/1991 |
| EP | 0 427 697 | 5/1991 |
| EP | 0 572 003 | 12/1993 |
| EP | 0 629 632 | 12/1994 |
| EP | 0 775 707 | 5/1997 |
| EP | 0 834 519 | 4/1998 |
| JP | 1-501950 | 7/1989 |
| JP | 1-502036 | 7/1989 |
| JP | 3-179005 | 8/1991 |
| JP | 3-179006 | 8/1991 |
| JP | 3-207704 | 9/1991 |
| JP | 4-309508 | 11/1992 |
| JP | 4-353502 | 12/1992 |
| JP | 5-331232 | 12/1993 |
| JP | 6-100579 | 4/1994 |
| JP | 6-184179 | 7/1994 |
| JP | 7-149833 | 6/1995 |
| JP | 7-188318 | 7/1995 |
| JP | 8-208909 | 8/1996 |
| JP | 8-283343 | 10/1996 |
| JP | 10-087716 | 4/1998 |
| JP | 2002-509936 | 4/2002 |
| JP | 2002-194016 | 7/2002 |
| WO | WO 88/05792 | 8/1988 |
| WO | WO 88/05793 | 8/1988 |
| WO | WO 92/00333 | 1/1992 |
| WO | WO 93/03067 | 2/1993 |
| WO | WO 96/41808 | 12/1996 |
| WO | WO 00/20426 | 4/2000 |
| WO | WO 01/48034 | 7/2001 |

OTHER PUBLICATIONS

T. Sugano, et al., SPO '99, pp. 31, 33-53, "Novel Metallocene Catalyst for Propylene Poylmerization", 1999.
J. A. Bandy, et al., J. Chem. Soc. Dalton Trans., pp. 2207-2216, "Polymerisation of Ethylene and Propene Using New Chiral Zirconium Derivatives. Crystal Structure of $[Zrt.^1Cl_2]—[H_2L^1=(4S,5S)$-*TRANS*$4,5$-BIS(1H-Inden-1-Ylmethyl)-2,2-Dimethyl-1,3-Dioxolane]", 1991.
J. Gräper, et al., Journal of Organometallic Chemistry, vol. 501, pp. 211-218, "Zirconocenophane Dichlorides with Di- and Trisiloxane-Bridged Ring Ligands: Crystal Structure of RAC-[1,1,3,3-Tetramethyldisiloxane-Diyl-BIS(3-Tert-Butyl-r)$^5$-Cyclopentadienyl) Zirconium (IV) Dichloride]", 1995.
H. Plenio, et al., Journal of Organometallic Chemistry, vol. 519, pp. 269-272, "Aminozirconocenes: A New Class of Zirconocenes with a Nitrogen Atom Directly Bonded to an $\eta^5$-Cyclopentadienyl (Indenyl) Ligand", 1996.
H. G. Alt, et al., Journal of Organometallic Chemistry, vol. 564, pp. 109-114, "Synthesis, Characterization and Polymerization Potential of *ANSA*- Metallocene Dichloride Complexes of Titanium, Zirconium and Hafniuim Containing A Si-N-Si Bridging Unit", 1998.

(Continued)

Primary Examiner—Porfirio Nazario-Gonzalez
(74) Attorney, Agent, or Firm—Oblon, Spivak, McClelland, Maier & Neustadt, P.C.

(57) ABSTRACT

Metallocene compounds represented by the following general formula (1):

$$Y_qKLMX_2 \qquad (1)$$

wherein M, Y, q, L and X are each as defined in the Specification.

2 Claims, No Drawings

OTHER PUBLICATIONS

C. J. Schaverien, et al., Journal of Molecular Catalysis A: Chemical, vol. 128, pp. 245-256, "Phosphorus-Bridged Metallocenes: New Homogeneous Catalysts for the Polymerization of Propene", 1998.

K. A. Rufanov, et al., Journal of Organometallic Chemistry, vol. 525, pp. 287-289, "Hetero-ANSA-Metallocenes: I. Synthesis of the Novel [1]-Borylidene-Bridged ANSA-Zirconocene Dichloride", 1996.

A. J. Ashe, III, et al., Organometallics, vol. 18, pp. 2286-2290, "Aminoboranediyl-Bridged Zirconocenes: Highly Active Olefin Polymerization Catalysts", 1999.

K. Rufanov, et al., Journal of Organometallic Chemistry, vol. 536-537, pp. 361-363, "Polyelement Substituted Cyclopentadienes and Indenes—Novel Ligand Precursors for Organotransition Metal Chemistry", 1997.

M. T. Reetz, et al., Chem. Commun., pp. 1105-1106, "Donor Complexes of BIS(1-Indenyl)Phenylborane Dichlorozirconium as Isospecific Catalysts in Propene Polymerization", 1999.

K. A. O. Starzewski, et al., Angew, Chem. Int. Ed., Communications, vol. 38, No. 16, pp. 2439-2443, "Donor/Acceptor Metallocenes: A New Structure Principle in Catalyst Design", 1999.

H. Yamanaka, et al., vol. II, p. 108, "Chemistry of Hetero Ring Compound", 1998 (with partial English translation).

T. Kunieda, et al., vol. 1, No. 1, p. 26, "Chemistry of Hetero Ring", Mar. 25, 2002 (with partial English translation).

M. Boyd, vol. 3, No. 8, pp. 356-359, "Organic Chemistry", 1977 (with partial English translation).

M. Boyd, vol. 3, No. 8, pp. 1231-1232, "Organic Chemistry", 1977 (with partial English translation).

J. A. Ewen, et al., J. Am. Chem. Soc., vol. 123, pp. 4763-4773, "Chiral ANSA Metallocenes with CP Ring-Fused to Thiophenes and Pyrroles: Syntheses, Crystal Structures, and Isotactic Polypropylene Catalysts", 2001.

E. J. M. De Boer, et al., Journal of Molecular Catalysis A: Chemical, vol. 128, pp. 155-165, "Phospholyl Catalysts for Olefin Polymerization", 1998.

J. A. Ewen, et al., J. Am. Chem. Soc., vol. 120, pp. 10786-10787, "Polymerization Catalysts with Cyclopentadienyl Ligands Ring-Fused to Pyrrole and Thiophene Heterocycles", 1998.

C. Janiak, et al., Chem. Ber., vol. 129, pp. 1517-1529, "Ethene Polymerization Activity and Coordination Gap Aperture in Non-ANSA Alkyl-Substituted Cyclopentadienyl-and Phospholyl-Zirconium/Mao Catalysts", 1996.

Macromolecules, Communications to the Editor, vol. 6, No. 6, pp. 925-926, "Carbon-13 Observations of the Stereochemical Configuration of Polypropylene", Nov.-Dec. 1973.

Macromolecules, Communications to the Editor, vol. 8, No. 5, pp. 687-689, "Model Compounds and $^{13}$C NMR Observation of Stereosequences of Polypropylene", Sep.-Oct. 1975.

T. Tsutsui, et al., Polymer, vol. 30, pp. 1350-1356, "Propylene Homo-And Copolymerization with Ethylene Using an Ethylenebis(1-Indenyl) Zirconium Dichloride and Methylaluminoxane Catalyst System", Jul. 1989.

JIS K 7210, pp. 1-16, "Testing Method for Melt Flow rate of Thermoplastics", 1976.

W. Spaleck, et al., Journal of Molecular Catalysis A: Chemical, vol. 128, pp. 279-287, "New Bridged Zirconocenes for Olefin Polymerization: Binuclear and Hybrid Structures", 1998.

* cited by examiner

METALLOCENE COMPOUNDS, PROCESSES FOR THE PRODUCTION OF OLEFIN POLYMERS USING CATALYSTS CONTAINING THE COMPOUNDS, AND OLEFIN POLYMERS PRODUCED BY THE PROCESSES

BACKGROUND OF THE INVENTION

1. Field of the Invention

This invention relates to metallocene compounds, processes for the production of olefin polymers using olefin polymerization catalysts containing the metallocene compounds, and the olefin polymers obtained by the production processes.

2. Related Background Art

In the past there have been reported processes for the production of propylene polymers by using catalysts that contain various metallocene compounds having specifically substituted indenyl ligands (for example, JP-A-06-184179, JP-A-06-100579, JP-A-07-188318, WO 01/48034, JP-A-10-87716, JP-A-08-67689 and WO 97/40075).

Such catalysts containing metallocene compounds are, however, generally costly. For this reason, in order to reduce the production costs of the propylene polymers obtained using such catalysts, further improvement in the polymerizing activity of the catalysts has been desired.

These metallocene compounds have been typically developed with the aim to enabling high molecular weight propylene polymers to be produced as well as to enabling the stereoregularity of the produced propylene polymers to be highly controlled; however, they have not yet come to meeting the desired performance sufficiently.

In addition, it is reported that when a catalyst containing a metallocene compound is used to produce a propylene/ethylene copolymer, the molecular weight of the produced copolymer typically decreases greatly as the content of ethylene unit increases (e.g., T. Sugano, "SPO '99(1999)", pp. 31–53). For this reason, the development of catalysts has been desired such that they contain metallocene compounds and can produce propylene/ethylene copolymers with sufficiently high molecular weight even if their contents of ethylene units are high.

There are also reported the instances where catalysts containing metallocene compounds are used to produce propylene/1-butene copolymers (e.g., see JP-A-08-208909 and JP-A-08-283343). Nevertheless, the development of catalysts has been desired such that they can produce propylene/1-butene copolymers with sufficiently high molecular weight only at practically high polymerization temperatures without causing polymerization at low temperatures.

SUMMARY OF THE INVENTION

One object of this invention is to provide a metallocene compound capable of producing an olefin polymer with high molecular weight and high stereoregularity, a process for the production of an olefin polymer using an olefin polymerization catalyst containing it, and the olefin polymer obtained by the production process.

Another object of this invention is to provide a metallocene compound capable of producing an olefin polymer having high molecular weight and high stereoregularity with high polymerization activity, a process for the production of an olefin polymer using an olefin polymerization catalyst containing it, and the olefin polymer obtained by the production process.

A further object of this invention is to provide a metallocene compound capable of producing a propylene/ethylene copolymer with sufficiently high molecular weight even where the content of ethylene unit is high, a process for the production of an olefin polymer using an olefin polymerization catalyst containing it, and the olefin polymer obtained by the production process.

A still further object of this invention is to provide a metallocene compound capable of producing a propylene/1-butene copolymer with sufficiently high molecular weight even at a practically high polymerization temperature, a process for the production of an olefin polymer using an olefin polymerization catalyst containing it, and the olefin polymer obtained by the production process.

The present inventors discovered that the objects could be achieved by using a metallocene compound having a specific structure in combination with the types of substituents and their positions of substitution, particularly a specific metallocene compound having certain substituents at specified positions, which has led to accomplishing this invention.

Specifically, this invention is shown in [1] to [32] as described below.

[1] A metallocene compound represented by the following general formula (1):

$$Y_q KLMX_2 \qquad (1)$$

wherein

M represents a titanium atom, a zirconium atom or a hafnium atom;

Y represents a linking group bridging K and L and is a methylene group, an ethylene group, a tetraalkylethylene group having alkyl of 1–6 carbon atoms, a dialkylmethylene group having alkyl of 1–6 carbon atoms, a divalent linking group containing within a backbone thereof, an aryl group of 6–16 carbon atoms or a halogenated aryl group of 6–16 carbon atoms, or a divalent linking group containing a silicon atom, a germanium atom, an oxygen atom, a nitrogen atom, a phosphorous atom or a boron atom, or alternatively, Y represents a divalent linking group formed by connecting in series at least two linking groups selected from the foregoing linking groups;

q is an integer representing the number of Y and is 0, 1 or 2;

L represents a ligand having a conjugated 5-membered ring skeleton that is coordinated to M;

K may be the same as or different from L and represents a ligand having a conjugated 5-membered ring skeleton that is coordinated to M, or alternatively, when q is 1, K may be —NH— (N represents a nitrogen atom and H represents a hydrogen atom) or may be —PH— (P represents a phosphorous atom and H represents a hydrogen atom);

at least one of the hydrogen atoms possessed by K and by L is each independently replaced by an alkyl group of 1–10 carbon atoms, a halogen-containing alkyl group of 1–10 carbon atoms, a silicon-containing alkyl group of 1–10 carbon atoms, an aryl group of 6–16 carbon atoms, a halogen-containing aryl group of 6–16 carbon atoms, an alkenyl group of 2–10 carbon atoms, an arylalkyl group of 7–40 carbon atoms, an alkylaryl group of 7–40 carbon atoms, an alicyclic hydrocarbon group of 3–16 carbon atoms, a siloxyl group, an alkoxyl group, a halogen atom, an amino group, a dialkyl-substituted amino group, a heterocyclic group, a SR$^a$ group (S represents a sulfur atom and R$^a$ represents a halogen atom, an alkyl group of 1–10 carbon atoms or an aryl group of 6–16 carbon atoms), or a PR$^b_2$ group (P represents a phosphorous atom, two R may be the same or different and each represents a halogen atom, an alkyl group of 1–10 carbon atoms or an aryl group of 6–16 carbon atoms), with the proviso that when each of K and L represents a ligand having a conjugated 5-membered ring skeleton, at least one substituent having replaced the hydrogen in either of the ligands does not exists at the corresponding position in the other ligand; and two Xs may be the same or different and each represents a halogen atom, an alkyl group of 1–6 carbon atoms, an aryl group of 6–16 carbon atoms, an alkylaryl group having alkyl of 1–6 carbon atoms and aryl of 6–16 carbon atoms or an arylalkyl group having aryl of 6–16 carbon atoms and alkyl of 1–6 carbon atoms, which atom or group is bonded to M, provided that dimethylsilylene(2-methyl-benzoindenyl)(2-methyl-4-(2-furyl)-indenyl)zirconium dichloride and dimethylsilylene(2-methyl-4-phenyl-indenyl)(2-methyl-4-(2-furfuryl)-indenyl)zirconium dichloride are excluded.

[2] The metallocene compound as described in [1] wherein in the general formula (1) according to [1], each of K and L represents a ligand having a conjugated 5-membered ring skeleton; q is 1; and the substituents at the 2-positions of K and L at least differ from each other, the substituents at the 4-positions of K and L at least differ from each other, or both of the substituents at the 2-positions and the substituents of the 4-positions of K and L at least differ respectively between the two ligands.

[3] The metallocene compound as described in [1] wherein in the general formula (1) according to [1], each of K and L represents a ligand having a conjugated 5-membered ring skeleton; q is 1; and the substituents at the 2-positions of K and L at least differ from each other, and at least one of the substituents is an aryl group of 6–16 carbon atoms, a halogen-containing aryl group of 6–16 carbon atoms, an alkylaryl group of 7–40 carbon atoms, an alicyclic hydrocarbon group of 3–16 carbon atoms or a heterocyclic group.

[4] The metallocene compound as described in [1] wherein in the general formula (1) according to [1], each of K and L represents a ligand having a conjugated 5-membered ring skeleton; q is 1; and the substituents at the 2-positions of K and L at least differ from each other, and the difference between the numbers of carbon atoms in the two substituents is in the range of from 3 to 10.

[5] The metallocene compound as described in any one of [1]–[4] wherein in the general formula (1) according to [1], each of K and L represents a ligand having a conjugated 5-membered ring skeleton; q is 1; and the 4-position of at least one ligand in the two ligands K and L is an alkyl group of 1–10 carbon atoms, a halogen-containing alkyl group of 1–10 carbon atoms, a silicon-containing alkyl group of 1–10 carbon atoms, an alkenyl group of 2–10 carbon atoms, an arylalkyl group of 7–40 carbon atoms, an alkylaryl group of 7–40 carbon atoms, a siloxyl group, an alkoxyl group, a halogen atom, an amino group, a dialkyl-substituted amino group, a heterocyclic group, a SR$^a$ group (S represents a sulfur atom and R$^a$ represents a halogen atom, an alkyl group of 1–10 carbon atoms or an aryl group of 6–16 carbon atoms), or a PR$^b_2$ group (P represents a phosphorous atom, two R$^b$ may be the same or different and each represents a halogen atom, an alkyl group of 1–10 carbon atoms or an aryl group of 6–16 carbon atoms).

[6] The metallocene compound as described in [1] wherein in the general formula (1) according to [1], while at least one of the hydrogen atoms possessed by K may be each independently replaced by an alkyl group of 1–6 carbon atoms, a halogen-containing alkyl group of 1–6 carbon atoms, a silicon-containing alkyl group of 1–6 carbon atoms, an aryl group of 6–16 carbon atoms, a halogen-containing aryl group of 6–16 carbon atoms, a 2-furyl group, a substituted 2-furyl group, a 2-thienyl group, a substituted 2-thienyl group, a 2-furfuryl group, a substituted 2-furfuryl group, a siloxyl group or an alkoxyl group, at least one of the hydrogen atoms possessed by K is replaced by a 2-furyl group, a substituted 2-furyl group, a 2-thienyl group, a substituted 2-thienyl group, a 2-furfuryl group or a substituted 2-furfuryl group; at least one of the hydrogen atoms possessed by L may be each independently replaced by an alkyl group of 1–6 carbon atoms, a halogen-containing alkyl group of 1–6 carbon atoms, a silicon-containing alkyl group of 1–6 carbon atoms, an aryl group of 6–16 carbon atoms, a halogen-containing aryl group of 6–16 carbon atoms, a siloxyl group or an alkoxyl group.

[7] The metallocene compound as described in [6] wherein in the general formula (1) according to [1], K and L may be the same or different and each represents a ligand having a conjugated 5-membered ring skeleton; and Y represents is a methylene group, an ethylene group, a tetraalkylethylene group having alkyl of 1–6 carbon atoms, a dialkylmethylene group having alkyl of 1–6 carbon atoms, or a divalent linking group containing a silicon atom, a germanium atom, an oxygen atom, a nitrogen atom, a phosphorous atom or a boron atom.

[8] The metallocene compound as described in [7] wherein in the general formula (1) according to [1], q is 0 or 1.

[9] The metallocene compound as described any one of [1]–[8] wherein in the general formula (1) according to [1], K and L may be the same or different and each represents a cyclopentadienyl group, an indenyl group, a benzoindenyl group, a fluorenyl group, a tetrahydroindenyl group, an azulenyl group, a tetrahydroazulenyl group or a cyclopentaphenanthrnyl group.

[10] The metallocene compound as described in any one of [1]–[8] wherein in the general formula (1) according to [1], each of K and L represents an indenyl group.

[11] The metallocene compound as described in [1]wherein in the general formula (1) according to [1], each of K and L represents an indenyl group and has R$^1$ or R$^2$ at the 2-position and R$^3$ at the 4-position of the indenyl group, represented by the following formula (2):

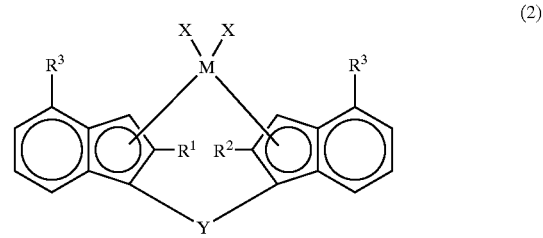

wherein R$^1$ represents an alkyl group of 1–6 carbon atoms, a halogen-containing alkyl group of 1–6 carbon atoms, a silicon-containing alkyl group of 1–6 carbon atoms, an aryl group of 6–16 carbon atoms or a halogen-containing aryl of 6–16 carbon atoms; R represents an aryl group of 6–16 carbon atoms, an alkyl group of 4–6 carbon atoms, an alicyclic hydrocarbon group of 3–16 carbon atoms or a heterocyclic group, provided that $R^1$ and $R^2$ are always different; and two $R^3$s may be the same or different and each represents a hydrogen atom, an alkyl group of 1–6 carbon atoms, a halogen-containing alkyl group of 1–6 carbon atoms, a silicon-containing alkyl group of 1–6 carbon atoms, an aryl group of 6–16 carbon atoms, a halogen-containing aryl group of 6–16 carbon atoms, a 2-furyl group, a substituted 2-furyl group, a 2-thienyl group, a substituted 2-thienyl group, a 2-furfuryl group or a substituted 2-furfuryl group.

[12] The metallocene compound as described in [11] wherein in the general formula (2) according to [11], $R^2$ represents a 2-furyl group, a substituted 2-furyl group, a 2-thienyl group, a substituted 2-thienyl group, a 2-furfuryl group or a substituted 2-furfuryl group.

[13] The metallocene compound as described in [11] wherein in the general formula (2) according to [11], $R^1$ represents an alkyl group of 1–6 carbon atoms and $R^2$ represents a 2-furyl group or a substituted 2-furyl group.

[14] The metallocene compound as described in any one of [11]–[13] wherein in the general formula (2) according to [11], two $R^3$s may be the same or different and each represents an aryl group of 6–16 carbon atoms or a halogen-containing aryl group of 6–16 carbon atoms.

[15] The metallocene compound as described in any one of [1] to [8] wherein in the general formula (1) according to [1], each of K and L represents an azulenyl group.

[16] The metallocene compound as described in [1] wherein in the general formula (1) according to [1], each of K and L represents an azulenyl group and has $R^4$ or $R^5$ at the 2-position and $R^6$ at the 4-position of the azulenyl group, represented by the following formula (3):

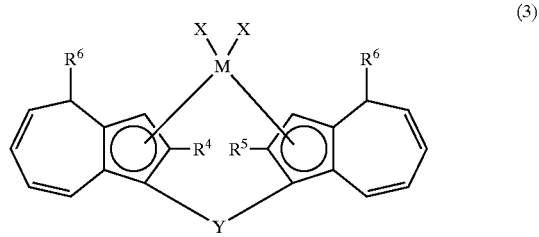

(3)

wherein $R^4$ represents an alkyl group of 1–6 carbon atoms, a halogen-containing alkyl group of 1–6 carbon atoms, a silicon-containing alkyl group of 1–6 carbon atoms, an aryl group of 6–16 carbon atoms or a halogen-containing aryl group of 6–16 carbon atoms; $R^5$ represents an aryl group of 6–16 carbon atoms, an alkyl group of 4–6 carbon atoms, an alicyclic hydrocarbon group of 3–16 carbon atoms or a heterocyclic group, provided that $R^4$ and $R^5$ are always different; and two $R^6$s may be the same or different and each represents a hydrogen atom, an alkyl group of 1–6 carbon atoms, a halogen-containing alkyl group of 1–6 carbon atoms, a silicon-containing alkyl group of 1–6 carbon atoms, an aryl group of 6–16 carbon atoms, a halogen-containing aryl group of 6–16 carbon atoms, a 2-furyl group, a substituted 2-furyl group, a 2-thienyl group, a substituted 2-thienyl group, a 2-furfuryl group or a substituted 2-furfuryl group.

[17] The metallocene compound as described in [16] wherein in the general formula (3) according to [16], $R^4$ represents an alkyl group of 1–6 carbon atoms, a halogen-containing alkyl group of 1–6 carbon atoms, a silicon-containing alkyl group of 1–6 carbon atoms, an aryl group of 6–16 carbon atoms or a halogen-containing aryl group of 6–16 carbon atoms; and $R^5$ represents a 2-furyl group, a substituted 2-furyl group, a 2-thienyl group, a substituted 2-thienyl group, a 2-furfuryl group or a substituted 2-furfuryl group.

[18] The metallocene compound as described in [16] wherein in the general formula (3) according to [16], $R^4$ represents an alkyl group of 1–6 carbon atoms and $R^5$ represents a 2-furyl group or a substituted 2-furyl group.

[19] The metallocene compound as described in any one of [16]–[18] wherein in the general formula (3) according to [16], two $R^6$s may be the same or different and each represents an aryl group of 6–16 carbon atoms or a halogen-containing aryl group of 6–16 carbon atoms.

[20] The metallocene compound as described in [1] wherein in the general formula (1) according to [1], each of K and L represents an azulenyl group and has $R^7$ at the 2-position and $R^8$ or $R^9$ at the 4-position of the azulenyl group, represented by the following formula (4):

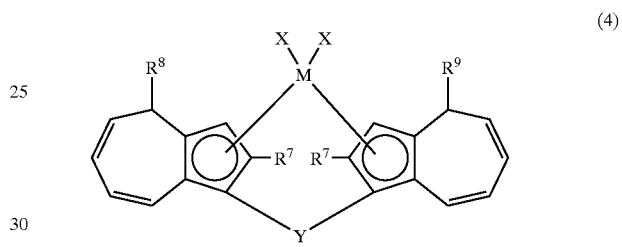

(4)

wherein two $R^7$s may be the same or different and each represent an alkyl group of 1–6 carbon atoms, a halogen-containing alkyl group of 1–6 carbon atoms, a silicon-containing alkyl group of 1–6 carbon atoms, an aryl group of 6–16 carbon atoms or a halogen-containing aryl group of 6–16 carbon atoms; $R^8$ represents an alkyl group of 1–6 carbon atoms, a halogen-containing alkyl group of 1–6 carbon atoms, a silicon-containing alkyl group of 1–6 carbon atoms, an aryl group of 6–16 carbon atoms, or a halogen-containing aryl group of 6–16 carbon atoms; and $R^9$ represents an aryl group of 6–16 carbon atoms, an alkyl group of 4–6 carbon atoms, an alicyclic hydrocarbon group of 3–16 carbon atoms or a heterocyclic group, provided that $R^8$ and $R^9$ are always different.

[21] The metallocene compound as described in [20] wherein in the general formula (4) according to [20], $R^8$ represents an alkyl group of 1–6 carbon atoms, a halogen-containing alkyl group of 1–6 carbon atoms, a silicon-containing alkyl group of 1–6 carbon atoms, an aryl group of 6–16 carbon atoms or a halogen-containing aryl group of 6–16 carbon atoms; and $R^9$ represents a 2-furyl group, a substituted 2-furyl group, a 2-thienyl group, a substituted 2-thienyl group, a 2-furfuryl group or a substituted 2-furfuryl group.

[22] The metallocene compound as described in [20] wherein in the general formula (4) according to [20], two $R^7$s may be the same or different and each represents an alkyl group of 1–6 carbon atoms; $R^8$ represents an aryl group of 6–16 carbon atoms or a halogen-containing aryl group of 6–16 carbon atoms; and $R^9$ represents 2-thienyl group or a substituted 2-thienyl group.

[23] The metallocene compound as described in any one of [1]–[8] wherein in the general formula (1) according to [1], each of K and L represents a benzoindenyl group.

[24] The metallocene compound as described in [1] wherein in the general formula (1) according to [1], each of K and L represents a benzoindenyl group and has $R^{10}$ or $R^{11}$ at the 2-position of the benzoindenyl group, represented by the following formula (5):

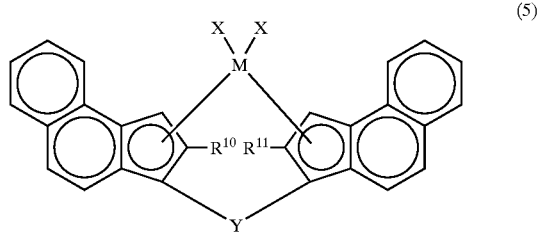

(5)

wherein $R^{10}$ represents an alkyl group of 1–6 carbon atoms, a halogen-containing alkyl group of 1–6 carbon atoms, a silicon-containing alkyl group of 1–6 carbon atoms, an aryl group of 6–16 carbon atoms or a halogen-containing aryl group of 6–16 carbon atoms; and $R^{11}$ represents an aryl group of 6–16 carbon atoms, an alkyl group of 4–6 carbon atoms, an alicyclic hydrocarbon group of 3–16 carbon atoms or a heterocyclic group, provided that $R^{10}$ and $R^{11}$ are always different.

[25] The metallocene compound as described in [24] wherein in the general formula (5) according to [24], $R^{11}$ represents a 2-furyl group, a substituted 2-furyl group, a 2-thienyl group, a substituted 2-thienyl group, a 2-furyl group, a substituted 2-thienyl group, a 2-furfuryl group or a substituted 2-furfuryl group.

[26] The metallocene compound as described in [1] wherein in the general formula (1) according to [1], each of K and L represents an indenyl group and has $R^{12}$ or $R^{13}$ at the 2-position and $R^{14}$ at the 4-position of the indenyl group, represented by the following formula (6):

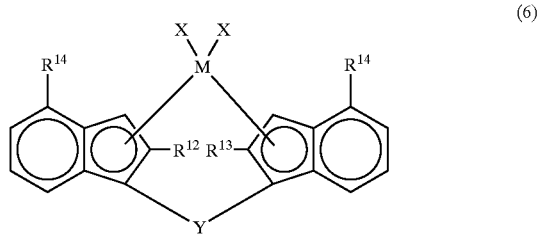

(6)

wherein $R^{12}$ represents an alkyl group of 1–3 carbon atoms; $R^{13}$ represents an alkyl group of 2–3 carbon atoms provided that $R^{12}$ and $R^{13}$ are always different; and two $R^{14}$'s may be the same or different and each represents an aryl group of 6–16 carbon atoms, a halogen-containing aryl group of 6–16 carbon atoms, a 2-furyl group, a substituted 2-furyl group, a 2-thienyl group, a substituted 2-thienyl group, a 2-furfuryl group or a substituted 2-furfuryl group, with the proviso that the two $R^{14}$'s cannot be either an aryl group of 6–16 carbon atoms or a halogen-containing aryl group of 6–16 carbon atoms at the same time.

[27] A process for the production of an olefin polymer which comprises using an olefin polymerization catalyst containing the metallocene compound as described in any one of [1]–[26], an activating compound and, optionally, an organoaluminum compound.

[28] A process for the production of an olefin polymer which comprises using an olefin polymerization catalyst containing (A) a supported catalyst component that is prepared from the metallocene compound as described in any one of [1]–[26], an activating compound, a support in the form of finely divided particles and, optionally, an organoaluminum compound, together with (B) an organoaluminum compound.

[29] A process for the production of an olefin polymer which comprises using an olefin polymerization catalyst containing (A) a supported catalyst component that is prepared from the metallocene compound as described in any one of [1]–[26], an ion-exchangeable layer compound or an inorganic silicate and, optionally, an organoaluminum compound, together with (B) an organoaluminum compound.

[30] An olefin polymer produced by a process for the production of an olefin polymer as described in any one of [27]–[29].

[31] The olefin polymer as described in [30] wherein the olefin polymer is a propylene/olefin copolymer comprising as structural units, a propylene unit and an olefin unit other than propylene and the content of the olefin unit other than propylene is 0.1 to 80 molar % based on the molar number of the structural units constituting the copolymer.

[32] The olefin polymer as described in [31] wherein the olefin unit other than propylene is an ethylene unit, a 1-butene unit, or an ethylene unit and a 1-butene unit.

This invention provides an olefin polymer having high molecular weight and high stereoregularity.

This invention also allows an olefin polymer having high molecular weight and high stereoregularity to be produced with high polymerization activity.

This invention also allows a propylene/ethylene copolymer having sufficiently high molecular weight to be obtained even when its ethylene content is high.

This invention further allows a propylene/1-butene copolymer having sufficiently high molecular weight to be obtained even at high temperatures to be practical.

DESCRIPTION OF THE PREFERRED EMBODIMENTS

The metallocene compounds of this invention are represented by the following formula (1):

$$Y_qKLMX_2 \quad (1)$$

wherein M represents a titanium atom, a zirconium atom or a hafnium atom, and preferably a zirconium atom.

Y represents a linking group bridging K and L and is a methylene group, an ethylene group, a tetraalkylethylene group having alkyl of 1–6 carbon atoms, a dialkylmethylene group having alkyl of 1–6 carbon atoms, a divalent linking group containing within a backbone thereof, an aryl group of 6–16 carbon atoms or a halogenated aryl group of 6–16 carbon atoms, or a divalent linking group containing a silicon atom, a germanium atom, an oxygen atom, a nitrogen atom, a phosphorous atom or a boron atom. Alternatively, Y represents a divalent linking group formed by connecting in series at least two linking groups selected from the foregoing linking groups.

Preferably, Y is a methylene group, an ethylene group, a tetraalkylethylene group having alkyl of 1–6 carbon atoms, a dialkylmethylene group having alkyl of 1–6 carbon atoms, or a divalent linking group containing a silicon atom, a germanium atom, an oxygen atom, a nitrogen atom, a phosphorous atom or a boron atom. Y may be also a linking group constructed by combining two or more of these linking components.

Specific examples of the divalent linking group containing a silicon atom include a dialkylsilylene group having alkyl of 1–6 carbon atoms, a diarylsilylene group having aryl of 6–16 carbon atoms, a dibenzylsilylene group and an alkylarylsilylene group having alkyl of 1–6 carbon atoms and aryl of 6–16 carbon atoms.

Specific examples of the divalent linking group containing a germanium atom include a dialkylgermylene group having alkyl of 1–6 carbon atoms, a diarylgermylene group having aryl of 6–16 carbon atoms, a dibenzylgermylene group and an alkylarylgermylene group having alkyl of 1–6 carbon atoms and aryl of 6–16 carbon atoms.

Specific examples of the divalent linking group containing an oxygen atom include a 5-membered ring having the oxygen atom in the ring frame as described in J. Chem. Soc. Dalton Trans., pp. 2207–216 (1991) and —Si(Me)$_2$—O—Si (Me)$_2$— or —Si (Me)$_2$—O—Si (Me)$_2$—O—Si(Me)$_2$— wherein "Me" represents a methyl group, both of which are described in J. Organomet. Chem., 501, pp. 211–218 (1995).

Specific examples of the divalent linking group containing a nitrogen atom include —(Me)N—(CH$_2$)$_2$—N(Me)— wherein "Me" represents a methyl group as described in J. Organomet. Chem., 519, pp. 269–272 (1996) and —Si(Me)$_2$—N(C$_4$H$_9$)—Si(Me)$_2$— wherein "Me" represents a methyl group as described in J. Organomet. Chem., 564, pp. 109–114 (1998).

Specific examples of the divalent linking group containing a phosphorous atom include —P(Ph)— and —P(R)— wherein "Ph" represents a phenyl and "R" represents an alkyl group, as described in J. Mol. Catal. A., 128, pp. 245–256 (1998).

Specific examples of the divalent linking group containing a boron atom for use include —B(Ph)— wherein "Ph" represents a phenyl group as described in J. Organomet. Chem., 525, pp. 287–289 (1996), —B(N(i-Pr)$_2$)— wherein "i-Pr" represents an isopropyl group, —B(NMe$_2$)— wherein "Me" represents a methyl group, —B(NMe$_2$)—B(NMe$_2$)— wherein "Me" represents a methyl group as described in Organometallics Chem., 18, pp. 2288–2290 (1999) and WO00/20426, —B(C(SiMe$_3$)$_3$— wherein "Me" represents a methyl group as described in EJ. Organomet. Chem., 536–537, pp. 361–373 (1997), —B(Ph)(L)— wherein "Ph" represents a phenyl group and "L" represents OEt$_2$, PME$_3$, or a 5-membered ring containing an oxygen atom in the ring frame as described in Chem. Commun., pp. 1105–1106 (1999), and a linking group of the following general formula:

wherein $R^a$ is preferably an alkyl group of 1–6 carbon atoms and $R^b$ is preferably a halogen atom, as described in Angew. Chem. Int. Ed., 38, No. 6, pp. 2439–2443 (1999).

Specific examples of the divalent linking group formed by connecting in series at least two linking groups selected from the divalent linking groups as exemplified above include the linking groups as shown in (7)–(9) below as the preferred representatives. The hydrogen atoms in these illustrated linking groups may be optionally substituted.

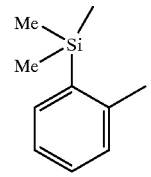

(7)

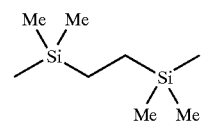

(8)

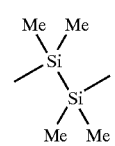

(9)

More preferred as the linking group Y are a methylene group, an ethylene group, a dialkylsilylene group having alkyl of 1–6 carbon atoms, a dialkylgermylene group having alkyl of 1–6 carbon atoms, a tetraalkylethylene group having alkyl of 1–6 carbon atoms, a dialkylmethylene group having alkyl of 1–6 carbon atoms, a diarylsilylene group having aryl of 6–16 carbon atoms, a diarylgermylene group having aryl of 6–16 carbon atoms, an alkylarylsilylene group having alkyl of 1–6 carbon atoms and aryl of 6–16 carbon atoms, and an alkylarylgermylene group having alkyl of 1–6 carbon atoms and aryl of 6–16 carbon atoms. Still more preferred are a dimethylsilylene group, a diethylsilylene group, a methylphenylsilylene group, a diphenylsilylene group, a dimethylgermylene group, a diethylgermylene group, a methylphenylgermylene group and a diphenylgermylene group. The most preferred is a dimethylsilylene group or a dimethylgermylene group.

q is an integer representing the number of the linking groups and is 0, 1 or 2. It is preferably 0 or 1, and more preferably 1.

L is a ligand having a conjugated 5-membered ring skeleton that is coordinated to M. K may be the same as or different from L and represents a ligand having a conjugated 5-membered ring skeleton that is coordinated to M, or alternatively, when q is 1, K may be —NH— (N represents a nitrogen atom and H represents a hydrogen atom) or may be —PH— (P represents a phosphorous atom and H represents a hydrogen atom).

At least one of the hydrogen atoms possessed by K or by L may each independently be replaced by an alkyl group of 1–10 carbon atoms, a halogen-containing alkyl group of 1–10 carbon atoms, a silicon-containing alkyl group of 1–10 carbon atoms, an aryl group of 6–16 carbon atoms, a halogen-containing aryl group of 6–16 carbon atoms, an alkenyl group of 2–10 carbon atoms, an arylalkyl group of 7–40 carbon atoms, an alkylaryl group of 7–40 carbon atoms, an alicyclic hydrocarbon group of 3–16 carbon atoms, a siloxyl group, an alkoxyl group, a halogen atom, an amino group, a dialkyl-substituted amino group, a heterocyclic group, a SR$^a$ group (S represents a sulfur atom and R$^a$ represents a halogen atom, an alkyl group of 1–10 carbon atoms or an aryl group of 6–16 carbon atoms), or a PR$^b_2$ group (P represents a phosphorous atom and two R$^b$s may be the same or different and each represents a halogen atom, an alkyl group of 1–10 carbon atoms or an aryl group of 6–16 carbon atoms), with the proviso that when each of K and L represents a ligand having a conjugated 5-membered ring skeleton, at least one substituent having replaced the hydrogen in either of the ligands does not exist at the corresponding position in the other ligand.

The aryl group of 6–16 carbon atoms may optionally be substituted with one or more hydrocarbon groups, silicon-containing hydrocarbon groups, or halogen-containing hydrocarbon groups, each with 1–20 carbon atoms, preferably with 1–6 carbon atoms, or alternatively, it may be substituted with an alkoxy group, a dialkyl-substituted amino group, an amino group, a 2-furyl group, a substituted 2-furyl group, a 2-thienyl group, a substituted 2-thienyl group, a 2-furfuryl group, a substituted 2-furfuryl group, a siloxyl group, a $SR^a$ group (S represents a sulfur atom and $R^a$ represents a halogen atom, an alkyl group of 1–10 carbon atoms or an aryl group of 6–16 carbon atoms), or a $PR^b{}_2$ group (P represents a phosphorous atom, and two $R^b$s may be the same or different and each represents a halogen atom, an alkyl group of 1–10 carbon atoms or an aryl group of 6–16 carbon atoms).

Two Xs may be the same or different and each represents a halogen atom, an alkyl group of 1–6 carbon atoms, an aryl group of 6–16 carbon atoms, an alkylaryl group having alkyl of 1–6 carbon atoms and aryl of 6–16 carbon atoms or an arylalkyl group having aryl of 6–16 carbon atoms and alkyl of 1–6 carbon atoms, which atom or group is bonded to M. X also can form a diene compound when two Xs are bonded as described in WO00/20426 (e.g., in Example 12) and can adopt a structure such that the two double bonds are respectively coordinated to M. Such diene compounds preferably have a butadiene skeleton. Especially, 1,4-diphenyl-1,3-butadiene is most preferred. In addition to those mentioned above, specific examples of X for use include an alkoxy group, a siloxy group, an amino group, a halogen-containing hydrocarbon group such as —$CF_3$, a silicon-containing hydrocarbon group such as —$CH_2Si(CH_3)_3$, a sulfonic acid-containing group such as —$SO_3CF_3$, a sulfur-containing group, a phosphorus-containing group, and an optionally substituted biphenyl group. Particularly preferred, as X is a chlorine atom.

Preferably, the metallocene compounds of this invention are those wherein in the general formula (1), each of K and L represents a ligand having a conjugated 5-membered ring skeleton; q is 1; and in K and L, at least the substituents at the 2-positions of K and L differ from each other, or at least the substituents at the 4-positions of K and L differ from each other, or at least the substituents at the 2-positions and at the 4-positions of K and L differ from each other between the two ligands.

When in the general formula (1) each of K and L represents a ligand having a conjugated 5-membered ring skeleton, q is 1 and at least the substituents at the 2-positions of K and L differ from each other, at least one of them is an alkyl group of 2–6 carbon atoms, an aryl group of 6–16 carbon atoms, a halogen-containing aryl group of 6–16 carbon atoms, an alkylaryl group of 7–40 carbon atoms, an alicyclic hydrocarbon group of 3–16 carbon atoms or a heterocyclic group, preferably an alkyl group of 3–6 carbon atoms, an aryl group of 6–16 carbon atoms, an alicyclic hydrocarbon group of 3–16 carbon atoms or a heterocyclic group, more preferably an alkyl group of 4–6 carbon atoms, an aryl group of 6–16 carbon atoms, an alicyclic hydrocarbon group of 3–16 carbon atoms or a heterocyclic group, further more preferably an alkyl group of 5–6 carbon atoms, an aryl group of 6–16 carbon atoms, an alicyclic hydrocarbon group of 3–16 carbon atoms or a heterocyclic group, particularly preferably an aryl group of 6–16 carbon atoms or a heterocyclic group, more particularly preferably a phenyl group, a tolyl group, a 2-furyl group, a substituted 2-furyl group, a 2-thienyl group, a substituted 2-thienyl group, and most preferably a 2-furyl group or a substituted 2-furyl group, or alternatively, the difference in the carbon numbers of the at least two substituents at the 2-positions is in the range of 3–10, preferably in the range of 3–7, more preferably in the range of 3–5, and most preferably in the range of 4–5. Specific examples of the preferred combination of the two substituents at the 2-positions include a phenyl group and a methyl group, a tolyl group and a methyl group, a phenyl group and an ethyl group, a phenyl group and a n-propyl group, a phenyl group and an isopropyl group, a n-butyl group and a methyl group, an isobutyl group and a methyl group, a cyclohexyl group and a methyl group, a furyl group and a methyl group, a substituted 2-furyl group and a methyl group, a furyl group and an ethyl group, a substituted 2-furyl group and an ethyl group, a thienyl group and a methyl group, and a 2-thienyl group and a methyl group. More preferable combinations are a phenyl group and a methyl group, a tolyl group and a methyl group, a furyl group and a methyl group, a substituted 2-furyl group and a methyl group, a thienyl group and a methyl group, a 2-thienyl group and a methyl group, etc. The most preferable combination is a furyl group and a methyl group, a substituted 2-furyl group and a methyl group, a thienyl group and a methyl group, or a substituted 2-thienyl group and a methyl group.

Preferably, the metallocene compounds of this invention are also those wherein in the general formula (1), each of K and L represents a ligand having a conjugated 5-membered ring skeleton; q is 1; and between the two ligands K and L at least the substituent at the 4-position of at least one ligand is an alkyl group of 1–10 carbon atoms, a halogen-containing alkyl group of 1–10 carbon atoms, a silicon-containing alkyl group of 1–10 carbon atoms, an alkenyl group of 2–10 carbon atoms, an arylalkyl group of 7–40 carbon atoms, an alkylaryl group of 7–40 carbon atoms, a siloxyl group, an alkoxyl group, a halogen atom, an amino group, a dialkyl-substituted amino group, a heterocyclic group, a $SR^a$ group (S represents a sulfur atom and $R^a$ represents a halogen atom, an alkyl group of 1–10 carbon atoms or an aryl group of 6–16 carbon atoms), or a $PR^b{}_2$ group (P represents a phosphorous atom, two $R^b$s may be the same or different and each represents a halogen atom, an alkyl group of 1–10 carbon atoms or an aryl group of 6–16 carbon atoms). More preferred are those wherein the substituent at the 4-position is an alkyl group of 1–10 carbon atoms, a halogen-containing alkyl group of 1–10 carbon atoms, a silicon-containing alkyl group of 1–10 carbon atoms, an arylalkyl group of 7–40 carbon atoms, an alkylaryl group of 7–40 carbon atoms or a heterocylcic group. The most preferred are those wherein the substituent at the 4-position is an alkyl group of 1–10 carbon atoms.

Also preferably, the metallocene compounds of this invention are those wherein in the general formula (1), each of K and L represents a ligand having a conjugated 5-membered ring skeleton; q is 1; between the two ligands K and L, at least the substituents at the 4-positions differ from each other. Specific examples of the combination of the two substituents at the 4-positions include a phenyl group and a tolyl group, a phenyl group and a thienyl group, a phenyl group and a substituted thienyl group, a phenyl group and a 4-t-butyl-phenyl group, a phenyl group and an isopropyl group and a phenyl group and a naphthyl group. More preferable combinations are a phenyl group and a tolyl group, a phenyl group and a 4-t-butyl-phenyl group, a phenyl group and a naphthyl group, and a phenyl group and a substituted thienyl group, etc.

Also preferably, the metallocene compounds of this invention are those wherein in the general formula (1), each of K and L represents a ligand having a conjugated 5-membered ring skeleton; q is 1; and at least the substituents at the 2- and 4-positions of K and L differ from each other. The aforementioned representative substituents in the case where at least the substituents at the 2-positions differ from each other and the aforementioned representative substituents in the case where at least the substituents at the 4-positions differ from each other may be combined and indicated for such examples.

Preferably, the metallocene compounds of this invention are those wherein at least one of the hydrogen atoms possessed by K may be each independently replaced by an alkyl group of 1–6 carbon atoms, a halogen-containing alkyl group of 1–6 carbon atoms, a silicon-containing alkyl group of 1–6 carbon atoms, an aryl group of 6–16 carbon atoms, a halogen-containing aryl group of 6–16 carbon atoms, a 2-furyl group, a substituted 2-furyl group, a 2-thienyl group, a substituted 2-thienyl group, a 2-furfuryl group, a substituted 2-furfuryl group, a siloxyl group, or an alkoxyl group; and at least one of the hydrogen atoms possessed by K is replaced by a 2-furyl group, a substituted 2-furyl group, a 2-thienyl group, a substituted 2-thienyl group, a 2-furfuryl group or a substituted 2-furfuryl group. In these cases at least one of the hydrogen atoms possessed by L may be each independently replaced by an alkyl group of 1–6 carbon atoms, a halogen-containing alkyl group of 1–6 carbon atoms, a silicon-containing alkyl group of 1–6 carbon atoms, an aryl group of 6–16 carbon atoms, a halogen-containing aryl group of 6–16 carbon atoms, a siloxyl group or an alkoxyl group.

As used herein, the terms, "substituted 2-furyl group," "substituted 2-thienyl group" and "substituted 2-furfuryl group" refer to those wherein the hydrogen atoms bonded to the carbon atoms forming the skeletons of a 2-furyl group, a 2-thienyl group and a 2-furfuryl group are, respectively, replaced by other substituents. As used herein, the "other substituents" are preferably a hydrocarbon group, a silicon-containing hydrocarbon group, and a halogen-containing hydrocarbon group, each with 1–20 carbon atoms, and preferably with 1–6 carbon atoms. Other than those mentioned, there may be used as the "other substituent" a halogen atom, SR, $SO_2H$, $SO_2R$, COOH, COOR, $NO_2$, $BR_2$, COR, CHO, $C(OH)R_2$, $CH_2CH_2OH$, $PO(OR)_2$, etc. The methods of their syntheses are described in H. Yamanaka et al., "The Chemistry of Heterocyclic Compounds," 2nd Ed., 1998, p. 108, Kodansha Scientific Co., Ltd, for example. In addition, R represents a hydrocarbon group of 1–20 carbon atoms in the notations of the substituents described above. The synthetic examples of the "substituted 2-furyl groups" are also described in T. Kunieda et al., "The Chemistry of Heterocycles," 1st Ed., 1st Print, Mar. 25, 2002, p. 26, Kagaku Dojin Co., Ltd.

In this invention, specific examples of the substituted 2-furyl group preferably include a 2-(5-methyl)-furyl group, a 2-(5-ethyl)-furyl group, a 2-(5-t-butyl)-furyl group, a 2-(5-trimethylsilyl)-furyl group, a 2-(4,5-dimethyl)-furyl group, a 2-(5-phenyl)-furyl group and a 2-benzofuryl group.

In this invention, specific examples of the substituted 2-thienyl group preferably include a 2-(5-methyl)-thienyl group, 2-(5-ethyl)-thienyl group, a 2-(5-t-butyl)-thienyl group, a 2-(5-trimethylsilyl)-thienyl group, a 2-(4,5-dimethyl)-thienyl group, a 2-(5-phenyl)-thienyl group and a 2-benzothienyl group.

In this invention, specific examples of the substituted 2-furfuryl groups preferably include those wherein the hydrogen atom at the 5-position of the furyl group in the 2-furfuryl group has been replaced by a methyl group, a t-butyl group, a trimethylsilyl group or a phenyl group and those wherein the hydrogen atoms at the 4- and 5-positions have both been replaced by methyl groups.

In this invention, specific examples of the alicyclic hydrocarbon group include cyclopropane, cyclobutane, cyclopentane, cyclohexane, cycloheptane, cyclooctane, methylcyclopentane, dimethylcyclopentane, methylcyclohexane, cyclopentene, cyclohexene, cyclopentadiene, cyclohexadiene, and substituted versions of the foregoing according the description of Morrison and Boyd, "Organic Chemistry" translated by Nakanishi et al., 3rd Ed. 8th Print, pp. 356–359 (1977).

In this invention, specific examples of the heterocyclic group include heteroaromatic groups such as a 2-furyl group, a substituted 2-furyl group, a 2-thienyl group, a substituted 2-thienyl group, a 2-furfuryl group, and a substituted 2-furfuryl group. Furthermore, there may also be mentioned a pyrrol group, an imidazole group, an oxazole group, a thiazole group, a pyrazole group, a 3-pyrroline group, a pyrrolidine group, a pyridine group, a pyrimidine group, a purine group, a quinoline group, an isoquinoline group, a carbazole group and substituted versions of the foregoing according the description of Morrison and Boyd, "Organic Chemistry" translated by Nakanishi et al., 3rd Ed. 8th Print, pp. 1231–1232 (1977). In this invention, specific examples of the heterocyclic group include, other than those mentioned above, heterocyclic groups containing at least one atom from silicone (Si), boron (B) and phosphorous (P) and their substituted versions, such as a silol group, a substituted silol group, a boratabenzene group, a substituted boratabenzene group, a phosphoryl group, and a substituted phosphoryl group. Particularly, in this invention the heterocyclic group has preferably such a structure that it does not directly bond to K or L through the heteroatom of the heterocyclic group. In this invention, the heterocyclic group is preferably a heteroaromatic group, and more preferably a 2-furyl group, a substituted 2-furyl group, a 2-thienyl group, a substituted 2-thienyl group, a 2-furfuryl group or a substituted 2-furfuryl group.

In the metallocene compound of the general formula (1) according to this invention, L may be a ligand having a conjugated 5-membered ring skeleton that is coordinated to M, and K may also be independently a ligand having a conjugated 5-membered ring skeleton that is coordinated to M. Specific examples of the ligand having a conjugated 5-membered ring skeleton include a cyclopentadienyl group, an indenyl group, a benzoindenyl group, a fluorenyl group, a tetrahydroindenyl group, an azulenyl group, a tetrahydroazulenyl group and a cyclopentaphenanthryl group. More preferred are a cyclopentadienyl group, an indenyl group, a benzoindenyl group, an azulenyl group and a fluorenyl group.

When q is 1, K may be —NH— (N represents a nitrogen atom and H represents a hydrogen atom) or may be —PH— (P represents a phosphorous atom and H represents a hydrogen atom), both of which are bonded to M. However, the hydrogen atom may be replaced by an alkyl group of 1–10 carbon atoms, a halogen-containing alkyl group of 1–10 carbon atoms, a silicon-containing alkyl group of 1–10 carbon atoms, an alkenyl group of 2–10 carbon atoms, an arylalkyl group of 7–40 carbon atoms, an alkylaryl group of 7–40 carbon atoms, a siloxyl group, an alkoxyl group, a halogen atom, an amino group, a dialkyl-substituted amino group, a heterocyclic group, a $SR^a$ group (S represents a sulfur atom and $R^a$ represents a halogen atom, an alkyl group of 1–10 carbon atoms or an aryl group of 6–16 carbon atoms), or a $PR^b_2$ group (P represents a phosphorous atom, and two $R^b$s may be the same or different and each represents a halogen atom, an alkyl group of 1–10 carbon atoms or an aryl group of 6–16 carbon atoms). Preferred as —NH— of which the hydrogen atom may be replaced are —N(t-butyl)-, —N(phenyl)- and —N(methyl)-. More preferred is —N(t-butyl)-. Preferred as —PH— of which the hydrogen atom may be replaced are —P(methyl)-, —P(ethyl)-, —P(phenyl)-, and —P(t-butyl)-. More preferred is —P(t-butyl)-.

When K is —NH— of which the hydrogen atom may be replaced, Y is preferably a divalent linking group containing a silicon atom and M is preferably a titanium atom. L is preferably a cyclopentadiene group, an indenyl group, a benzoindenyl group or a fluorenyl group, and more preferably a cyclopentadienyl group or an indenyl group. In these cases at least one of the hydrogen atoms possessed by L is preferably replaced by a heterocyclic group; within the group it is more preferably replaced by a 2-furyl group, a substituted 2-furyl group, a 2-thienyl group or a substituted 2-thienyl group.

The metallocene compounds of the general formula (1) according to this invention are those wherein each of K and L is preferably a ligand having a conjugated 5-membered ring skeleton. Particularly preferred are the cases where each of K and L is a cyclopentadienyl group, where K is a cyclopentadienyl group and L is a fluorenyl group, where each of K and L is an indenyl group, where K is an indenyl group and L is a fluorenyl group or a benzoindenyl group, where each of K and L is an azulenyl group, where each of K and L is a benzoindenyl group, where K is a benzoindenyl group and L is a fluorenyl group, where K is a fluorenyl group and L is a cyclopentadienyl group, where K is a fluorenyl group and L is an indenyl group, and where K is a fluorenyl group and L is a benzoindenyl group. The most preferred is the case where each of K and L is an indenyl group, where each of K and L is an azulenyl group, or where each of K and L is a benzoindenyl group.

Examples of the ligand having a conjugated 5-membered ring skeleton of K or L for use include those which contain atoms other than carbon atom in their skeletons, such as a nitrogen atom (N), a sulfur atom (S), a phosphorous atom (P), a boron atom (B), an oxygen atom (O) and a silicon atom (Si). Their non-limiting representatives may include ligands having the structures (10)–(16) shown below.

(10)

(11)

(12)

-continued

(13)

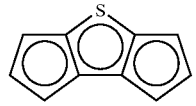
(14)

(15)

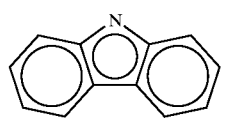
(16)

The ligands containing atoms other than a carbon atom are, for example, described in J. Am. Chem. Soc., 123, pp. 4763–4773 (2001), J. Mol. Cat. A, 128, pp. 155–165 (1998), J. Am. Chem. Soc., 120, p. 10786 (1998) and Chem. Ber., 129, pp. 1517–1529 (1996).

When K is a cyclopentadienyl group and L is a fluorenyl group, or when K is a fluorenyl group and L is a cyclopentadienyl group conversely, K or L preferably has at least a substituent at the 3-position of the cyclopentadienyl group.

Such compounds include, for example, isopropylidene(3-(2-(5-methyl)-furyl)-cyclopentadienyl)(fluorenyl)zirconium dichloride, isopropylidene(3-(2-furyl)-cyclopentadienyl)(fluorenyl)zirconium dichloride.

When each of K and L is an indenyl group, the metallocene compounds having $R^1$ or $R^2$ at the 2-position and $R^3$ at the 4-position of the indenyl group and represented by the following general formula (2) are preferable.

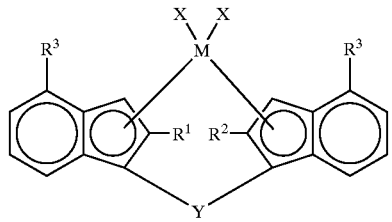
(2)

In the general formula (2) above, $R^1$ represents an alkyl group of 1–6 carbon atoms, a halogen-containing alkyl group of 1–6 carbon atoms, a silicon-containing alkyl group of 1–6 carbon atoms, an aryl group of 6–16 carbon atoms or a halogen-containing aryl group of 6–16 carbon atoms. $R^1$ is preferably an alkyl group of 1–6 carbon atoms, more preferably a methyl group, an ethyl group, an n-propyl group, an isopropyl group, an n-butyl group or a t-butyl group, and most preferably, a methyl group or an ethyl group.

The aryl group of 6–16 carbon atoms above may optionally be substituted with one or more hydrocarbon groups, silicon-containing hydrocarbon groups or halogen-containing hydrocarbon groups, each with 1–20 carbon atoms and preferably with 1–6 carbon atoms, or alternatively may be substituted with an alkoxyl group, a dialkyl-substituted amino group, an amino group, a 2-furyl group, a substituted 2-furyl group, a 2-thienyl group, a substituted 2-thienyl group, a 2-furfuryl group, a 2-thienyl group, a substituted 2-thienyl group, a 2-furfuryl group, a substituted 2-furfuryl group, a siloxyl group, a $SR^a$ group (S represents a sulfur atom and $R^a$ represents a halogen atom, an alkyl group of 1–10 carbon atoms or an aryl group of 6–16 carbon atoms), or a $PR^b{}_2$ group (P represents a phosphorous atom; and two $R^b$s may be the same or different and each represents a halogen atom, an alkyl group of 1–10 carbon atoms or an aryl group of 6–16 carbon atoms).

In the general formula (2) above, $R^2$ represents an aryl group of 6–16 carbon atoms, an alkyl group of 4–6 carbon atoms, an alicyclic hydrocarbon group of 3–16 carbon atoms or a heterocyclic group on condition that $R^2$ is always different from $R^1$. $R^2$ is preferably an aryl group of 6–16 carbon atoms, an alkyl group of 5–6 carbon atoms or a heteroaromatic group, more preferably an aryl group of 6–16 carbon atoms or a heteroaromatic group, and most preferably, a heteroaromatic group. The heteroaromatic group is preferably a 2-furyl group, a substituted 2-furyl group, a 2-thienyl group, a substituted 2-thienyl group, a 2-furfuryl group or a substituted 2-furfuryl group, more preferably a 2-furfuryl group or a substituted 2-furfuryl group, even more preferably, a substituted 2-furyl group, and most preferably, a 2-(5-methyl)-furyl group.

In the general formula (2) above, two $R^3$s may be the same or different and each represents a hydrogen atom, an alkyl group of 1–6 carbon atoms, a halogen-containing alkyl group of 1–6 carbon atoms, a silicon-containing alkyl group of 1–6 carbon atoms, an aryl group of 6–16 carbon atoms, a halogen-containing aryl group of 6–16 carbon atoms, a 2-furyl group, a substituted 2-furyl group, a 2-thienyl group, a substituted 2-thienyl group, a 2-furfuryl group or a substituted 2-furfuryl group. Two $R^3$s may be the same or different and each preferably is an alkyl group of 1–6 carbon atoms, an aryl group of 6–16 carbon atoms, a halogen-containing aryl group of 6–16 carbon atoms, a 2-thienyl group or a substituted 2-thienyl group, more preferably an aryl group of 6–16 carbon atoms, a halogen-containing aryl group of 6–16 carbon atoms or a substituted 2-thienyl group, and most preferably a phenyl group, a naphthyl group, a chlorophenyl group or a fluorophenyl group.

The aryl group of 6–16 carbon atoms above may optionally be substituted with one or more hydrocarbon groups, silicon-containing hydrocarbon groups, or halogen-containing hydrocarbon groups, each with 1–20 carbon atoms and preferably with 1–6 carbon atoms, or alternatively may be substituted with an alkoxyl group, a dialkyl-substituted amino group, an amino group, a 2-furyl group, a substituted 2-furyl group, a 2-thienyl group, a substituted 2-thienyl group, a 2-furfuryl group, a substituted 2-furfuryl group, a siloxyl group, a $SR^a$ group (S represents a sulfur atom and $R^a$ represents a halogen atom, an alkyl group of 1–10 carbon atoms or an aryl group of 6–16 carbon atoms), or a $PR^b{}_2$ group (P represents a phosphorous atom; and two $R^b$s may be the same or different and each represents a halogen atom, an alkyl group of 1–10 carbon atoms or an aryl group of 6–16 carbon atoms).

The metallocene compounds represented by the general formula (2) above are preferably those wherein in the general formula (2), $R_1$ represents an alkyl group of 1–6 carbon atoms and $R^2$ represents a 2-furyl group or a substituted 2-furyl group.

The metallocene compounds represented by the general formula (2) above are more preferably those wherein in the general formula (2), $R_1$ represents an alkyl group of 1–6 carbon atoms; $R^2$ represents a 2-furyl group or a substituted 2-furyl group; and two $R^3$s may be the same or different and each represents an aryl group of 6–16 carbon atoms or a halogen-containing aryl group of 6–16 carbon atoms.

Particularly, such metallocene compounds represented by the general formula (2) are preferably used as catalytic components for olefin polymerization to produce olefin polymers having high molecular weight and high stereoregularity with high polymerization activity. Particularly, such metallocene compounds can preferably be used as catalytic components for olefin polymerization to carry out the copolymerization of propylene with an olefin other than propylene and to produce a propylene/olefin copolymer such that the molecular weight of the obtained propylene/olefin copolymer has either hardly decreased or experienced only a small decrease and is similar to or higher than the molecular weight of propylene homopolymer produced under the same conditions even if the content of the olefin unit other than propylene has increased. Another characteristic feature is that when the propylene/ethylene polymerization is carried out, the melting point of the obtained propylene/ethylene copolymer decreases very efficiently as the ethylene content increases. The reason is not clear, but it is presumably due to the fact that the ethylene units have been inserted into the copolymer in a highly random manner. In these cases, the olefin other than propylene is preferably ethylene or 1-butene, or ethylene and 1-butene. Ethylene is most preferred among those.

Specific examples of such metallocene compounds may include: dimethylsilylene(2-methyl-4-phenyl-indenyl)(2-(2-furyl)-4-phenyl-indenyl)zirconium dichloride, dimethylsilylene(2-methyl-4-phenyl-indenyl)(2-(2-(5-methyl)-furyl)-4-phenyl-indenyl)zirconium dichloride, diphenylsilylene(2-methyl-4-phenyl-indenyl)(2-(2-(5-methyl)-furyl)-4-phenyl-indenyl)zirconium dichloride, dimethylgermylene(2-methyl-4-phenyl-indenyl)(2-(2-(5-methyl)-furyl)-4-phenyl-indenyl)zirconium dichloride, dimethylsilylene(2-methyl-4-phenyl-indenyl)(2-(2-(5-t-butyl)-furyl)-4-phenyl-indenyl)zirconium dichloride, dimethylsilylene(2-methyl-4-phenyl-indenyl)(2-(2-(5-trimethylsilyl)-furyl)-4-phenyl-indenyl)zirconium dichloride, diethylsilylene(2-methyl-4-phenyl-indenyl)(2-(2-(5-methyl)-furyl)-4-phenyl-indenyl)zirconium dichloride, methylphenylsilylene(2-methyl-4-phenyl-indenyl)(2-(2-(5-methyl)-furyl)-4-phenyl-indenyl)zirconium dichloride, diphenylsilylene(2-methyl-4-phenyl-indenyl)(2-(2-(5-methyl)-furyl)-4-phenyl-indenyl)zirconium dichloride, dimethylgermylene(2-methyl-4-phenyl-indenyl)(2-(2-(5-methyl)-furyl)-4-phenyl-indenyl)zirconium dichloride, dimethylsilylene(2-methyl-4-phenyl-indenyl)(2-(2-(5-methyl)-furyl)-4-phenyl-indenyl)titanium dichloride, dimethylsilylene(2-methyl-4-phenyl-indenyl)(2-(2-(5-methyl)-furyl)-4-phenyl-indenyl)hafnium dichloride, dimethylgermylene(2-methyl-4-phenyl-indenyl)(2-(2-(5-methyl)-furyl)-4-phenyl-indenyl)titanium dichloride, dimethylgermylene(2-methyl-4-phenyl-indenyl)(2-(2-(5-methyl)-furyl)-4-phenyl-indenyl)hafnium dichloride, dimethylsilylene(2-methyl-4-naphthyl-indenyl)(2-(2-furyl)-4-naphthyl-indenyl)zirconium dichloride, dimethylsilylene(2-methyl-4-naphthyl-indenyl)(2-(2-(5-methyl)-furyl)-4-naphthyl-indenyl)zirconium dichloride, diphenylsilylene(2-methyl-4-naphthyl-indenyl)(2-(2-(5-methyl)-furyl)-4-naphthyl-indenyl)zirconium dichloride, dimethylgermylene(2-methyl-4-naphthyl-indenyl)(2-(2-(5-methyl)-furyl)-4-naphthyl-indenyl)zirconium dichloride, dimethylsilylene(2-methyl-4-naphthyl-indenyl)(2-(2-(5-t-butyl)-furyl)-4-naphthyl-indenyl)zirconium dichloride, dimethylsilylene(2-methyl-4-naphthyl-indenyl)(2-(2-(5-trimethylsilyl)-furyl)-4-naphthyl-indenyl)zirconium dichloride, dimethylsilylene (2-methyl-4-naphthyl-indenyl)(2-(2-(5-methyl)-furyl)-4-naphthyl-indenyl)titanium dichloride, dimethylsilylene(2-methyl-4-naphthyl-indenyl)(2-(2-(5-methyl)-furyl)-4-naphthyl-indenyl)hafnium dichloride, dimethylgermylene(2-methyl-4-naphthyl-indenyl)(2-(2-(5-methyl)-furyl)-4-naphthyl-indenyl)titanium dichloride, dimethylgermylene(2-methyl-4-naphthyl-indenyl)(2-(2-(5-methyl)-furyl)-4-naphthyl-indenyl)hafnium dichloride, dimethylgermylene(2-methyl-4-naphthyl-indenyl)(2-(2-(5-methyl)-furyl)-4-naphthyl-indenyl)zirconium dichloride, dimethylsilylene(2-methyl-4-(4-t-butylphenyl)-indenyl)(2-(2-(5-methyl)-furyl)-4-(4-t-butylphenyl)-indenyl)zirconium dichloride, dimethylsilylene(2-ethyl-4-(4-t-butylphenyl)-indenyl)(2-(2-(5-methyl)-furyl)-4-(4-t-butylphenyl)-indenyl)zirconium dichloride, dimethylsilylene(2-n-propyl-4-(4-t-butylphenyl)-indenyl)(2-(2-(5-methyl)-furyl)-4-(4-t-butylphenyl)-indenyl)zirconium dichloride, dimethylsilylene(2-isopropyl-4-(4-t-butylphenyl)-indenyl)(2-(2-(5-methyl)-furyl)-4-(4-t-butylphenyl)-indenyl)zirconium dichloride, dimethylgermylene(2-methyl-4-(4-t-butylphenyl)-indenyl)(2-(2-(5-methyl)-furyl)-4-(4-t-butylphenyl)-indenyl)zirconium dichloride, dimethylsilylene(2-methyl-4-(4-t-butylphenyl)-indenyl)(2-(2-(5-methyl)-furyl)-4-(4-t-butylphenyl)-indenyl)titanium dichloride, dimethylsilylene(2-methyl-4-(4-t-butylphenyl)-indenyl)(2-(2-(5-methyl)-furyl)-4-(4-t-butylphenyl)-indenyl)hafnium dichloride, dimethylsilylene(2-methyl-4-(3,5-di-t-butylphenyl)-indenyl)(2-(2-(5-methyl)-furyl)-4-(3,5-di-t-butylphenyl)-indenyl)zirconium dichloride, dimethylsilylene(2-methyl-4-(3,5-di-methylphenyl)-indenyl)(2-(2-(5-methyl)-furyl)-4-(3,5-di-methylphenyl)-indenyl)zirconium dichloride, dimethylsilylene(2-methyl-4-(3,5-di-trifluoromethylphenyl)-indenyl)(2-(2-(5-methyl)-furyl)-4-(3,5-di-trifluoromethylphenyl)-indenyl)zirconium dichloride, dimethylsilylene(2-methyl-4-(3,5-di-trimethylsilylphenyl)-indenyl)(2-(2-(5-methyl)-furyl)-4-(3,5-di-trimethylsilylphenyl)-indenyl)zirconium dichloride, dimethylgermylene(2-methyl-4-(3,5-di-t-butylphenyl)-indenyl)(2-(2-(5-methyl)-furyl)-4-(3,5-di-t-butylphenyl)-indenyl)zirconium dichloride, dimethylsilylene(2-methyl-4-(3,5-di-t-butylphenyl)-indenyl)(2-(2-(5-methyl)-furyl)-4-(3,5-di-t-butylphenyl)-indenyl)titanium dichloride, dimethylsilylene(2-methyl-4-(3,5-di-t-butylphenyl)-indenyl)(2-(2-(5-methyl)-furyl)-4-(3,5-di-t-butylphenyl)-indenyl)hafnium dichloride, dimethylsilylene(2-ethyl-4-phenyl-indenyl)(2-(2-(5-methyl)-furyl)-4-phenyl-indenyl)zirconium dichloride, dimethylsilylene(2-n-propyl-4-phenyl-indenyl)(2-(2-(5-methyl)-furyl)-4-phenyl-indenyl)zirconium dichloride, dimethylsilylene(2-isopropyl-4-phenyl-indenyl)(2-(2-(5-methyl)-furyl)-4-phenyl-indenyl)zirconium dichloride, dimethylsilylene(2-n-butyl-4-phenyl-indenyl)(2-(2-(5-methyl)-furyl)-4-phenyl-indenyl)zirconium dichloride, dimethylsilylene(2-t-butyl-4-phenyl-indenyl)(2-(2-(5-methyl)-furyl)-4-phenyl-indenyl)zirconium dichloride, dimethylgermylene(2-ethyl-4-phenyl-indenyl)(2-(2-(5-methyl)-furyl)-4-phenyl-indenyl)zirconium dichloride, dimethylsilylene(2-ethyl-4-phenyl-indenyl)(2-(2-(5-methyl)-furyl)-4-phenyl-indenyl)titanium dichloride, dimethylsilylene(2-ethyl-4-phenyl-indenyl)(2-(2-(5-methyl)-furyl)-4-phenyl-indenyl)hafnium dichloride, dimethylsilylene(2-methyl-indenyl)(2-(2-(5-methyl)-furyl)-indenyl)zirconium dichloride, dimethylsilylene(2-methyl-4-phenyl-indenyl)(2-(2-(5-methyl)-furyl)-indenyl)zirconium dichloride, dimethylsilylene(2-methyl-indenyl)(2-(2-(5-methyl)-furyl)-4-phenylindenyl)zirconium dichloride, dimethylgermylene(2-methyl-indenyl)(2-(2-(5-methyl)-furyl)-indenyl)zirconium dichloride, dimethylsilylene(2-methyl-indenyl)(2-(2-(5-methyl)-furyl)-indenyl)titanium dichloride, dimethylsilylene(2-methyl-indenyl)(2-(2-(5-methyl)-furyl)-indenyl)hafnium dichloride, dimethylsilylene(2-methyl-4-phenyl-indenyl)(2-phenyl-4-phenyl-indenyl)zirconium dichloride, dimethylsilylene(2-methyl-4-phenyl-indenyl)(2-cyclopropyl-4-phenyl-indenyl)zirconium dichloride, dimethylsilylene(2-methyl-4-phenyl-indenyl)(2-cyclohexyl-4-phenyl-indenyl)zirconium dichloride, dimethylsilylene(2-methyl-4-phenyl-indenyl)(2-tolyl-4-phenyl-indenyl)zirconium dichloride, dimethylsilylene(2-methyl-4-phenyl-indenyl)(2-pyrrole-4-phenyl-indenyl)zirconium dichloride, dimethylsilylene(2-methyl-4-phenyl-indenyl)(2-oxazole-4-phenyl-indenyl)zirconium dichloride, dimethylsilylene(2-methyl-4-phenyl-indenyl)(2-thiazole-4-phenyl-indenyl)zirconium dichloride, dimethylsilylene(2-methyl-4-phenyl-indenyl)(2-imidazole-4-phenyl-indenyl)zirconium dichloride, dimethylsilylene(2-methyl-4-phenyl-indenyl)(2-pyrrole-4-phenyl-indenyl)zirconium dichloride, dimethylsilylene(2-methyl-4-phenyl-indenyl)(2-pyrazole-4-phenyl-indenyl)zirconium dichloride, dimethylsilylene(2-methyl-4-phenyl-indenyl)(2-pyrroline-4-phenyl-indenyl)zirconium dichloride, dimethylsilylene(2-methyl-4-phenyl-indenyl)(2-pyrrolidine-4-phenyl-indenyl)zirconium dichloride, dimethylsilylene(2-methyl-4-phenyl-indenyl)(2-pyridine-4-phenyl-indenyl)zirconium dichloride, dimethylsilylene(2-methyl-4-phenyl-indenyl)(2-pyrimidine-4-phenyl-indenyl)zirconium dichloride, dimethylsilylene(2-methyl-4-phenyl-indenyl)(2-purine-4-phenyl-indenyl)zirconium dichloride, dimethylsilylene(2-methyl-4-phenyl-indenyl)(2-quinoline-4-phenyl-indenyl)zirconium dichloride, dimethylsilylene(2-methyl-4-phenyl-indenyl)(2-isoquinoline-4-phenyl-indenyl)zirconium dichloride, dimethylsilylene(2-methyl-4-phenyl-indenyl)(2-carbazole-4-phenyl-indenyl)zirconium dichloride, dimethylgermylene(2-methyl-4-phenyl-indenyl)(2-phenyl-4-phenyl-indenyl)zirconium dichloride, dimethylsilylene(2-methyl-4-phenyl-indenyl)(2-phenyl-4-phenyl-indenyl)titanium dichloride, dimethylsilylene(2-methyl-4-phenyl-indenyl)(2-phenyl-4-phenyl-indenyl)hafnium dichloride, dimethylgermylene(2-methyl-4-phenyl-indenyl)(2-cyclopropyl-4-phenyl-indenyl)zirconium dichloride, dimethylsilylene(2-methyl-4-phenyl-indenyl)(2-cyclopropyl-4-phenyl-indenyl)titanium dichloride, dimethylsilylene(2-methyl-4-phenyl-indenyl)(2-cyclopropyl-4-phenyl-indenyl)hafnium dichloride, etc.

Among those mentioned, preferred are dimethylsilylene(2-methyl-4-phenyl-indenyl)(2-(2-furyl)-4-phenyl-indenyl)zirconium dichloride, dimethylsilylene(2-methyl-4-phenyl-indenyl)(2-(2-(5-methyl)-furyl)-4-phenyl-indenyl)zirconium dichloride, diphenylsilylene(2-methyl-4-phenyl-indenyl)(2-(2-(5-methyl)-furyl)-4-phenyl-indenyl)zirconium dichloride, dimethylgermylene(2-methyl-4-phenyl-indenyl)(2-(2-(5-methyl)-furyl)-4-phenyl-indenyl)zirconium dichloride, dimethylsilylene(2-methyl-4-phenyl-indenyl)(2-(2-(5-t-butyl)-furyl)-4-phenyl-indenyl)zirconium dichloride and dimethylsilylene(2-methyl-4-phenyl-indenyl)(2-(2-(5-trimethylsilyl)-furyl)-4-phenyl-indenyl)zirconium dichloride.

The most preferred is dimethylsilylene(2-methyl-4-phenyl-indenyl)(2-(2-furyl)-4-phenyl-indenyl)zirconium dichloride.

Such metallocene compounds represented by the general formula (2) can be hydrogenated to metallocene compounds having a tetrahydroindenyl skeleton for further use.

Among the metallocene compounds represented by the general formula (1), another preferred embodiment is a metallocene compound represented by the following general formula (3) wherein each of K and L represents an azulenyl group and has $R^4$ or $R^5$ at the 2-position and $R^6$ at the 4-position of the azulenyl group.

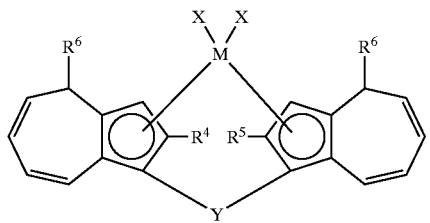
(3)

In the general formula (3), $R^4$ represents an alkyl group of 1–6 carbon atoms, a halogen-containing alkyl group of 1–6 carbon atoms, a silicon-containing alkyl group of 1–6 carbon atoms, an aryl group of 6–16 carbon atoms or a halogen-containing aryl group of 6–16 carbon atoms. $R^4$ is preferably an alkyl group of 1–6 carbon atoms, more preferably a methyl group, an ethyl group, an n-propyl group, an isopropyl group, an n-butyl group or t-butyl, and most preferably, a methyl group.

The aryl group of 6–16 carbon atoms above may optionally be substituted with one or more hydrocarbon groups, silicon-containing hydrocarbon groups, or halogen-containing hydrocarbon groups, each with 1–20 carbon atoms and preferably with 1–6 carbon atoms, or alternatively may be substituted with an alkoxyl group, a dialkyl-substituted amino group, an amino group, a 2-furyl group, a substituted 2-furyl group, a 2-thienyl group, a substituted 2-thienyl group, a 2-furfuryl group, a substituted 2-furfuryl group, a siloxyl group, a $SR^a$ group (S represents a sulfur atom and $R^a$ represents a halogen atom, an alkyl group of 1–10 carbon atoms or an aryl group of 6–16 carbon atoms), or a $PR^b{}_2$ group (P represents a phosphorous atom; and two $R^b$s may be the same or different and each represents a halogen atom, an alkyl group of 1–10 carbon atoms or an aryl group of 6–16 carbon atoms).

In the general formula (3), $R^5$ represents an aryl group of 6–16 carbon atoms, an alkyl group of 2–6 carbon atoms, an alicyclic hydrocarbon group of 3–16 carbon atoms or a heterocyclic group on condition that $R^5$ is different from $R^4$. $R^5$ is preferably an aryl group of 6–16 carbon atoms, an alkyl group of 3–6 carbon atoms, a 2-furyl group, a substituted 2-furyl group, a 2-thienyl group, a substituted 2-thienyl group, a 2-furfuryl group, or a substituted 2-furfuryl group, more preferably a 2-furyl group, a substituted 2-furyl group, a 2-thienyl group, a substituted 2-thienyl group, a 2-furfuryl group, or a substituted 2-furfuryl group, even more preferably, a 2-furyl group or a substituted 2-furyl group, further more preferably a substituted 2-furyl group, and most preferably, a 2-(5-methyl)-furyl group.

In the general formula (3), $R^6$s may be the same or different and each represents a hydrogen atom, an alkyl group of 1–6 carbon atoms, a halogen-containing alkyl group of 1–6 carbon atoms, a silicon-containing alkyl group of 1–6 carbon atoms, an aryl group of 6–16 carbon atoms, a halogen-containing aryl group of 6–16 carbon atoms, a 2-furyl group, a substituted 2-furyl group, a 2-thienyl group, a substituted 2-thienyl group, a 2-furfuryl group or a substituted 2-furfuryl group, preferably an aryl group of 6–16 carbon atoms, a halogen-containing aryl group of 6–16 carbon atoms, a 2-thienyl group or a substituted 2-thienyl group, more preferably an aryl group of 6–16 carbon atoms, a halogen-containing aryl group of 6–16 carbon atoms or a substituted 2-thienyl group, and most preferably, a phenyl group, a naphthyl group, a chlorophenyl group or a fluorophenyl group.

The aryl group of 6–16 carbon atoms above may optionally be substituted with one or more hydrocarbon groups, silicon-containing hydrocarbon groups or halogen-containing hydrocarbon groups, each with 1–20 carbon atoms and preferably with 1–6 carbon atoms, or alternatively may be substituted with an alkoxyl group, a dialkyl-substituted amino group, an amino group, a 2-furyl group, a substituted 2-furyl group, a 2-thienyl group, a substituted 2-thienyl group, a 2-furfuryl group, a substituted 2-furfuryl group, a siloxyl group, a $SR^a$ group (S represents a sulfur atom and $R^a$ represents a halogen atom, an alkyl group of 1–10 carbon atoms or an aryl group of 6–16 carbon atoms), or a $PR^b{}_2$ group (P represents a phosphorous atom; and two $R^b$s may be the same or different and each represents a halogen atom, an alkyl group of 1–10 carbon atoms or an aryl group of 6–16 carbon atoms).

The metallocene compounds represented by the general formula (3) above are preferably those wherein in the general formula (3), $R^4$ represents an alkyl group of 1–6 carbon atoms and $R^5$ represents a 2-furyl group or a substituted 2-furyl group.

The metallocene compounds represented by the general formula (3) above are more preferably those wherein in the general formula (3); $R^4$ represents an alkyl group of 1–6 carbon atoms; $R^5$ represents a 2-furyl group or a substituted 2-furyl group; and two $R^6$s may be the same or different and each represents an aryl group of 6–16 carbon atoms or a halogen-containing aryl group of 6–16 carbon atoms.

Particularly, such metallocene compounds represented by the general formula (3) are preferably used as catalytic components with high polymerization activity for olefin polymerization to produce olefin polymers having high molecular weight and high stereoregularity. Particularly, such metallocene compounds are preferably used as catalytic components for olefin polymerization to carry out the copolymerization of propylene with an olefin other than propylene and to produce a propylene/olefin copolymer such that the molecular weight of the obtained propylene/olefin copolymer has either hardly decreased or has experienced only a small decrease and is similar to or higher than the molecular weight of propylene homopolymer produced under the same conditions even if the content of the olefin unit other than propylene has increased. Another characteristic feature is that when the propylene/ethylene copolymerization is carried out, the melting point of the obtained propylene/ethylene copolymer decreases very efficiently as the ethylene content increases. The reason is not clear, but it is presumably due to the fact that the ethylene units have been inserted into the copolymer in a highly random manner. In these cases, the olefin other than propylene is preferably ethylene or 1-butene, or ethylene and 1-butene. Ethylene is most preferred among those.

Specific examples of such metallocene compounds include: dimethylsilylene(2-methyl-4-phenyl-4-hydroazulenyl)(2-(2-(5-methyl)-furyl)-4-phenyl-4-hydroazulenyl)zirconium dichloride, dimethylsilylene(2-ethyl-4-phenyl-4-hydroazulenyl)(2-(2-(5-methyl)-furyl)-4-phenyl-hydroazulenyl)zirconium dichloride, dimethylsilylene(2-methyl-4-(2-(5-methyl)-thienyl-4-hydroazulenyl)(2-(2-(5-methyl)-furyl)-4-phenyl-4 -hydroazulenyl)zirconium dichloride, dimethylsilylene(2-methyl-4-(2-(5-methyl)-thienyl-4-hydroazulenyl)(2-(2-(5-methyl)-furyl)-4-(2-(5-methyl)-thienyl-4-hydroazulenyl)zirconium dichloride, dimethylsilylene(2-methyl-4-phenyl-4-hydroazulenyl)(2-(2-(5- methyl)-furyl)-4-(2-(5-methyl)-thienyl)-4-hydroazulenyl) zirconium dichloride, dimethylgermylene(2-methyl-4-phenyl-4-hydroazulenyl)(2-(2-(5-methyl)-furyl)-4-phenyl-4-hydroazulenyl)zirconium dichloride, dimethylsilylene(2-methyl-4-phenyl-4-hydroazulenyl)(2-(2-(5-methyl)-furyl)-4-phenyl-4-hydroazulenyl)titanium dichloride, dimethylsilylene(2-methyl-4-phenyl-4-hydroazulenyl)(2-(2-(5-methyl)-furyl)-4-phenyl-4-hydroazulenyl)hafnium dichloride, dimethylsilylene(2-methyl-4-phenyl-4-hydroazulenyl)(2-phenyl-4-phenyl-4-hydroazulenyl)zirconium dichloride, dimethylsilylene(2-methyl-4-phenyl-4-hydroazulenyl)(2-n-butyl-4-phenyl-4-hydroazulenyl)zirconium dichloride, dimethylsilylene(2-methyl-4-phenyl-4-hydroazulenyl)(2-cyclohexyl-4-phenyl-4-hydroazulenyl)zirconium dichloride, dimethylsilylene(2-methyl-4-phenyl-4-hydroazulenyl)(2-isopropyl-4-phenyl-4-hydroazulenyl)zirconium dichloride, dimethylgermylene(2-methyl-4-phenyl-4-hydroazulenyl)(2-phenyl-4-phenyl-4-hydroazulenyl)zirconium dichloride, dimethylsilylene(2-methyl-4-phenyl-4-hydroazulenyl)(2-phenyl-4-phenyl-4-hydroazulenyl)titanium dichloride, dimethylsilylene(2-methyl-4-phenyl-4-hydroazulenyl)(2-phenyl-4-phenyl-4-hydroazulenyl)hafnium dichloride, etc.

Among those mentioned, preferred are dimethylsilylene (2-methyl-4-phenyl-4-hydroazulenyl)(2-(2-(5-methyl)-furyl)-4-phenyl-4-hydroazulenyl)zirconium dichloride, dimethylsilylene(2-ethyl-4-phenyl-4-hydroazulenyl)(2-(2-(5-methyl)-furyl)-4-phenyl-4-hydroazulenyl)zirconium dichloride, dimethylsilylene(2-methyl-4-(2-(5-methyl)-thienyl)-4-hydroazulenyl)(2-(2-(5-methyl)-furyl)-4-phenyl-4-hydroazulenyl)zirconium dichloride, dimethylsilylene(2-methyl-4-(2-(5-methyl)-thienyl)-4-hydroazulenyl)(2-(2-(5-methyl)-furyl)-4-(2-(5-methyl)-thienyl)-4-hydroazulenyl) zirconium dichloride, dimethylsilylene(2-methyl-4-phenyl-4-hydroazulenyl)(2-(2-(5-methyl)-furyl)-4-(2-(5-methyl)-thienyl)-4-hydroazulenyl)zirconium dichloride; and the most preferred is dimethylsilylene(2-methyl-4-phenyl-4-hydroazulenyl)(2-(2-(5-methyl)-furyl)-4-phenyl-4-hydroazulenyl)zirconium dichloride.

Such metallocene compounds represented by the general formula (3) can be hydrogenated to metallocene compounds having a tetrahydroindenyl skeleton for further use.

Among the metallocene compounds represented by the general formula (1), another preferred embodiment is a metallocene compound represented by the following general formula (4) wherein each of K and L represents an azulenyl group and has $R^7$ at the 2-position and $R^8$ or $R^9$ at the 4-position of the azulenyl group.

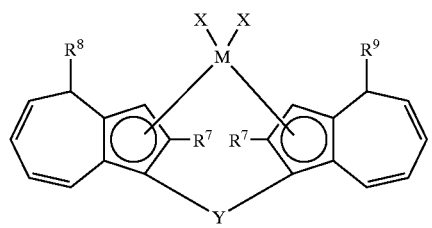

(4)

In the general formula (4), two $R^7$s may be the same or different and each represents an alkyl group of 1–6 carbon atoms, a halogen-containing alkyl group of 1–6 carbon atoms, a silicon-containing alkyl group of 1–6 carbon atoms, an aryl group of 6–16 carbon atoms or a halogen-containing aryl of 6–16 carbon atoms, preferably an alkyl group of 1–6 carbon atoms, more preferably a methyl group, an ethyl group, a n-propyl group, an isopropyl group, a n-butyl group or a t-butyl group, and most preferably, a methyl group.

The aryl group of 6–16 carbon atoms above may optionally be substituted with one or more hydrocarbon groups, silicon-containing hydrocarbon groups or halogen-containing hydrocarbon groups, each with 1–20 carbon atoms and preferably with 1–6 carbon atoms, or alternatively may be substituted with an alkoxyl group, a dialkyl-substituted amino group, an amino group, a 2-furyl group, a substituted 2-furyl group, a 2-thienyl group, a substituted 2-thienyl group, a 2-furfuryl group, a substituted 2-furfuryl group, a siloxyl group, a $SR^a$ group (S represents a sulfur atom and $R^a$ represents a halogen atom, an alkyl group of 1–10 carbon atoms or an aryl group of 6–16 carbon atoms), a $PR^b{}_2$ group (P represents a phosphorous atom; and two $R^b$s may be the same or different and each represents a halogen atom, an alkyl group of 1–10 carbon atoms or an aryl group of 6–16 carbon atoms).

In the general formula (4), $R^8$ is an alkyl group of 1–6 carbon atoms, a halogen-containing alkyl group of 1–6 carbon atoms, a silicon-containing alkyl group of 1–6 carbon atoms, an aryl group of 6–16 carbon atoms, a halogen-containing aryl group of 6–16 carbon atoms, preferably an aryl group of 6–16 carbon atoms or a halogen-containing aryl group of 6–16 carbon atoms, more preferably a phenyl group, a chlorophenyl group, a fluorophenyl group or a naphthyl group, and most preferably a phenyl group.

The aryl group of 6–16 carbon atoms above may optionally be substituted with one or more hydrocarbon groups, silicon-containing hydrocarbon groups, or halogen-containing hydrocarbon groups, each with 1–20 carbon atoms and preferably with 1–6 carbon atoms, or alternatively may be substituted with an alkoxyl group, a dialkyl-substituted amino group, an amino group, a 2-furyl group, a substituted 2-furyl group, a 2-thienyl group, a substituted 2-thienyl group, a 2-furfuryl group, a substituted 2-furfuryl group, a siloxyl group, a $SR^a$ group (S represents a sulfur atom and $R^a$ represents a halogen atom, an alkyl group of 1–10 carbon atoms or an aryl group of 6–16 carbon atoms), a $PR^b{}_2$ group (P represents a phosphorous atom; and two $R^b$s may be the same or different and each represents a halogen atom, an alkyl group of 1–10 carbon atoms or an aryl group of 6–16 carbon atoms).

In the general formula (4), $R^9$ represents an aryl group of 6–16 carbon atoms, an alkyl group of 2–6 carbon atoms, an alicyclic hydrocarbon group of 3–16 carbon atoms or a heterocyclic group on condition that $R^9$ is different from $R^8$. $R^9$ is preferably a 2-furyl group, a substituted 2-furyl group, a 2-thienyl group, a substituted 2-thienyl group, a 2-furfuryl group or a substituted 2-furfuryl group, more preferably a 2-thienyl group, or a substituted 2-thienyl group, even more preferably, a substituted 2-thienyl group, and most preferably, a 2-(5-methyl)-thienyl group.

The metallocene compounds represented by the general formula (4) are preferably those wherein in the general formula (4), two $R^7$s may be the same or different and each represents an alkyl group of 1–6 carbon atoms; $R^8$ represents an aryl group of 6–16 carbon atoms or a halogen-containing aryl group of 6–16 carbon atoms; and $R^9$ represents a 2-thienyl group or a substituted 2-thienyl group.

Particularly, such metallocene compounds represented by the general formula (4) are preferably used as catalytic components with high polymerization activity for olefin polymerization to produce olefin polymers having high molecular weight and high stereoregularity. Particularly, such metallocene compounds are also preferably used as catalytic components for olefin polymerization to carry out the copolymerization of propylene with an olefin other than propylene and to produce a propylene/olefin copolymer such that the molecular weight of the obtained propylene/olefin copolymer has either hardly decreased or has experienced only a small decrease and is similar to or higher than the molecular weight of propylene homopolymer produced under the same conditions even if the content of the olefin unit other than propylene has increased. Another characteristic feature is that when the propylene/ethylene copolymerization is carried out, the melting point of the obtained propylene/ethylene copolymer decreases very efficiently as the ethylene content increases. The reason is not clear, but it is presumably due to the fact that the ethylene units have been inserted into the copolymer in a highly random manner. In these cases, the olefin other than propylene is preferably ethylene or 1-butene, or ethylene and 1-butene. Ethylene is most preferred among those.

Specific examples of such metallocene compounds include: dimethylsilylene(2-methyl-4-phenyl-4-hydroazulenyl)(2-methyl-4-(2-(5-methyl)-thienyl)-4-hydroazulenyl) zirconium dichloride, dimethylsilylene(2-methyl-4-phenyl-4-hydroazulenyl)(2-methyl-4-(2-(5-phenyl)-thienyl)-4-hydroazulenyl)zirconium dichloride, dimethylsilylene(2-methyl-4-phenyl-4-hydroazulenyl)(2-methyl-4(2-(5-trimethylsilyl)-thienyl)-4-hydroazulenyl)zirconium dichloride, dimethylsilylene(2-methyl-4-phenyl-4-hydroazulenyl)(2-methyl-4-(2-(5-t-butyl)-thienyl)-4-hydroazulenyl)zirconium dichloride, dimethylsilylene(2-ethyl-4-phenyl-4-hydroazulenyl)(2-ethyl-4-(2-(5-methyl)-thienyl)-4-hydroazulenyl)zirconium dichloride, dimethylgermylene(2-methyl-4-phenyl-4-hydroazulenyl)(2-methyl-4-(2-(5-methyl)-thienyl)-4-hydroazulenyl)zirconium dichloride, dimethylsilylene(2-methyl-4-phenyl-4-hydroazulenyl)(2-methyl-4-(2-(5-methyl)-thienyl)-4-hydroazulenyl)titanium dichloride, dimethylsilylene(2-methyl-4-phenyl-4-hydroazulenyl)(2-methyl-4-(2-(5-methyl)-thienyl)-4-hydroazulenyl)hafnium dichloride, dimethylsilylene(2-methyl-4-phenyl-4-hydroazulenyl)(2-methyl-4-(4-t-Bu-phenyl)-4-hydroazulenyl)zirconium dichloride, and dimethylsilylene (2-methyl-4-phenyl-4-hydroazulenyl)(2-methyl-4-(4-chlorophenyl)-4-hydroazulenyl)zirconium dichloride.

Among those mentioned, preferred are dimethylsilylene (2-methyl-4-phenyl-4-hydroazulenyl)(2-methyl-4-(2-(5-methyl)-thienyl)-4-hydroazulenyl)zirconium dichloride, dimethylsilylene(2-methyl-4-phenyl-4-hydroazulenyl)(2-methyl-4-(2-(5-phenyl)-thienyl)-4-hydroazulenyl)zirconium dichloride, dimethylsilylene(2-methyl-4-phenyl-4-hydroazulenyl)(2-methyl-4-(2-(5 -trimethylsilyl)-thienyl)-4-hydroazulenyl)zirconium dichloride, dimethylsilylene(2-methyl-4-phenyl-4-hydroazulenyl)(2-methyl-4-(2-(5-t-butyl)-thienyl)-4-hydroazulenyl)zirconium dichloride, dimethylsilylene(2-ethyl-4-phenyl-4-hydroazulenyl)(2-ethyl-4-(2-(5-methyl)-thienyl)-4-hydroazulenyl)zirconium dichloride; and the most preferred is dimethylsilylene(2-methyl-4-phenyl-4-hydroazulenyl)(2-methyl-4-(2-(5-methyl)-thienyl)-4-hydroazulenyl)zirconium dichloride.

Such metallocene compounds represented by the general formula (4) can be hydrogenated to metallocene compounds having a tetrahydroindenyl skeleton for further use.

Among the metallocene compounds represented by the general formula (1), another preferred embodiment is a metallocene compound represented by the following general formula (5) wherein each of K and L represents an benzoindenyl group and has $R^{10}$ or $R^{11}$ at the 2-position of the benzoindenyl group.

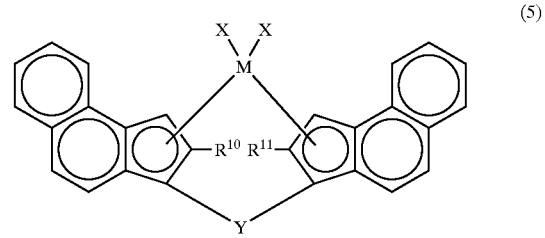

(5)

In the general formula (5), $R^{10}$ is an alkyl group of 1–6 carbon atoms, a halogen-containing alkyl group of 1–6 carbon atoms, a silicon-containing alkyl group of 1–6 carbon atoms, an aryl group of 6–16 carbon atoms, or a halogen-containing aryl group of 6–16 carbon atoms, preferably an alkyl group of 1–6 carbon atoms, a halogen-containing alkyl group of 1–6 carbon atoms, a silicon-containing alkyl group of 1–6 carbon atoms, an aryl group of 6–16 carbon atoms or a halogen-containing aryl group of 6–16 carbon atoms, more preferably an alkyl group of 1–6 carbon atoms, even more preferably a methyl group, an ethyl group, a n-propyl group, an isopropyl group, a n-butyl group or a t-butyl group, and most preferably, a methyl group.

The aryl group of 6–16 carbon atoms above may optionally be substituted with one or more hydrocarbon groups, silicon-containing hydrocarbon groups, or halogen-containing hydrocarbon groups, each with 1–20 carbon atoms and preferably with 1–6 carbon atoms, or alternatively may be substituted with an alkoxyl group, a dialkyl-substituted amino group, an amino group, a 2-furyl group, a substituted 2-furyl group, a 2-thienyl group, a substituted 2-thienyl group, a 2-furfuryl group, a substituted 2-furfuryl group, a siloxyl group, a $SR^a$ group (S represents a sulfur atom and $R^a$ represents a halogen atom, an alkyl group of 1–10 carbon atoms or an aryl group of 6–16 carbon atoms), a $PR^b{}_2$ group (P represents a phosphorous atom; and two $R^b$s may be the same or different and each represents a halogen atom, an alkyl group of 1–10 carbon atoms or an aryl group of 6–16 carbon atoms).

$R^{11}$ represents an aryl group of 6–16 carbon atoms, an alkyl group of 2–6 carbon atoms, an alicyclic hydrocarbon group of 3–16 carbon atoms or a heterocyclic group on condition that $R^{11}$ is different from $R^{10}$. $R^{11}$ is preferably an aryl group of 6–16 carbon atoms, an alkyl group of 3–6 carbon atoms, a 2-furyl group, a substituted 2-furyl group, a 2-thienyl group, a substituted 2-thienyl group, a 2-furfuryl group or a substituted 2-furfuryl group, more preferably 2-furyl group, a substituted 2-furyl group, a 2-thienyl group or a substituted 2-thienyl group, even more preferably, a 2-furyl group or a substituted 2-furyl group, further more preferably a substituted 2-furyl group, and most preferably, a 2-(5-methyl)-furyl group.

Particularly, such metallocene compounds represented by the general formula (5) are preferably used as catalytic components with high polymerization activity for olefin polymerization to produce olefin polymers having high molecular weight and high stereoregularity. Particularly, such metallocene compounds are also preferably used as catalytic components for olefin polymerization to carry out the copolymerization of propylene with an olefin other than propylene and to produce a propylene/olefin copolymer such that the molecular weight of the obtained propylene/olefin copolymer has either hardly decreased or has experienced only a small decrease and is similar to or higher than the molecular weight of propylene homopolymer produced under the same conditions even if the content of the olefin unit other than propylene has increased. Another characteristic feature is that when the propylene/ethylene copolymerization is carried out, the melting point of the obtained propylene/ethylene copolymer decreases very efficiently as the ethylene content increases. The reason is not clear, but it is presumably due to the fact that the ethylene units have been inserted into the copolymer in a highly random manner. In these cases, the olefin other than propylene is preferably ethylene or 1-butene, or ethylene and 1-butene. Ethylene is most preferred among those.

Specific examples of such metallocene compounds include: dimethylsilylene(2-methyl-benzoindenyl)(2-(2-(5-methyl)-furyl)-benzoindenyl)zirconium dichloride, dimethylsilylene(2-ethyl-benzoindenyl)(2-(2-(5-methyl)-furyl)-benzoindenyl)zirconium dichloride, dimethylsilylene(2-methyl-benzoindenyl)(2-(2-(5-phenyl)-furyl)-benzoindenyl)zirconium dichloride, dimethylsilylene(2-methyl-benzoindenyl)(2-(2-(5-t-butyl)-furyl)-benzoindenyl)zirconium dichloride, dimethylsilylene(2-methyl-benzoindenyl)(2-(2-(5-trimethylsilyl)-furyl)-benzoindenyl)zirconium dichloride, dimethylgermylene(2-methyl-benzoindenyl)(2-(2-(5-methyl)-furyl)-benzoindenyl)zirconium dichloride, dimethylsilylene(2-methyl-benzoindenyl)(2-(2-(5-methyl)-furyl)-benzoindenyl)titanium dichloride, dimethylsilylene(2 -methyl-benzoindenyl)(2-(2-(5-methyl)-furyl)-benzoindenyl)hafnium dichloride, dimethylsilylene(2-methyl-benzoindenyl)(2-phenyl-benzoindenyl)zirconium dichloride, dimethylsilylene(2-methyl-benzoindenyl)(2-n-butyl-benzoindenyl)zirconium dichloride, dimethylsilylene (2-methyl-benzoindenyl)(2-cyclohexyl-benzoindenyl)zirconium dichloride, dimethylgermylene(2-methyl-benzoindenyl)(2-phenyl-benzoindenyl)zirconium dichloride, dimethylsilylene(2-methyl-benzoindenyl)(2-phenyl-benzoindenyl)titanium dichloride, and dimethylsilylene(2-methyl-benzoindenyl)(2-phenyl-benzoindenyl) hafnium dichloride.

Among those mentioned, preferred are dimethylsilylene (2-methyl-benzoindenyl)(2-(2-(5-methyl)-furyl)-benzoindenyl)zirconium dichloride, dimethylsilylene(2-ethyl-benzoindenyl)(2-(2-(5-methyl)-furyl)-benzoindenyl)zirconium dichloride, dimethylsilylene(2-methyl-benzoindenyl)(2-(2-(5-phenyl)-furyl)-benzoindenyl)zirconium dichloride, dimethylsilylene(2-methyl-benzoindenyl)(2-(2-(5-t-butyl)-furyl)-benzoindenyl)zirconium dichloride, dimethylsilylene (2-methyl-benzoindenyl)(2-(2-(5-trimethylsilyl)-furyl)-benzoindenyl)zirconium dichloride; and the most preferred is dimethylsilylene(2-methyl-benzoindenyl)(2-(2-(5-methyl)-furyl)-benzoindenyl)zirconium dichloride.

Among the metallocene compounds represented by the general formula (1), another preferred embodiment is a metallocene compound represented by the following general formula (6) wherein each of K and L represents an indenyl group and has $R^{12}$ or $R^{13}$ at the 2-position and $R^{14}$ at the 4-position of the indenyl group.

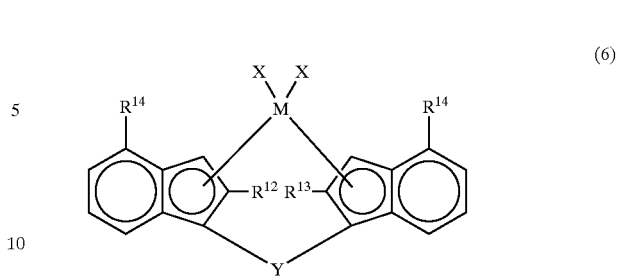

(6)

In the general formula, $R^{12}$ is an alkyl group of 1–3 carbon atoms, preferably a methyl group or an ethyl group, and most preferably, a methyl group. $R^{13}$ is an alkyl group of 2–3 carbon atoms, preferably an ethyl group, a n-propyl group, an isopropyl group, and most preferably, an isopropyl group provided that $R^{12}$ and $R^{13}$ are always different. Two $R^{14}$s may be the same or different and each represents an aryl group of 6–16 carbon atoms, a halogen-containing aryl group of 6–16 carbon atoms, a 2-furyl group, a substituted 2-furyl group, a 2-thienyl group, a substituted 2-thienyl group, a 2-furfuryl group or a substituted 2-furfuryl group, preferably a 2-furyl group, a substituted 2-furyl group, a 2-thienyl group or a substituted 2-thienyl group, more preferably, a 2-thienyl group or a substituted 2-thienyl group, with the proviso that the two $R^{14}$ cannot be either an aryl group of 6–16 carbon atoms or a halogen-containing aryl group of 6–16 carbon atoms at the same time.

Particularly, such metallocene compounds represented by the general formula (6) are preferably used as catalytic components with high polymerization activity for olefin polymerization to produce olefin polymers having high molecular weight and high stereoregularity. Particularly, such metallocene compounds are also preferably used as catalytic components for olefin polymerization to carry out the copolymerization of propylene with an olefin other than propylene and to produce a propylene/olefin copolymer such that the molecular weight of the obtained propylene/olefin copolymer has either hardly decreased or has experienced only a small decrease and is similar to or higher than the molecular weight of propylene homopolymer produced under the same conditions even if the content of the olefin unit other than propylene has increased. Another characteristic feature is that when the propylene/ethylene copolymerization is carried out, the melting point of the obtained propylene/ethylene copolymer decreases very efficiently as the ethylene content increases. The reason is not clear, but it is presumably due to the fact that the ethylene units have been inserted into the copolymer in a highly random manner. In these cases, the olefin other than propylene is preferably ethylene or 1-butene, or ethylene and 1-butene. Ethylene is most preferred among those.

Specific examples of such metallocene compounds include: dimethylsilylene(2-methyl-4-(2-thienyl)-indenyl)(2-isopropyl-4-(2-thienyl)-indenyl)zirconium dichloride, dimethylsilylene(2-methyl-4-(2-(5-methyl)-thienyl-indenyl) (2-isopropyl-4-(2-(5-methyl)-thienyl)-indenyl)zirconium dichloride, dimethylsilylene(2-methyl-4-(2-(5-t-butyl)-thienyl)-indenyl)(2-isopropyl-4-(2-(5-t-butyl)-thienyl)-indenyl) zirconium dichloride.

Such metallocene compounds represented by the general formula (6) can be hydrogenated to metallocene compounds having a tetrahydroindenyl skeleton for further use.

Among the metallocene compounds of this invention, the most preferred are the metallocene compounds represented by the general formula (2) wherein $R^1$ is an alkyl group of 1–6 carbon atoms, a halogen-containing alkyl group of 1–6 carbon atoms, a silicon-containing alkyl group of 1–6 carbon atoms, an aryl group of 6–16 carbon atoms or a halogen-containing aryl group of 6–16 carbon atoms, preferably an alkyl group of 1–6 carbon atoms, more preferably a methyl group, an ethyl group, a n-propyl group, an isopropyl group, a n-butyl group or a t-butyl group, and most preferably, a methyl group or an ethyl group; $R^2$ is a 2-furyl group, a substituted 2-furyl group, a 2-thienyl group, a substituted 2-thienyl group, a 2-furfuryl group or a substituted 2-furfuryl group, preferably a 2-furyl group or a substituted 2-furyl group, more preferably, a substituted 2-furyl group, and most preferably, a 2-(5-methyl)-furyl group; and two $R^3$s may be the same or different and each represents a hydrogen atom, an alkyl group of 1–6 carbon atoms, a halogen-containing alkyl group of 1–6 carbon atoms, a silicon-containing alkyl group of 1–6 carbon atoms, an aryl group of 6–16 carbon atoms, a halogen-containing aryl group of 6–16 carbon atoms, a 2-furyl group, a substituted 2-furyl group, a 2-thienyl group, a substituted 2-thienyl group, a 2-furfuryl group or a substituted 2-furfuryl group, preferably an alkyl group of 1–6 carbon atoms, an aryl group of 6–16 carbon atoms, a halogen-containing aryl group of 6–16 carbon atoms, a 2-thienyl group or a substituted 2-thienyl group, more preferably an aryl group of 6–16 carbon atoms, a halogen-containing aryl group of 6–16 carbon atoms or a substituted 2-thienyl group, and most preferably, a phenyl group, a naphthyl group, a chlorophenyl group or a fluorophenyl group.

The aryl group of 6–16 carbon atoms above may optionally be substituted with one or more hydrocarbon groups, silicon-containing hydrocarbon groups, or halogen-containing hydrocarbon groups, each with 1–20 carbon atoms and preferably with 1–6 carbon atoms, or alternatively may be substituted with an alkoxyl group, a dialkyl-substituted amino group, an amino group, a 2-furyl group, a substituted 2-furyl group, a 2-thienyl group, a substituted 2-thienyl group, a 2-furfuryl group, a substituted 2-furfuryl group, a siloxyl group, a $SR^a$ group (S represents a sulfur atom and $R^a$ represents a halogen atom, an alkyl group of 1–10 carbon atoms or an aryl group of 6–16 carbon atoms), a $PR^b_2$ group (P represents a phosphorous atom; and two $R^b$s may be the same or different and each represents a halogen atom, an alkyl group of 1–10 carbon atoms or an aryl group of 6–16 carbon atoms).

The metallocene compounds of this invention have specific stereostructures in combination with the types of substituents and their positions of substitution. Preferred are the metallocene compounds wherein specifically selected substituents are introduced to the specific positions of ligands having a particular conjugated 5-membered ring skeleton. The process for the preparation of the ligand having a conjugated 5-membered ring skeleton is known in the art. The introduction of substituents may be carried out according to conventional methods.

The metallocene compound of this invention can be reacted with a reagent EY as described in JP-A-2002-509936 (paragraphs [0015]–[0026]) and can be used in the form with the substituents ionized. As used herein, "E" and "Y" that form the reagent EY are as defined below.

E represents a hydrogen atom, an alkyl group of 1–20 carbon atoms, an aryl group of 6–14 carbon atoms, an alkenyl group of 2–20 carbons, a trialkylsilyl group, an alkynyl group of 2–20 carbon atoms or any of an alkylaryl group of 7–20 carbon atoms, an alkylsilyl group of 7–20 carbon atoms, a trialkylsilyl group of 7–20 carbon atoms, and an alkylarylsilyl group of 7–20 carbon atoms and is optionally substituted. Preferable examples of E for use include a hydrogen atom, methyl, ethyl, propyl, butyl, allyl, benzyl, methoxymethyl, benzyloxymethyl, 2-methoxyethoxymethyl, 2-trimethylsilylethoxymethyl and trimethylsilyl.

Y represents a halogen atom, alkylsulfonate of 1–10 carbon atoms, haloalkylsulfonate of 1–20 carbon atoms, arylsulfonate of 6–20 carbon atoms, alkylarylsulfonate of 7–20 carbon atoms, haloalkylcarboxylate of 1–20 carbon atoms, alkylsulfate of 1–10 carbon atoms, tetrafluoroborate, hexafluorophosphate, hexafluoroantimonate or hexafluoroarsenate. Preferably, Y is chlorine, bromine, iodine, trifluorate, mesylate, tosylbenzenesulfonate, trifluoroacetate, methylsulfate, tetrafluoroborate or hexafluorophosphate.

The metallocene compound of this invention can be used with other components as an olefin polymerization catalyst. The catalysts containing the metallocene compounds according to this invention can be broadly classified into the following three types (1)–(3).

(1) The olefin polymerization catalyst (hereinafter referred to as "homogeneous metallocene catalyst" occasionally) comprising a metallocene compound mentioned above (hereinafter referred to as "component (A)" occasionally), an activating compound (hereinafter referred to as "component (B)" occasionally) and, optionally, an organoaluminum compound (hereinafter referred to as "component (D)" occasionally).

(2) The olefin polymerization catalyst comprising a supported metallocene catalyst (hereinafter referred to as "supported metallocene catalyst I" occasionally) produced from component (A), component (B), a support in the form of fine particles (hereinafter referred to as "component (C)" occasionally) and, optionally, component (D), and an organoaluminum compound (hereinafter referred to as "component (D')" occasionally).

(3) The olefin polymerization catalyst comprising a supported metallocene catalyst (hereinafter referred to as "supported metallocene catalyst II" occasionally) produced from component (A), a specific ion-exchangeable layer compound or an inorganic silicate (hereinafter referred to as "component (E)" occasionally) and, optionally, component (D), and component (D').

Between the supported metallocene catalysts I and the supported metallocene catalyst II as described in (2) and (3), the supported metallocene catalyst I as described in (2) is preferably used in the production of an olefin polymer of this invention. Especially, in the case where the metallocene compound of general formula (3) or (4) is used as metallocene compound (A), the supported metallocene catalyst I is preferable.

As component (B) mentioned above, an organoaluminum oxy compound or a compound which reacts with component (A) to form an ion pair is used. As the organoaluminum oxy compound mentioned above, an aluminoxane represented by the following general formula (17) or (18) may be used.

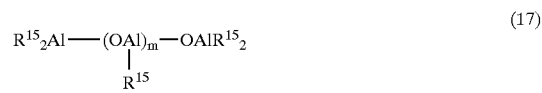

(17)

-continued

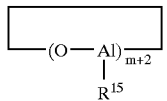
(18)

In the formulae (17) and (18), $R^{15}$ represents a hydrocarbon group of 1–6 carbon atoms. Specific examples of this hydrocarbon group include alkyl groups such as a methyl group, an ethyl group, a propyl group, a butyl group, an isobutyl group, a pentyl group and a hexyl group; alkenyl groups such as an allyl group, a 2-methylallyl group, a propenyl group, an isopropenyl group, a 2-methyl-1-propneyl group and butenyl group; cycloalkyl groups such as a cyclopropyl group, a cyclobutyl group, a cyclopentyl group and a cyclohexyl group; and an aryl group. Among those mentioned, hydrocarbon groups of 1–4 carbon atoms are preferable, and the alkyl group is particularly preferable as the hydrocarbon group. Respective $R^{15}$s may be the same or different. m represents an integer in the range of 4–30, preferably 6–30, and most preferably 8–30.

The aluminoxane mentioned above can be prepared under various known conditions. Specific examples of the method for the preparation are the following (a)–(f).

(a) Method of reacting a trialkyl aluminum with water in an organic solvent such as toluene and ether.

(b) Method of reacting a trialkyl aluminum with a salt which has crystallization water such as copper sulfate hydrate and aluminum sulfate hydrate.

(c) Method of reacting a trialkyl aluminum with the water absorbed on silica gel, etc.

(d) Method of reacting a mixture of trimethyl aluminum and triisobutyl aluminum with water in an organic solvent such as toluene and ether.

(e) Method of reacting a mixture of trimethyl aluminum and triisobutyl aluminum with a salt which has crystallization water such as copper sulfate hydrate and aluminum sulfate hydrate.

(f) Method which comprises reacting the water absorbed on silica gel, etc. with triisobutyl aluminum and subsequently reacting the product with trimethyl aluminum.

Specific examples of the compound which reacts with component (A) to form an ion pair include a Lewis acid, an ionic compound, a borane compound and a carborane compound, which are reported in JP-A-01-501950T, JP-A-01-502036T, JP-A-03-179005, JP-A-03-179006, JP-A-03-207704, WO 92/00333A, U.S. Pat. No. 5,064,802, WO93/03067A, JP-A-04-309508, JP-A-04-353502, JP-A-05-331232 and WO96/41808A. The pertinent parts of the descriptions of the above literatures are incorporated herein by reference.

The Lewis acid preferably contains a boron atom. Non-limiting specific examples of the Lewis acid include trifluoroboron, triphenylboron, tris(4-fluorophenyl)boron, tris(3,5-fluorophenyl)boron, tris(4-fluoromethylphenyl)boron, tris(p-tolyl)boron, tris(o-tolyl)boron, tris(3,5-dimethylphenyl)boron and tris(pentafluorophenyl)boron. Tris(pentafluorophenyl)boron is particularly preferable.

The ionic compound is a salt of cationic and anionic compounds. The anionic compound has an action to cationize the metallocene compound by reaction therewith and to stabilize the transition metal cation species by the formation of an ion pair. Such anionic compounds include anions of organoboron compounds, organoarsenic compounds and organoaluminum compounds, and preferred are anions which are comparatively bulky and can stabilize the transition metal cation. The cationic compounds include metallic cations, organometallic cations, carbonium cations, tropium cations, oxonium cations, sulfonium cations, phosphonium cations and ammonium cations. Specific examples of the cationic compound include triphenyl carbenium cation, tributyl ammonium cation, N,N-dimethylammonium cation and ferrocenium cation.

A salt containing a boron compound as an anionic compound can be preferably used as an ionic compound. Specific examples of the trialkyl-substituted ammonium salt include triethylammonium tetra(phenyl)boron, tripropylammonium tetra(phenyl)boron, tri(n-butyl)ammonium tetra(phenyl)boron, trimethylammonium(p-tolyl)boron, trimethylammonium(o-tolyl)boron, tributylammonium tetra(pentafluorophenyl)boron, tripropylammonium tetra(o,p-dimethylphenyl)boron, tributylammonium tetra(m,m-dimethylphenyl)boron, tributylammonium tetra(p-trifluoromethylphenyl)boron, tri(n-butyl)ammonium tetra(o-tolyl)boron and tri(n-butyl)ammonium tetra(4-fluorophenyl)boron.

Specific examples of the N—N-dialkylanilinium salt include N,N-dimethylanilinium tetra(phenyl)boron, N,N-diethylanilinium tetra(phenyl)boron and N,N,N-2,4,6-pentamethylanilinium(phenyl)boron. Specific examples of the dialkylammonium salt include di(n-propyl)ammonium tetra(pentafluorophenyl)boron and dicyclohexylammonium tetra(pentafluorophenyl)boron. Specific examples of the trialkylphosphonium salt and the triarylphosphonium salt include trimethylphosphonium tetra(phenyl)boron, tri(methylphenyl)phosphonium tetra(phenyl)boron and tri(dimethylphenyl)phosphonium tetra(phenyl)boron.

The ionic compounds containing a boron atom used in this invention include triphenylcarbenium tetrakis(pentafluorophenyl)borate, N,N-dimethylanilinium tetrakis(pentafluorophenyl)borate, and ferrocenium tetra(pentafluorophenyl)borate, for example. Among the above activating compounds, aluminoxane is particularly preferably used.

The component (C) used for producing the supported metallocene catalyst I of this invention is an inorganic support or an organic support. The inorganic or organic support preferably used is in the form of fine granular or spherical solid particles having a diameter in the range of 1–500 µm, preferably in the range of 5–300 µm, more preferably in the range of 10–150 µm and most preferably 10–45 µm.

The finely particulate inorganic support has a specific surface area in the range of 50–1,000 m²/g, preferably in the range of 100–700 m²/g, and a pore volume preferably in the range of 0.3–2.5 m³/g.

The finely particulate inorganic supports are preferably metal oxides such as $SiO_2$, $Al_2O_3$, MgO, $TiO_2$, ZnO, or a mixture thereof, and complex oxides thereof. The supports containing $SiO_2$ or $Al_2O_3$ as main components are particularly preferable. Specific examples of the inorganic compound include $SiO_2$, $Al_2O_3$, MgO, $SiO_2$—$Al_2O_3$, $SiO_2$—MgO, $SiO_2$—$TiO_2$, $SiO_2$—$Al_2O_3$—MgO and a chromic compound supported $SiO_2$. $SiO_2$ is particularly preferable as the finely particulate inorganic support.

The finely particulate inorganic support mentioned above is generally calcined at a temperature of 100–1,000° C., preferably 300–900° C., and more preferably 400–900° C. prior to use. The amount of water adsorbed on the surface of the finely particulate inorganic support after calcined is 0.1 wt % or less, preferably 0.01 wt % or less and the content of a hydroxyl group on the surface of the support is 1.0 wt % or more, preferably in the range of 1.5–4.0 wt %, and more preferably in the range of 2.0–3.5 wt %. These finely particulate inorganic supports may be subjected to a contact treatment with an organoaluminum compound and/or a halogen-containing silicone compound, or an acid such as chromium nitrate(III) prior to the use.

Examples of the finely particulate organic support include finely particulate organic polymers such as finely particulate polymers of polyolefins, for example, polyethylene, polypropylene, poly-1-butene and poly-4-methyl-1-pentene, and those of polystyrenes.

As the organoaluminum compound (component (D)) a compound represented by the formula: $AlR^{16}{}_sR^{17}{}_tX_{3-(s+t)}$ is preferably used. In the formula, $R^{16}$ and $R^{17}$ each independently represent a hydrocarbon group such as an alkyl group of 1–10 carbon atoms, a cycloalkyl group of 1–10 carbon atoms and an aryl group of 1–10 carbon atoms, and a phenyl group optionally having a substituent such as an alkoxy group, a fluorine atom, a methyl group and a trifluorophenyl group; X represents a halogen atom; and s and t represent any one of integers satisfying the expression:

$$0 < s+t \leq 3.$$

Preferable examples of the organoaluminum compound include trialkyl aluminums such as trimethyl aluminum, triethyl aluminum, triisopropyl aluminum, triisobutyl aluminum, tri-n-butyl aluminum, tri-n-hexyl aluminum and tri-n-octyl aluminum; dialkyl aluminum halides such as dimethyl aluminum chloride, dimethyl aluminum bromide, diethyl aluminum chloride and diisopropyl aluminum chloride; alkyl aluminum sesquihalides such as methyl aluminum sesquichloride, ethyl aluminum sesquichloride, ethyl aluminum sesquibromide and isopropyl aluminum sesquichloride; and mixtures of two or more of the foregoing. Trialkyl aluminum is more preferable. Triethyl aluminum or triisobuthyl aluminum is further more preferable.

Specific examples of the component (E) used in the production of the supported metallocene catalyst II include ion-exchangeable layer compounds and inorganic silicates. The term "ion-exchangeable layer" as used herein does not include silicates.

The ion exchangeable layer compounds as the component (E) include ionic crystalline compounds of a hexagonal closest packing type, an antimony type, a $CdCl_2$ type and a $CdI_2$ type, which have a layer crystal structure. Specific examples of the ion exchangeable layer compound include crystalline acid salts of polyvalent metals such as $\alpha$-Zr $(HAsO_4)_2 \cdot H_2O$, $\alpha$-Zr$(HPO_4)_2$, $\alpha$-Zr$(KPO_4)_2 \cdot 3H_2O$, $\alpha$-Ti $(HPO_4)_2$, $\alpha$-Ti$(HAsO_4)_2 \cdot H_2O$, $\alpha$-Sn$(HPO_4)_2 \cdot H_2O$, $\gamma$-Zr $(HPO_4)_2$, $\gamma$-Ti$(HPO_4)_2$ and $\gamma$-Ti $(NH_4PO_4)_2 \cdot H_2O$.

The ion exchangeable layer compounds may be treated with salts and/or acids, if necessary. The ion exchangeable layer compounds except for silicates without any treatment with salts or acids have such a crystal structure that layers formed by ionic bonds, etc. are overlapped in parallel to one another with weak bonding force therebetween, and therefore, the layers contain exchangeable ions.

The inorganic silicates include clays, clay minerals, zeolite and diatomaceous earth. These inorganic silicates may be either synthetic products or natural minerals. Specific examples of clay or clay mineral may include allophane group such as allophane; kaolin group such as dickite, nacrite, kaolinite and anauxite; halloysite group such as meta-halloysite and halloysite; serpentine group such as chrysotile, lizardite and antigorite; smectite group such as montmorillonite, sauconite, beidellite, nontronite, saponite and hectorite; vermiculite minerals such as vermiculite; mica minerals such as illite, sericite and glauconite; attapulgite; sepiolite; palygorskite; bentonite; gnarl clay; gairome clay; hisingerite; pyrophyllite; and chlorite groups. These inorganic silicates may be in the form of mixed layers. In addition, the synthetic inorganic silicates include synthetic mica, synthetic hectorite, synthetic saponite and synthetic taeniolite.

Among the above inorganic silicates, preferred are kaolin group, halloysite group, serpentine group, smectite group, vermiculite minerals, mica minerals, synthetic mica, synthetic hectorite, synthetic saponite and synthetic taeniolite. Particularly preferred inorganic silicates are smectite, vermiculite minerals, synthetic mica, synthetic hectorite, synthetic saponite and synthetic taeniolite. These inorganic silicates may be used without any treatment or after treatments such as crushing by a ball mill and screening. Further, they may be used singly or in combination of the two or more.

The inorganic silicates can be treated with salts and/or acids to control an acid strength of these solid compounds if necessary. Further, when these compounds are treated with salts, ion composites, molecular composites or organic derivatives are formed so as to appropriately change the surface area and the interlayer distance. Specifically, exchangeable ions existing between the respective layers can be replaced with other bulkier ions with the aid of ion exchanging properties of these compounds, thereby obtaining a layer substance having an increased interlayer distance.

Although the component (E) may be used without any pretreatment, it is preferred that metal cations contained therein are ion-exchanged with cations dissociated from the salts and/or acids mentioned below.

The salts used for the ion exchange may be compounds comprising a cation which contains at least one atom selected from the group consisting of Group 1–14 atoms; preferably compounds comprising a cation which contains at least one atom selected from the group consisting of Group 1–14 atoms and at least one anion derived from an atom or atomic group selected from the group consisting of halogen atoms, inorganic acids and organic acids; more preferably compounds comprising a cation which contains at least one atom selected from the group consisting of Group 2–14 atoms and at least one anion selected from the group consisting of Cl, Br, I, F, $PO_4$, $SO_4$, $NO_3$, $CO_3$, $C_2O_4$, $ClO_4$, $OOCCH_3$, $CH_3COCHCOCH_3$, $OCl_2$, $O(NO_3)_2$, $O(ClO_4)_2$, $O(SO_4)$, OH, $O_2Cl_2$, $OCl_3$, OOCH, $OOCCH_2CH_3$, $C_2H_4O_4$ and $C_6H_5O_7$. These salts may be used singly or in combination of the two or more.

The acids used for the ion exchange may be selected from hydrochloric acid, sulfuric acid, nitric acid, acetic acid and oxalic acid. These acids may be used singly or in combination of the two or more. The salt treatment can be used in combination with the acid treatment. The methods in which the salt treatment and the acid treatment are combined include a method of conducting the acid treatment after the salt treatment, a method of conducting the salt treatment after the acid treatment, a method of conducting the salt and acid treatments simultaneously, and a method of conducting the salt and acid treatments simultaneously after the salt treatment. The acid treatment has such effects, in addition to the ion exchange, that impurities can be removed from the surfaces, and that a part of cations contained in the crystal structure such as Al, Fe, Mg and Li can be solved out.

The conditions for the salt or acid treatment are not particularly limited. Usually, the concentration of the salt or acid is, however, in the range of 0.1 to 30 wt %; the treating temperature is from room temperature to a boiling point of the solvent used; and the treating time is from 5 minutes to 24 hours. Such conditions are preferably selected so that at least a part of the compound to be treated is solved out. The salts and the acids are normally used in the form of an aqueous solution.

In the salt and/or acid treatments, the component (E) may be pulverized or granulated before, during or after the salt and/or acid treatments to adjust a shape thereof. In addition, other chemical treatments such as alkali treatment, organic compound treatment or organometallics treatment may be used in combination. The component (E) thus prepared preferably has a pore volume of 0.1 cc/g or more, more preferably 0.3 to 5 cc/g, as measured with respect to pores having a radius of 20 Å or more by the mercury-penetrating method. The component (E) thus prepared contains adsorbed water or interlayer water when treated in its aqueous solution. As used herein, the adsorbed water means water adsorbed on a surface or a crystal fracture face of the ion exchangeable layer compound or the inorganic silicate, and the interlayer water means water existing between the crystal layers.

It is preferred that the component (E) is used after removal of the aforementioned adsorbed water or interlayer water. The methods for removing the water are not particularly limited, but there may be used dehydrating methods such as heating, heating under a flowing gas and heating under reduced pressure, and azeotropic dehydration with an organic solvent. The heating may be conducted at such a temperature that no adsorbed water and interlayer water exists in the component (E). The heating temperature is usually 100° C. or higher, preferably 150° C. or higher. However, such a high temperature that causes destruction of the crystal structure should be avoided. The heating time is usually 0.5 hour or more, preferably one hour or more. The weight loss of the component (E) after dehydration and drying is preferably 3 wt % or less as determined by heating at a temperature of 200° C. for 2 hours under a vacuum condition of 1 mmHg. In accordance with this invention, in the case of using the component (E) whose weight loss is adjusted to 3 wt % or less based on the weight of the component (E), it is preferred that the weight loss of the component (E) is maintained also when the component (E) is brought into contact with the component (A) and the component (D).

Now, the method for producing the supported metallocene catalysts I and II will be described below.

The supported metallocene catalyst I is obtained by reacting the component (A) with the component (B) and optionally the component (D) in the presence of the component (C). The order of adding the components (A) and (B) to the component (C) may be changed arbitrarily. For example, the component (A) dissolved in a suitable hydrocarbon solvent is first added to the component (C) and thereafter the component (B) is added thereto. The components (B) and (A) which are allowed to react in advance may be simultaneously added to the component (C). Alternatively, the component (B) is first added to the component (C) and thereafter the component (A) is added thereto. The temperature of the reaction is generally in the range of from –20 to 200° C., preferably in the range of from 0 to 120° C. The time required for the reaction is generally 0.1 minute or more, preferably in the range of one minute to 200 minutes. The supported metallocene catalyst obtained as described above is used after prepolymerized with a small amount of an olefin, if necessary.

Specific examples of the olefin to be used for the prepolymerization include ethylene, propylene, 1-butene, 1-hexene, 3-methyl-1-butene and 4-methyl-1-pentene. These olefins may be used in combination of the two or more.

The supported metallocene catalyst I preferably used in the production of the olefin polymer of this invention is a supported metallocene catalyst prepared by sequentially performing the following step (a)-step (c) or a preactivated supported metallocene catalyst obtained by sequentially performing the following step (a)-step (d), for example.

(a) The step of preparing a metallocene catalyst by reacting a metallocene compound (A) with an aluminoxane in an inert solvent;

(b) The step of preparing a crude supported metallocene catalyst by bringing the metallocene catalyst obtained in the step (a) into contact with a finely particulate inorganic support in the presence of an inert solvent at a temperature of 85–150° C., thereby depositing the metallocene catalyst on the finely particulate inorganic support;

(c) The step of preparing a purified supported metallocene catalyst by washing the slurry containing the crude supported metallocene catalyst obtained in the step (b) at least twice with an aliphatic hydrocarbon at a temperature of from –50 to 50° C.; and (d) The step of preparing a preactivated supported metallocene catalyst by bringing the supported metallocene catalyst obtained in the step (c) into contact with an olefin, thereby prepolymerizing the olefin, and further depositing 0.01–500 kg of an olefin prepolymer per kg of the supported metallocene catalyst on the catalyst.

In the step (a), 10–1,000 mol, preferably 20–500 mol of aluminoxane in terms of aluminum atom per mol of the metallocene compound (A) is reacted with the compound (A) in an inert solvent at a temperature of from –50 to 100° C., preferably from 0 to 50° C., for 1 minute to 10 hours, preferably 3 minutes to 5 hours to form a metallocene catalyst.

The use of the inert solvent is favorable for the purpose of carrying out the uniform and efficient reaction. The amount of the inert solvent used is not particularly limited, and it is generally in the range of 10–10,000 liters, and preferably in the range of 10–1,000 liters, per mol of the metallocene compound (A).

Specific examples of the inert solvent used in the aforementioned reaction include aromatic hydrocarbons such as benzene, toluene, xylene and cumene; aliphatic hydrocarbons such as butane, tetramethyl butane, pentane, ethyl pentane, trimethyl pentane, hexane, methyl hexane, ethyl hexane, dimethyl hexane, heptane, methyl heptane, octane, nonane, decane, hexadecane and octadecane; alicyclic hydrocarbons such as cyclopentane, methylcyclopentane, cyclohexane and cyclooctane; halogenated hydrocarbons obtained by substituting halogens for the aromatic hydrocarbons, aliphatic hydrocarbons and alicyclic hydrocarbons; and mixed solvents thereof. Ethers such as ethyl ether and tetrahydrofuran can be also used.

The preferred inert solvents are aromatic hydrocarbons. The solvent of a commercially available aluminoxane solution may be used for the reaction as it is, or in combination with other aromatic hydrocarbons.

In the step (b) subsequent to the step (a), the crude supported metallocene catalyst is obtained in the form of a solid product having the metallocene catalyst mentioned above deposited on the finely particulate inorganic support by bringing the metallocene catalyst obtained in the step (a) into contact with the finely particulate inorganic support in the presence of the inert solvent used as the reaction solvent in the step (a) at a temperature of 85–150° C. In this contact reaction, an inert solvent may be used additionally, if necessary.

Regarding the content ratio of the metallocene catalyst to the finely particulate inorganic support in the crude supported metallocene catalyst, the amount of the finely particulate inorganic support is in the range of 1–1,000 kg, preferably in the range of 5–500 kg, per mol of the transition metal atom originating in the metallocene compound (A) contained in the reaction product of the metallocene compound (A) as the metallocene catalyst and the aluminoxane. The amount of the inert solvent used in the step (b) is in the range of 10–10,000 liters, preferably in the range of 10–1,000 liters, per mol of the transition metal atom originating in the metallocene compound (A) contained in the reaction product of the metallocene compound (A) as the metallocene catalyst and the aluminoxane.

The contact between the metallocene catalyst and the finely particulate inorganic support is carried out at a temperature of 85–150° C., preferably 90–130° C., and particularly preferably 95–120° C. for 5 minutes to 100 hours, preferably 10 minutes to 50 hours. The temperature condition is a particularly important factor. When this contact is carried out at a temperature in the above-described range, the resultant supported metallocene catalyst can have a high polymerization activity. When this catalyst is used for the polymerization of an olefin, the resultant olefin polymer can have a high bulk specific gravity and good powder morphology.

In the subsequent step (c), the purified supported metallocene catalyst is obtained by washing the crude supported metallocene catalyst obtained in the step (b) which contains the inert solvent at least twice with an aliphatic hydrocarbon at a temperature of from −50 to 50° C.

Specific examples of the aliphatic hydrocarbon used for the washing include the aliphatic hydrocarbons and their mixtures mentioned above as the inert solvent. n-Hexane, isopentane and mixtures thereof are preferable.

The washing in the step (c) may comprise separating the inert solvent by filtration, centrifugation or decantation from the slurry formed of the inert solvent and the crude supported metallocene catalyst after the step (b) and thereafter washing the crude supported metallocene catalyst with an aliphatic hydrocarbon. Alternatively, the method to be employed may comprise adding an aliphatic hydrocarbon without separating the inert solvent from the slurry formed of the inert solvent and the crude metallocene catalyst after the step (b), separating the mixed solvent of the inert solvent and the aliphatic hydrocarbon in the same manner as described above, and thereafter washing the crude supported metallocene catalyst by the use of the aliphatic hydrocarbon. For the washing in the step (c), the latter method is more preferable.

The washing is carried out repeatedly till the liquation of the metallocene catalyst into the aliphatic hydrocarbon stops, by using 1–500 liters, preferably 10–100 liters of the aliphatic hydrocarbon per kg of the finely particulate inorganic support used in the step (b) at a temperature of from −50 to 50° C., preferably from −30 to 40° C., and more preferably from −30 to 30° C. in each washing. Although the washing is preferably carried out at least twice, and generally not less than four times, the number of washings is not limited thereto.

The temperature of the washing is an important factor. When the washing is carried out at a temperature in the above-described range, the resultant supported metallocene catalyst has a high polymerization activity. When the polymerization of an olefin is carried out by the use of this catalyst, the resultant olefin polymer can have a particularly high bulk specific gravity and good powder morphology.

The preactivated supported metallocene catalyst used in this invention is obtained in the step (d) as described above by bringing the supported metallocene catalyst obtained in the step (c) into contact with an olefin, thereby prepolymerizing the olefin and depositing 0.01–500 kg of the olefin prepolymer per kg of the supported metallocene catalyst on the catalyst.

The olefin prepolymer to be deposited on the preactivated supported metallocene catalyst is an olefin of 2–20 carbon atoms. Specific examples of the olefin include homopolymers of ethylene, propylene, 1-butene, 1-pentene, 4-methyl-1-pentene, 2-methyl-1-pentene, 1-hexene, 1-octene, 1-decene and 1-dodecene, and copolymers formed by combining two or more such olefins. Ethylene homopolymer, propylene homopolymer, ethylene/olefin copolymers formed of ethylene and olefin other than ethylene, and propylene/olefin copolymers formed of propylene and an olefin other than propylene are particularly preferable. Further, the olefin prepolymer preferably has an intrinsic viscosity [n] of 0.1–10 dl/g, preferably 0.2–7 dl/g, as determined in decalin at 135° C. In order to obtain an olefin polymer having high melt tension, an intrinsic viscosity [n] of the olefin prepolymer is more than 10 dl/g and not more than 100 dl/g, preferably from 15 to 80 dl/g, more preferably from 20 to 50 dl/g.

The olefin is preferably prepolymerized by a method which comprises introducing the olefin into the slurry of the supported metallocene catalyst obtained in the step (c) dispersed in an aliphatic hydrocarbon, thereby bringing the olefin into contact with the supported metallocene catalyst and prepolymerizing the olefin. As the slurry of the supported metallocene catalyst dispersed in the aliphatic hydrocarbon, the catalyst obtained by the washing at the final stage of the step (c) may be used without separation from the aliphatic hydrocarbon. Alternatively, the catalyst may be separated from the aliphatic hydrocarbon and subsequently redispersed in the aliphatic hydrocarbon of the same kind and then put to use.

Although the prepolymerization of the olefin may be carried out in a liquid phase using the olefin itself to be polymerized as a solvent or in a gas phase without any solvent, it is preferably carried out in the presence of an aliphatic hydrocarbon for the controlled polymerization of a small amount of olefin and the uniform prepolymerization.

The prepolymerization of the olefin in the aliphatic hydrocarbon is carried out by introducing 0.01–1,000 kg, preferably 0.1–500 kg of the olefin into the slurry formed of 0.005–5 $m^3$, preferably 0.01–1 $m^3$ of the aliphatic hydrocarbon per kg of the supported metallocene catalyst, thereby bringing the olefin into contact with the aliphatic hydrocarbon at a temperature of from −50 to 100° C., preferably from 0 to 50° C. for 1 minute to 50 hours, and preferably 3 minutes to 20 hours.

In the prepolymerization of the olefin mentioned above, the reaction product of the metallocene compound (A) and the aluminoxane preferably used as the activating compound (B) is deposited on the supported metallocene catalyst, and there is no need to add a co-catalyst such as an organoaluminum compound (e.g., trialkyl aluminum) and aluminoxane. However, the co-catalyst may be added, if necessary. The amount of the co-catalyst added is 1,000 moles or less, preferably 500 moles or less, in terms of aluminum atom, per mol of the transition metal atom originating in the metallocene compound (A) in the supported metallocene catalyst.

In this invention, in order to obtain an olefin polymer having good powder morphology, the prepolymerization of the olefin is preferably carried out in the presence of hydrogen so that the weight average molecular weight (Mw) of the resultant olefin prepolymer may be in the range of 100,000–500,000 g/mol.

The supported metallocene catalyst I may also be produced by a first step of reacting an aluminoxane with a finely particulate inorganic support and a second step of reacting the resultant with a metallocene compound (A). The catalyst obtained in this way is preferably used in the production of the olefin polymer according to this invention, yielding an olefin polymer having good powder morphology.

The supported metallocene catalyst II used in this invention is prepared by bringing the components (A), (E) and (D) into contact with each other. Although the method of this contact reaction is not particularly limited, the following methods are available for illustration.

(1) Method of bringing the components (A) and (E) into contact with each other;

(2) Method of bringing the components (A) and (E) into contact with each other and then adding the component (D) to the mixture;

(3) Method of bringing the components (A) and (D) into contact with each other and then adding the component (E) to the mixture;

(4) Method of bringing the components (E) and (D) into contact with each other and then adding the component (A) to the mixture; and (5) Method of bringing the components (A), (E) and (D) into contact with each other at the same time.

The contact between these components may be performed not only upon the production of the catalyst but also upon prepolymerization or polymerization of the olefins. During or after the respective components are brought into contact with each other, polymers such as polyethylene and polypropylene or solid components of inorganic oxides such as silica and alumina may co-exist therein or may be contacted therewith. The contact between the respective components can be conducted in an atmosphere of an inert gas such as nitrogen or in the presence of an inert hydrocarbon solvent such as pentane, hexane, heptane, toluene and xylene. Further, the contact is preferably conducted at a temperature of from −20° C. to a boiling point of the solvent used, more preferably from room temperature to the boiling point of the solvent used.

The amount of the component (A) used is usually in the range of from $10^{-4}$ to 10 mmol, preferably from $10^{-3}$ to 5 mmol per gram of the component (E). The amount of the component (D) used is usually in the range of from 0.01 to $10^4$ mmol, preferably from 0.1 to 100 mmol per gram of the component (E). In addition, the atomic ratio of the transition metal contained in the component (A) to aluminum contained in the component (D) is usually in the range of from 1/0.01 to $1/10^6$, preferably from 1/0.1 to $1/10^5$. The catalyst thus prepared may be used as it is without washing, or may be used after washing.

Further, the catalyst can be used in combination with additional component (D), if required. Specifically, when the components (A) and/or (E) and the component (D) are used to prepare the catalyst, the additional component (D) may be added to a reaction system separately from the preparation of the catalyst. In this case, the amount of the component (D) added can be selected so that the atomic ratio of the transition metal contained in the component (A) to aluminum contained in the component (D) may be in the range of from 1/0 to $1/10^4$, preferably from 1/1 to $1/10^3$.

Further, in the case of the supported metallocene catalyst II prepared as described above, the olefin is prepolymerized to deposit the olefin prepolymer on the supported catalyst and then used for the production of the olefin polymer of this invention, in the same manner as the case of the supported metallocene catalyst I.

The supported metallocene catalyst I or II thus obtained is further combined with an organoaluminum compound (component (D')) to produce the olefin polymerization catalyst, which is advantageously used for the production of the olefin polymer of this invention.

The component (D') used in combination with the supported metallocene catalyst I or II in the production of the olefin polymer is selected from the aforementioned organoaluminum compounds which are used in the production of the supported metallocene catalyst I or II. However, it may be the same as or different from the organoaluminum compound used in the production of the metallocene supported catalyst I or II.

The amount of the component (D') to be used in the production of the olefin polymer is selected so that the amount of the Al atom in the component (D') is in the range of 1–5,000 moles, preferably in the range of 5–3,000 moles, and most preferably in the range of 10–1,000 moles per mol of the transition metal atom originating in the metallocene compound (A) contained in the supported metallocene catalyst or the preactivated supported metallocene catalyst.

The amount of the supported metallocene catalyst or the preactivated supported metallocene catalyst used for polymerization is in the range of from $1\times10^{-10}$ to $1\times10^{-3}$ mol, preferably in the range of from $1\times10^{-9}$ to $1\times10^{-4}$ mol in terms of the transition metal atom originating in the metallocene compound (A) contained per liter of the polymerization volume. When the amount of the catalyst is set in the above-described range, it will be possible to efficiently polymerize the olefin at a controlled rate of polymerization reaction.

The term, "polymerization volume" as used herein means the volume of the liquid phase in the polymerization vessel in the case of the liquid phase polymerization or the volume of the gas phase in the polymerization vessel in the case of the gas phase polymerization.

The method for the production of an olefin according to this invention comprises a method for the production of an olefin polymer by using the olefin polymerization catalyst which contains the metallocene compound of this invention as described in any of (1) to (3).

As processes to be applied for the method of the production of an olefin polymer according to this invention, known polymerization processes of olefins can be employed, for example, slurry polymerization wherein olefins are polymerized in an inert solvent including an aliphatic hydrocarbon such as butane, pentane, hexane, heptane and isooctane, an alicyclic hydrocarbon such as cyclopentane, cyclohexane and methylcyclohexane, an aromatic hydrocarbon such as toluene, xylene and ethylbenzene, and gasoline fraction and hydrogenated diesel oil fraction. Bulk polymerization wherein olefin itself is used as solvent or gas-phase polymerization wherein olefin is polymerized in a gas phase may be employed. A polymerization process wherein these two or more polymerization processes are combined may be employed. The most preferable combination of polymerization processes is that at the first stage bulk polymerization is carried out and at the subsequent second stage gas-phase polymerization is carried out. It is also possible to employ solution polymerization.

The process for the production of an olefin polymer according to this invention can employ the respective conditions of a polymerization temperature of from −50 to 150° C., preferably from 20 to 120° C., more preferably from 40 to 100° C. and of a polymerization pressure of from atmospheric pressure to 9.9 Mpa (gauge pressure), preferably from 0.4 to 5.0 Mpa (gauge pressure). If desired, a chain transfer agent such as hydrogen may be introduced in order to adjust the molecular weight of the olefin polymer to be obtained.

After polymerization is complete, unreacted monomers and hydrogen are separated from the polymerization system and treatment such as deactivation of the catalyst used produces the olefin polymer.

The olefin polymers of this invention may be produced by the processes for the production of olefin polymers as described above.

As used herein, the term, "olefin(s)" refers to an olefin of 2–20 carbon atoms. Specific examples include ethylene, propylene, 1-butene, 1-pentene, 1-hexene, 1-heptene, 1-octene, 1-decene, 1-dodecene, 1-hexadecene, 4-methyl-1-pentene, styrene, vinylcyclohexene, a diene, a triene and a cyclic olefin. As used herein, the term, "olefin(s) other than propylene" refers to an olefin of 2–20 carbon atoms. Specific examples include ethylene, 1-butene, 1-pentene, 1-hexene, 1-heptene, 1-octene, 1-decene, 1-dodecene, 1-hexadecene, 4-methyl-1-pentene and a mixture of two or more of the foregoing. In this invention, the olefin other than propylene that is used most preferably is ethylene, 1-butene or a mixture of ethylene and 1-butene.

As used herein, the term, "olefin polymer(s)" refers to a homopolymer comprising one olefin selected from olefins of 2–20 carbon atoms or to a copolymer comprising two or more olefins.

As used herein, the "olefin polymer(s)" may contain as the structural units, styrene, vinylcyclohexane, diene or triene within the range of 30 molar % or less based on the molar numbers of the structural units constituting the polymer.

Preferably, the olefin polymer of this invention is a propylene/olefin copolymer containing as structural units, a propylene unit and an olefin unit other than propylene wherein the content of the olefin unit other than propylene is 0.1–80 molar % based on the molar numbers of structural units constituting the copolymer. The content of the olefin unit other than propylene in such copolymer is preferably 0.5–50 molar %, more preferably 1–30 molar %, and most preferably 1–10 molar %.

The olefin polymer produced by the production process of this invention may be any of a random copolymer, a block copolymer and a random block copolymer when the polymer is a propylene/olefin copolymer containing as the structural units, a propylene unit and an olefin unit other than propylene.

When the olefin polymer of this invention is a block copolymer, the olefin polymerization catalyst containing a metallocene compound according to this invention can be used to produce a propylene homopolymer (I) (which may be referred to as "Segment A" hereafter) at the first stage of process and to produce a propylene/olefin random copolymer (II) (which may be referred to as "Segment B" hereafter) containing as structural units, a propylene unit and an olefin unit other than propylene wherein the content of the propylene unit is 10–90 molar %, preferably 20–80 molar % based on the molar numbers of the structural units constituting the copolymer (II) at the second stage of process, desirably affording the block copolymer. It is preferred that the content of Segment A is 10–95 wt % and the content of Segment B is 90–5 wt % based on the weight of the block copolymer. The thus obtained polymer may be denoted a propylene//propylene/olefin.block copolymer.

When the olefin polymer of this invention is a random block copolymer, the olefin polymerization catalyst containing a metallocene compound according to this invention can be used to produce a propylene/olefin random copolymer (I) (which may be referred to as "Segment A" hereafter) containing as structural units, a propylene unit and an olefin unit other than propylene wherein the content of the olefin unit other than propylene is 0.1–30 molar %, preferably 0.3–20 molar %, and most preferably 0.5–10 molar % based on the molar numbers of the structural units constituting the copolymer (I) at the first stage of process and to produce a propylene/olefin random copolymer (II) (which may be referred to as "Segment B" hereafter) containing as structural units, a propylene unit and an olefin unit other than propylene wherein the content of the propylene unit is 10–90 molar %, preferably 20–80 molar % based on the molar numbers of the structural units constituting the copolymer (II) at the second stage of process, desirably affording the random block copolymer. It is preferred that the content of Segment A is 10–95 wt % and the content of Segment B is 90–5 wt % based on the weight of the random block copolymer. The thus obtained polymer may be denoted a propylene/olefin//propylene/olefin.random block copolymer.

In order to produce molded articles with excellent shock resistance, transparency and flexibility, the melt flow rate (MFR) of Segment B which is the propylene/olefin random polymer (II) in the propylene//propylene/olefin.block copolymer or the propylene/olefin//propylene/olefin.random block copolymer as described above is preferably 300 g/10 min or less, more preferably 100 g/10 min or less, even more preferably 10 g/10 min or less, further more preferably 1 g/10 min or less, even further more preferably 0.1 g/10 min or less, and most preferably 0.01 g/10 min or less. As used herein, "melt flow rate (MFR)" is a value (unit: g/10 min) obtainable from the measurement in accordance with JIS K7210 at a load of 21.18 N and a temperature of 230° C.

For the propylene//propylene/olefin.block copolymer or the propylene/olefin//propylene/olefin.random block copolymer as described above, the MFR of Segment B (which may be referred to as "MFRB" hereafter) can be calculated according to the equation below by using the MFR of the copolymer (which may be referred to as "$MFR_T$" hereafter), the content of segment A in the copolymer (which may be referred to as "$W_A$" hereafter; unit-wt %), the MFR of Segment A (which may be referred to as "$MFR_A$" hereafter), and the content of segment B in the copolymer (which may be referred to as "$W_B$" hereafter; unit-wt %).

$$\log(MFR_B) = (100/W_B) \times \{\log(MFR_T) - (W_A/100) \times \log(MFR_A)\}$$

With respect to the block copolymer or the random block copolymer according to this invention, the olefin polymerization catalyst containing a metallocene compound according to this invention is used to carry out the first step under such conditions: at a temperature of from 30 to 100° C., preferably from 50 to 80° C.; at a pressure of from 0.3 to 5 Mpa, preferably from 1 to 4 Mpa; and for a period of from 0.5 to 10 hours, preferably from 1 to 5 hours. Continuously, the second and subsequent steps are carried out at a temperature of from 30 to 100° C., preferably from 50 to 80° C., at a pressure of from 0.3 to 5 Mpa, preferably from 1 to 4 Mpa, and for a period of from 0.5 to 10 hours, preferably from 1 to 5 hours. In the first and the second steps hydrogen can, respectively, be used as a chain transfer agent to adjust the MFRs of the polymers produced in the respective steps within the desired ranges. The first and second steps may include plural stages, respectively, but they are preferably comprised of a single stage.

The melting point of the olefin polymer of this invention is preferably from 80 to 165° C., and more preferably from 85 to 162° C.

When the olefin polymer of this invention is a copolymer containing as structural units, a propylene unit and an olefin unit other than propylene and is specifically a propylene/ethylene.random copolymer or a propylene/ethylene/1-butene random.copolymer containing a small amount of 1-butene, it is preferred that the relationship described below is satisfied between the content of the propylene unit in the copolymer (P: molar %) and the melting point of the copolymer (Tm: ° C.).

$$170 > Tm \geq 145 - 5.5 (100-P)$$

Preferably, the following relationship holds:

$$170 > Tm \geq 147 - 5.5 (100-P)$$

The weight average molecular weight ($M_w$) of the olefin polymer of this invention is preferably in the range of from $1 \times 10^4$ to $2 \times 10^6$ g/mole, and more preferably, from $1 \times 10^5$ to $5 \times 10^5$ g/mole. The ratio ($M_w/M_n$) of the weight average molecular weight ($M_w$) to the number average molecular weight ($M_n$) is preferably in the range of from 1.5 to 3.8, more preferably from 1.5 to 3.5, even more preferably from 1.8 to 3.0, and most preferably from 1.8 to 2.8.

The MFR of the olefin polymer of this invention is preferably in the range of from 0.001 to 300 g/10 min. However, the preferable range from the standpoint of workability is from 0.5 to 100 g/10 min.

{0234}

The intrinsic viscosity [η]of the olefin polymer of this invention is preferably in the range of from 0.5 to 1.2 dl/g, and more preferably, from 0.5 to 5 dl/g.

The isotactic pentad ratio ($I_5$) which represents the stereoregularity of an olefin polymer of this invention is not particularly limited and is preferably from 0.400 to 0.990, more preferably from 0.800 to 0.990, even more preferably from 0.850 to 0.990, and most preferably, from 0.920 to 0.990.

The isotactic triad ratio ($I_3$) of an olefin polymer of this invention is not particularly limited and is preferably from 0.50 to 0.999, more preferably from 0.85 to 0.999, even more preferably from 0.87 to 0.999, and most preferably, from 0.94 to 0.990.

The proportion of the molar number of the olefin units arising from the 2,1-insertion of olefin to the total molar number of the olefin units constituting the olefin polymer of this invention and the proportion of the molar number of the propylene units arising from the 3,1-insertion of olefin to the total molar number of the olefin units constituting the olefin polymer of this invention are not particularly limited, and they are independently 5 molar % or less, and preferably 3 molar % or less.

For the olefin polymer of this invention, the isotactic pentad ratio ($I_5$), the isotactic triad ratio ($I_3$), the proportion of the molar number of the olefin units arising from the 2,1-insertion of olefin to the total molar number of the olefin units constituting the olefin polymer, and the proportion of the molar number of the propylene units arising from the 3,1-insertion of olefin to the total molar number of the olefin units constituting the olefin polymer can be calculated based on the measurement results of $^{13}C$ NMR spectra as determined according to the method described below.

Specifically, a sample (or olefin polymer) is dissolved in a mixed solution of o-dichlorobenzene/bromobenzene in a weight ration of 8/2 so that its concentration in the mixed solution may be 20 wt %. The $^{13}C$ NMR spectrum of the sample solution is measured at a wavelength of 67.20 MHz and at a measuring temperature of 130° C. For example, "JEOL-GX270 NMR" (manufactured by JEOL) may be used as the measuring device In the case of olefin homopolymer, the isotactic pentad ratio ($I_5$) and the isotactic triad ratio ($I_3$) can be calculated by the measurement of $^{13}C$ NMR spectra, as proposed in A. Zambelli et al., Macromolecules, 6, pp. 925–926 (1973), which are indices representing stereoregularity of polymer. The assignment of peaks in measuring the $^{13}C$ NMR spectra followed the assignment method as proposed in A. Zambelli et al., Macromolecules, 8, p. 687 (1975). The isotactic triad ratio ($I_3$) of copolymer was calculated according to the method as proposed in JP-A-07-149833 and JP-A-08-283343.

The isotactic pentad ratio ($I_5$) represents the proportion of olefin units forming five successive meso bonds to the total number of olefin units constituting a olefin polymer; and the isotactic triad ratio ($I_3$) represents the proportion of olefin units forming three successive meso bonds to the total number of olefin units in the molecular backbone of the olefin polymer. Therefore, higher isotactic pentad ratio ($I_5$) or higher isotactic triad ($I_3$) ratio shows higher isotacticity. Between these two the isotactic pentad ratio ($I_5$) is particularly used as the index of isotacticity for homopolymer, whereas the isotactic triad ratio ($I_3$) is used as the index of isotacticity for homopolymer or copolymer.

The proportion of the molar number of the olefin units arising from the 2,1-insertion of olefin to the total molar number of the olefin units constituting a olefin polymer, and the proportion of the molar number of the propylene units arising from the 3,1-insertion of olefin to the total molar number of the olefin units constituting a olefin polymer can be calculated based on the measurement of $^{13}C$ NMR spectra as determined according to the method published in T. Tsutsui et al., Polymer, 30, pp. 1350–1356 (1989), which are the indices representing the stereoregularity of olefin polymers.

The olefin polymer of this invention can be, if necessary, compounded with a variety of synthetic resins in addition to a variety of additives such as an antioxidant, a ultraviolet absorbing agent, an antistatic agent, a nucleating agent, a lubricant, a flame retardant, an anti-blocking agent, a colorant, or an inorganic or organic filler; and it can then be heated and melt-kneaded using a conventional melt-mixer approximately at a temperature of from 190° C. to 350° C. for a period of 20 seconds to 30 minutes and, if desired, can be extruded into a strand form. Then it can be further thinly cut into a particulate form (i.e., pellets), which may be provided for the manufacture of various molded articles. Specifically, the polymer may suitably be used as a film, a sheet, a fiber, an injection-molded product, a blow-molded product, a container, a stretched thread, an unwoven cloth, a foamed part, etc., or alternatively, it may suitably used as a sealant. The molded articles produced from the olefin polymers of this invention are provided with excellent stiffness, heat resistance, surface hardness, anti-scratching property, shock-absorbance, heat-sealing effect, transparency, antiblocking property or the like.

EXAMPLES

This invention will be further illustrated by the following Examples and Comparative Examples; however, the invention is not to be limited to these examples. The definitions of the terms to be used in the Examples and the Comparative Examples and the methods of measurement therefor are described below.

(1) Melt flow rate (MFR) (unit: g/10 min): Measured in accordance with Condition 14 (at a load of 21.18 N and a temperature of 230° C.) in Table 1 of JIS K7210.

(2) Weight average molecular weight ($M_w$) and its ratio ($M_w/M_n$) to number average molecular weight ($M_n$) Determined by gel permeation chromatography (GPC) with a column (PSKgel GMH6-HT manufactured by Tosoh Corporation) and with a measuring device (GPC-150C manufactured by Waters Ltd.), where a sample (olefin polymer) was dissolved in o-dichlorobenzene to give a concentration of 0.05 wt % and the resultant solution was subjected to measurement at 135° C.

(3) Melting point (unit: ° C.): Measured with a differential scanning calorimeter ("DCS 7 type" manufactured by Perkin Elmer, Inc.). The temperature of a sample (olefin polymer) was elevated from room temperature to 230° C. at a rate of 30° C./min and the sample maintained at the same temperature for 10 minutes; the temperature was then lowered to −20° C. at a rate of 20° C./min and the sample maintained at the same temperature for 10 minutes. Subsequently, while the temperature was again elevated at a rate of 20° C./min, the temperature displaying a peak of melting was taken as a melting point.

(4) The content of olefin unit of an olefin polymer in the case of a propylene/olefin copolymer which contains as structural units, a propylene unit and an olefin unit other than propylene (unit: molar %): Determined by measurement on $^{13}C$ NMR.

(5) Intrinsic viscosity ([η]) (unit: dl/g): Measured in tetralin as solvent at 135° C. using an automatic viscometer ("AVS2-type" manufactured by Mitsui Toatsu Chemicals Co., Ltd.).

Example 1

Synthesis of dimethylsilylene(2-methyl-4-phenyl-indenyl)(2-(2-(5-methyl)-furyl)-4-phenyl-indenyl) zirconium dichloride (1) Synthesis of dimethyl(2-methyl-4-phenylindenyl)(2-(2-(5-methyl)-furyl)-4-phenyl-indenyl)silane A 500 ml glass reaction vessel was charged with 11.7 g (56.7 mmol) of 2-methyl-4-phenylindene and 100 ml of THF and cooled to −70° C. on a dry ice/methanol bath. To the mixture was added dropwise 36 ml (56.9 mmol) of a n-butyllithium/hexane solution (1.58 mol/l). After addition was completed, the mixture was stirred overnight while it was gradually brought to room temperature, and thus a lithium solution of 2-methyl-4-phenylindene was prepared.

A separate 500 ml glass reaction vessel was charged with 22 g (170 mmol) of dimethyldichlorosilane and 100 ml of THF, and cooled to −70° C. on a dry ice/methanol bath. To the mixture was added dropwise the lithium solution of 2-methyl-4-phenylindene prepared before slowly. After addition was completed, the mixture was stirred at room temperature for 1 h and the solvent and excessive dimethyldichlorosilane was distilled off under reduced pressure. To this was added 100 ml of THF and thus a chlorosilane solution was prepared.

A different 500 ml glass reaction vessel was charged with 15.5 g (56.9 mmol) of 2-(2-(5-methyl)-furyl)-4-phenylindene and 200 ml of THF, and cooled to −70° C. on a dry ice/methanol bath. To the mixture was added dropwise 36 ml (56.9 mmol) of a n-butyllithium/hexane solution (1.58 mol/l). After addition was completed, the mixture was stirred for 4 h while it was gradually brought to room temperature. The mixture was again cooled to −70° c on a dry ice/methanol bath and after addition of 0.23 ml (2.9 mmol) of 1-methylimidazole, the chlorosilane solution prepared previously was added dropwise. After addition was completed, the mixture was stirred overnight while it was gradually brought to room temperature.

To the reaction solution was added distilled water and it was transferred to a separatory funnel and washed with brine until it turned neutral. Anhydrous sodium sulfate was added and the solution was dried overnight. The anhydrous sodium sulfate was filtered off and the solvent was distilled off under reduced pressure. Purification on a silica gel column gave 22 g (72% yield) of dimethyl(2-methyl-4-phenyl-indenyl)(2-(2-(5-methyl)-furyl)-4-phenyl-indenyl)silane as a light yellow solid.

(2) Synthesis of dimethylsilylene(2-methyl-4-phenyl-indenyl)(2-(2-(5-methyl)-furyl)-4-phenyl-indenyl)zirconium Dichloride A 500 ml glass reaction vessel was charged with 11.9 g (22.3 mmol) of dimethyl(2-methyl-4-phenyl-indenyl)(2-(2-(5-methyl)-furyl)-4-phenyl-indenyl)silane and 200 ml of diethyl ether and cooled to −70° C. on a dry ice/methanol bath. To the mixture was added dropwise 28 ml (44.2 mmol) of a n-butyllithium/hexane solution (1.58 mol/l). After addition was completed, the mixture was stirred overnight while it was gradually brought to room temperature. The solvent of the reaction solution was concentrated to about 20 ml under reduced pressure and, upon addition of 250 ml of toluene, the reaction solution was cooled to −70° C. on a dry ice/methanol bath. To this was added 5.2 g (22.3 mmol) of tetrachlorozirconium. Subsequently, the mixture was stirred overnight while it was gradually brought to room temperature.

The solvent was distilled off under reduced pressure and recrystallization from toluene/hexane gave 2.32 g (15% yield) of dimethylsilylene(2-methyl-4-phenyl-indenyl)(2-(2-(5-methyl)-furyl)-4-phenyl-indenyl)zirconium dichloride in a racemic-like form (purity of 97%) as an orange crystal. The results determined by $^1$H-NMR (CDCl$_3$) for the racemic-like form are shown below.

$^1$H-NMR data (CDCl$_3$) of the racemic-like form: δ1.22 (s, 3H), δ1.38 (s, 3H), δ2.26 (s, 3H), δ2.43 (s, 3H), δ6.06 (d, 1H), δ6.17 (d, 1H), δ6.67–6.73 (m, 2H), δ6.92 (s, 1H), δ7.03 (s, 1H), δ7.14–7.18 (m, 3H), δ7.26–7.27 (m, 2H), δ7.33–7.34 (m, 2H), δ7.38–δ7.44 (m, 2H), δ7.59 (dd, 2H), δ7.67 (dd, 2H), δ7.75 (d, 1H).

Production of Propylene Homopolymer Using Dimethylsilylene(2-methyl-4-phenyl-indenyl)(2-(2-(5-methyl)-furyl)-4-phenyl-indenyl)zirconium Dichloride as a Catalytic Component A SUS autoclave was sequentially charged with 1 liter of toluene, a toluene solution of methylaluminoxane (MMAO3A, manufactured by Tosoh-Akzo Co., Ltd.) (Al/Zr=10,000), and 3 ml (0.30×10$^{-6}$ mol) of a toluene solution of dimethylsilylene(2-methyl-4-phenyl-indenyl)(2-(2-(5-methyl)-furyl)-4-phenyl-indenyl)zirconium dichloride, and the mixture was heated at 30° C. Into the autoclave was introduced propylene at a pressure of 0.3 Mpa and polymerization was carried out for 1 h. After the polymerization was completed, polymer was filtered and the catalyst component was decomposed with 1 liter of hydrochloric acidic methanol. Subsequently, filtration, washing and drying were carried out to obtain 27.7 g of a propylene homopolymer. The polymerization activity was 97 kg-polymer/mmol (Zr) .hr. The obtained propylene homopolymer was analyzed and the results were as follows:

MFR=0.002 g/10 min.; Mw=1.6×10$^6$ g/mol; Mw/Mn=2.74; and mp 161.4° C.

Comparative Example 1

Synthesis of Racemic Dimethylsilylenebis(2-methyl-4-phenyl-indenyl)zirconium Dichloride According to the method described in JP-A-06-100579, racemic dimethylsilylenebis(2-methyl-4-phenyl-indenyl) zirconium dichloride was synthesized.

Production of Propylene Homopolymer Using Racemic Dimethylsilylenebis(2-methyl-4-phenyl-indenyl)zirconium Dichloride as a Catalytic Component A SUS autoclave was sequentially charged with 1 liter of toluene, a toluene solution of methylaluminoxane (MMAO3A, manufactured by Tosoh-Akzo Co., Ltd.) (Al/Zr=10,000), and 3 ml (0.14×10$^{-6}$ mol) of a toluene solution of rac-dimethylsilylenebis(2-methyl-4-phenyl-indenyl)zirconium dichloride, and the mixture was heated at 30° C. Into the autoclave was introduced propylene at a pressure of 0.3 Mpa and polymerization was carried out for 1 hour. After the polymerization was completed, polymer was filtered and the catalyst component was decomposed with 1 liter of methanolic hydrochloric acid. Subsequently, filtration, washing and drying were carried out to obtain 5.1 g of a propylene homopolymer. The polymerization activity was 36 kg-polymer/mmol (Zr).hr. The obtained propylene homopolymer was analyzed and the results were as follows: MFR=0.004 g/10 min.; Mw=1.3×10$^6$ g/mol; Mw/Mn=2.64; and mp 157.0° C.

Example 2

Production of Propylene Homopolymer Using Dimethylsilylene(2-methyl-4-phenyl-indenyl)(2-(2-(5-methyl)-furyl)-4-phenyl-indenyl)zirconium Dichloride as a Catalytic Component After a SUS autoclave was charged with a toluene solution of methylaluminoxane (MMAO3A, manufactured by Tosoh-Akzo Co., Ltd.) in an amount of 4.7×10$^{-3}$ mol (in terms of Al atom), 1 liter of liquefied propylene was added and the temperature was raised to 50° C. Separately, dimethylsilylene(2-methyl-4-phenyl-indenyl)(2-(2-(5-methyl)-furyl)-4-phenyl-indenyl)zirconium dichloride (0.13×10$^{-6}$ mol) was allowed to react with a toluene solution of methylaluminoxane (MMAO3A, manufactured by Tosoh-Akzo Co. Ltd.) in an amount of 3.1×10$^{-3}$ mol (in terms of Al) for 15 minutes. This reaction solution was introduced to the autoclave under pressure to initiate polymerization and propylene homopolymer polymerization was carried out at 50° C. for 20 minutes. The termination of polymerization was conducted by the addition of a small amount of methanol. Subsequently, demineralization with a strong alkaline solution and drying were carried out to produce 21.7 g of a propylene copolymer. The polymerization activity was 538 kg-polymer/mmol (Zr).hr. The obtained propylene homopolymer was analyzed and the results were as follows: m p 159.3° C.; Mw=3.4×10$^6$ g/mol; Mw/Mn=2.8; intrinsic viscosity [η]=9.66 dl/g.

Comparative Example 2

Production of Propylene Homopolymer Using Racemic Dimethylsilylenebis(2-methyl-4-phenyl-indenyl)zirconium Dichloride as a Catalytic Component After a SUS autoclave was charged with a toluene solution of methylaluminoxane (MMAO3A, manufactured by Tosoh-Akzo Co., Ltd.) in an amount of 2.25×10$^{-3}$ mol (in terms of Al atom), 1 liter of liquefied propylene was added and the temperature was raised to 50° C. Separately, racemic dimethylsilylenebis(2-methyl-4-phenyl-indenyl)zirconium dichloride (0.25×10$^{-6}$ mol) prepared according to the method described in Example 1 of JP-A-10-226712 was allowed to react with a toluene solution of methylaluminoxane (MMA03A, manufactured by Tosoh-Akzo Co., Ltd.) in an amount of 1.5×10$^{-3}$ mol (in terms of Al) for 15 minutes. This reaction solution was then introduced to the autoclave under pressure to initiate polymerization and propylene homopolymerization was carried out at 50° C. for 20 minutes. The termination of polymerization was conducted by the addition of a small amount of methanol. Subsequently, demineralization with a strong alkaline solution and drying were carried out to produce 22.7 g of a propylene copolymer.

The polymerization activity was 272 kg-polymer/mmol (Zr).10 hr. The obtained propylene homopolymer was analyzed and the results were as follows: mp 157.6° C.; Mw=3.10×10$^6$ g/mol; Mw/Mn=2.6.

Example 3

Production of Propylene/1-butene Copolymer Using Dimethylsilylene(2-methyl-4-phenyl-indenyl)(2-(2-(5-methyl)-furyl)-4-phenyl-indenyl)zirconium Dichloride as a Catalytic Component A 1.5–1 SUS autoclave sufficiently purged with nitrogen was charged with 675 ml of hexane and 45 g of 1-butene, to which was added triisobutylaluminum (0.75 mmol). After the internal temperature was raised to 70° C., the autoclave was supplied with propylene to render the total pressure to 0.7 Mpa, and methylaluminoxane (PMAO, manufactured by Tosoh-Akzo Co., Ltd.)(0.225 mmol) and 25 dimethylsilylene(2-methyl-4-phenyl-indenyl)(2-(2-(5-methyl)-furyl)-4-phenyl-indenyl)zirconium dichloride (0.75×10$^{-6}$ mol) prepared according to Example 1 were added. Propylene was continuously fed so as to maintain a total pressure of 0.7 Mpa and polymerization was carried out for 30 minutes. After polymerization, the autoclave was degassed, from which a polymer was recovered in a large amount of methanol. The polymer was dried under reduced pressure at 110° C. for 12 hours.

The obtained polymer was 35 g and its polymerization activity was 93 kg-polymer/mmol (Zr).hr. The content of 1-butene was 26.5 mol %, Mw was 2.4×10$^5$ g/mol, the intrinsic viscosity [η]was 1.8 dl/g, and the melting point was 87° C.

Example 4

Preparation of Dimethylsilylene(2-methyl-4-phenyl-indenyl)(2-(2-(5-methyl)-furyl)-4-phenyl-indenyl) zirconium Dichloride as Supported Catalyst A glass reactor having an internal volume of 500 ml and sufficiently purged with nitrogen and equipped with a stirrer was charged with 30 ml of a toluene solution of methylaluminoxane (concentration: 2.8 mol/liter, manufactured by Albemarle Corporation) in an amount of 84 mmol (in terms of Al atom) and 150 mg (0.216 mmol) of dimethylsilylene (2-methyl-4-phenyl-indenyl)(2-(2-(5-methyl)-furyl)-4-phenyl-indenyl)zirconium dichloride prepared according to Example 1 as a metallocene compound. The reactor was maintained at 25° C. for 15 minutes at stirring to allow for reaction and a reaction product of the metallocene compound and aluminoxane was obtained.

Subsequently, to the reactor was added 5 g of silica (MD747JR, manufactured by Crossfield Chemicals) having an average particle diameter of 20 μm which had been fired at 500° C. for 8 hours under reduced pressure. The temperature of the reactor was raised to 110° C. and maintained for 120 minutes at stirring. Contact reaction between the reaction product obtained above and silica was carried out to produce slurry containing a crude supported metallocene catalyst.

Subsequently, the reactor was cooled to –10° C. and to this was added 250 ml of n-hexane while the temperature was maintained at –10° C. and stirring continued for 10 minutes. The stirrer was then stopped and solvent was separated by decantation. Without interruption, while the temperature of the reactor was maintained at –10° C., 250 ml of n-hexane was poured into the reactor and stirring and washing was continued for 5 minutes. The stirrer was then stopped and a washing operation for separating the solvent for washing through decantation was repeated four times. Subsequently, filtration and drying gave the supported metallocene catalyst.

Polymerization of Propylene Using Dimethylsilylene(2-methyl-4-phenyl-indenyl)(2-(2-(5-methyl)-furyl)-4-phenyl-indenyl)zirconium Dichloride as a Supported Catalyst After a reactor having an internal volume of 1.8 l and sufficiently purged with nitrogen was charged with triethylamluminium (1.0 mmol) and 0.7 l of liquefied propylene, the internal temperature was raised to 70° C. and stabilized. Subsequently, 25 mg of the supported metallocene catalyst prepared above accompanied by 0.3 l of liquefied propylene was fed into the reactor instantaneously to initiate polymerization. Propylene homopolymerization was carried out at 70° C. for 60 minutes. Consequently, 250 g of a propylene polymer was obtained and the polymerization activity was 10,000 g-polymer/g-catalyst.hr per g of the supported metallocene catalyst. The obtained propylene polymer was analyzed: MFR=0.19 g/10 min; mp 155° C.; the bulk specific gravity of powder (BD)=500 kg/m$^3$.

Example 5

Copolymerization of Propylene/ethylene Using Dimethylsilylene(2-methyl-4-phenyl-indenyl)(2-(2-(5-methyl)-furyl)-4-phenyl-indenyl)zirconium Dichloride as a Supported Catalyst After a reactor having a internal volume of 1.8 l and sufficiently purged with nitrogen was charged with triethylamluminium (1.0 mmol) and 1 liter of liquefied propylene, the internal temperature was raised to 60° C. and stabilized. Subsequently, ethylene was fed until such time that the internal pressure (gage pressure) of the reactor increased 0.3 Mpa compared to the pressure prior to the charging and the internal temperature of the reactor was raised to 70° C. and stabilized. The supported metallocene catalyst prepared in Example 4 (11.8 mg) was then fed into the reactor to initiate polymerization. Copolymerization of propylene and ethylene was carried out at 70° C. for 30 minutes. Consequently, 88.5 g of a propylene/ethylene copolymer was obtained and its polymerization activity was 15,000 g-polymer/g-catalyst.hr. The obtained propylene/ethylene copolymer was analyzed: MFR=0.06 g/10 min.: the content of ethylene unit=4 wt %; mp 125° C.; and the bulk specific gravity of powder (BD)=450 kg/m$^3$.

Between Example 4 and Example 5, propylene homopolymerization and propylene/ethylene copolymerization were compared under the same conditions where hydrogen was not present. From these results it was understood that even where ethylene monomer was fed in a substantial amount during polymerization, MRF characteristically did not raise, but lowered. This clearly suggests that the ethylene feed has improved the molecular weight of the polymer.

A comparison of Examples 4 and 5 demonstrates that the introduction of 4 wt % ethylene has lowered the melting point as much as 30° C. in the use of the catalyst of this invention and that the catalyst has an excellent characteristic feature in this melting point lowering effect.

Example 6

Copolymerization of Propylene/Ethylene Using Dimethylsilylene(2-methyl-4-phenyl-indenyl)(2-(2-(5-methyl)-furyl)-4-phenyl-indenyl)zirconium Dichloride as a Supported Catalyst After a reactor having a internal volume of 1.8 l and sufficiently purged with nitrogen was charged with triethylamluminium (1.0 mmol), hydrogen (4.4 mmol) and 1 liter of liquefied propylene, the internal temperature was raised to 60° C. and stabilized. Subsequently, ethylene was fed until such time that the internal pressure (gage pressure) of the reactor increased 0.3 Mpa compared to the pressure prior to the charging. The supported metallocene catalyst prepared in Example 4 (17.9 mg) was then fed into the reactor to initiate polymerization. Copolymerization of propylene and ethylene was carried out at 60° C. for 30 minutes. Consequently, 242 g of a propylene/ethylene copolymer was obtained and its polymerization activity was 27,000 g-polymer/g-catalyst.hr. The obtained propylene/ethylene copolymer was analyzed: MFR=9.4 g/10 min; the content of ethylene unit=4 wt % (5.9 mol %); and the bulk specific gravity of powder (BD)-450 kg/m$^3$.

Example 7

Synthesis of Dimethylsilylene(2-methyl-4-phenyl-indenyl)(2-phenyl-4-phenyl-indenyl)zirconium Dichloride (1) Synthesis of Dimethyl(2-methyl-4-phenyl-indenyl)(2-phenyl-4-phenyl-indenyl)silane A 500 ml glass reaction vessel was charged with 11.1 g (54 mmol) of 2-methyl-4-phenylindene and 100 ml of THF and cooled to −70° C. on a dry ice/methanol bath. To the mixture was added dropwise 35 ml (55 mmol) of a n-butyllithium/hexane solution (1.56 mol/l). After addition was completed, the mixture was stirred overnight while it was gradually brought to room temperature, and thus a lithium solution of 2-methyl-4-phenylindene was prepared.

A separate 500 ml glass reaction vessel was charged with 14 ml (115 mmol) of dimethyldichlorosilane and 100 ml of THF and cooled to −70° C. on a dry ice/methanol bath. To the mixture was added dropwise the lithium solution of 2-methyl-4-phenylindene slowly. After addition was completed, the mixture was stirred at room temperature overnight while it was gradually brought to room temperature. The solvent and excessive dimethyldichlorosilane was then distilled off under reduced pressure. To this was added 100 ml of THF and thus a chlorosilane solution was prepared.

A different 500 ml glass reaction vessel was charged with 14.5 g (56.9 mmol) of 2,4-diphenylindene and 100 ml of THF and cooled to −70° C. on a dry ice/methanol bath. To the mixture was added dropwise 35 ml (55 mmol) of a n-butyllithium/hexane solution (1.56 mol/l). After addition was completed, the mixture was stirred for 4 hours. while it was gradually brought to room temperature. The mixture was again cooled to −70° C. on a dry ice/methanol bath and after addition of 0.23 ml (2.9 mmol) of 1-methylimidazole, the chlorosilane solution prepared previously was added dropwise. After addition was completed, the mixture was stirred overnight while it was gradually brought to room temperature.

To the reaction solution was added distilled water and it was transferred to a separatory funnel and washed with brine until it turned neutral. Anhydrous sodium sulfate was added and the solution was dried overnight. The anhydrous sodium sulfate was filtered off and the solvent was distilled off under reduced pressure. Purification on a silica gel column gave 24 g (82% yield) of dimethyl(2-methyl-4-phenyl-indenyl)(2-phenyl-4-phenyl-indenyl)silane as a light yellow solid.

(2) Synthesis of Dimethylsilylene(2-methyl-4-phenylindenyl)(2-phenyl-4-phenyl-indenyl)zirconium Dichloride A 500 ml glass reaction vessel was charged with 12.6 g (24 mmol) of dimethyl(2-methyl-4-phenyl-indenyl)(2-phenyl-4-phenyl-indenyl)silane and 200 ml of diethyl ether and cooled to −70° C. on a dry ice/methanol bath. To the mixture was added dropwise 31 ml (48 mmol) of a n-butyllithium/ hexane solution (1.56 mol/l). After addition was completed, the mixture was stirred overnight while it was gradually brought to room temperature. The solvent of the reaction solution was concentrated to about 20 ml under reduced pressure and, upon addition of 400 ml of toluene, the reaction solution was cooled to −70° C. on a dry ice/methanol bath. To this was added 5.6 g (24 mmol) of tetrachlorozirconium. Subsequently, the mixture was stirred overnight while it was gradually brought to room temperature. The solvent was distilled off under reduced pressure and recrystallization from toluene/hexane gave 2.3 g (14% yield) of dimethylsilylene(2-methyl-4-phenyl-indenyl)(2-phenyl-4-phenyl-indenyl)zirconium dichloride in a racemic-like form (purity of 99% or more) as an orange crystal.

$^1$H-NMR data (CDCl$_3$) of the racemic-like form: δ0.98 (s, 3H), δ1.38 (s, 3H), δ2.29 (s, 3H), δ6.40 (d, 1H), δ6.67 (dd, 1H), δ6.94 (s, 1H), δ7.04 (s, 1H), δ7.15–7.18 (m, 2H), δ7.24–7.27 (m, 1H), δ7.30–7.43 (m, 11H), δ7.62 (dd, 2H), δ7.67 (dd, 2H), δ7.79 (d, 1H).

Preparation of Dimethylsilylene(2-methyl-4-phenyl-indenyl)(2-phenyl-4-phenyl-indenyl)zirconium Dichloride as Supported Catalyst A glass reactor having an internal volume of 500 ml and sufficiently purged with nitrogen and equipped with a stirrer was charged with 30 ml of a toluene solution of methylaluminoxane (concentration: 2.8 mol/liter, manufactured by Albemarle Corporation) in an amount of 84 mmol (in terms of Al atom) and 168 mg (0.243 mmol) of dimethylsilylene (2-methyl-4-phenyl-indenyl)(2-phenyl-4-phenyl-indenyl) zirconium dichloride prepared as described above as a metallocene compound. The reactor was maintained at 25° C. for 15 minutes at stirring to allow for reaction and a reaction product of the metallocene compound and aluminoxane was obtained.

Subsequently, to the reactor was added 5 g of silica (MD747JR, manufactured by Crossfield Chemicals) having an average particle diameter of 20 μm which had been fired at 500° C. for 8 hours under reduced pressure. The temperature of the reactor was raised to 110° C. and maintained for 120 minutes at stirring. Contact reaction between the reaction product obtained above and silica was thus carried out to produce slurry containing a crude supported metallocene catalyst.

Subsequently, the reactor was cooled to −10° C. and to this was added 250 ml of n-hexane while the temperature was maintained at −10° C. and stirring continued for 10 minutes. The stirrer was then stopped and solvent was separated by decantation. Without interruption, while the temperature of the reactor was maintained at −10° C., 250 ml of n-hexane was poured into the reactor and stirring and washing continued for 5 minutes. The stirrer was then stopped and a washing operation for separating the wash solvent through decantation was repeated four times. Subsequently, filtration and drying gave the supported metallocene catalyst.

Polymerization of Propylene Using Dimethylsilylene(2-methyl-4-phenyl-indenyl)(2-phenyl-4-phenyl-indenyl)zirconium Dichloride as a Supported Catalyst After a reactor having a internal volume of 1.8 l and sufficiently purged with nitrogen was charged with triethylamluminium (1.0 mmol) and 0.7 l of liquefied propylene, the internal temperature was raised to 70° C. and stabilized. Subsequently, 40.1 mg of the supported metallocene catalyst prepared above accompanied by 0.3 l of liquefied propylene was fed into the reactor instantaneously to initiate polymerization. Propylene homopolymerization was carried out at 70° C. for 60 minutes. Consequently, 86.5 g of a propylene polymer was obtained and its polymerization activity was 2,160 g-polymer/g-catalyst-hr per g of the supported metallocene catalyst. The obtained propylene polymer was analyzed: MFR=0.23 g/10 min; and the bulk specific gravity of powder (BD)=480 kg/m$^3$.

Example 8

Copolymerization of Propylene/Ethylene Using Dimethylsilylene(2-methyl-4-phenyl-indenyl)(2-phenyl-4-phenyl-indenyl)zirconium Dichloride as a Supported Catalyst After a reactor having a internal volume of 1.8 l and sufficiently purged with nitrogen was charged with triethylamluminium (1.0 mmol) and one liter of liquefied propylene, the internal temperature was raised to 60° C. and stabilized. Subsequently, ethylene was fed until such time that the internal pressure (gage pressure) of the reactor increased 0.3 Mpa compared to the pressure prior to the charging and stabilized, after which the internal temperature of the reactor was raised to 70° C. and stabilized. The supported metallocene catalyst prepared in Example 7 (39.9 mg) was then fed into the reactor to initiate polymerization. Copolymerization of propylene and ethylene was carried out at 70° C. for 30 minutes. Consequently, 117.5 g of a propylene/ethylene copolymer was obtained and its polymerization activity was 5,890 g-polymer/g-catalyst.hr. The obtained propylene/ethylene copolymer was analyzed: MFR=0.08 g/10 min; the content of ethylene unit=3 wt %; and the bulk specific gravity of powder (BD)=460 kg/m$^3$.

Between Example 7 and Example 8, propylene homopolymerization and propylene/ethylene copolymerization were compared under the same conditions where hydrogen was not present. From these results it was understood that even where ethylene monomer was fed in a substantial amount during polymerization, MFR characteristically did not raise, but lowered. This clearly suggests that the ethylene feed has improved the molecular weight of the polymer.

Comparative Example 3

Preparation of Dimethylsilylene(2-methyl-4-phenyl-indenyl)(2-isopropyl-4-phenyl-indenyl)zirconium Dichloride as Supported Catalyst A glass reactor having an internal volume of 500 ml and sufficiently purged with nitrogen and equipped with a stirrer was charged with 30 ml of a toluene solution of methylaluminoxane (concentration: 2.8 mol/liter, manufactured by Albemarle Corporation) in an amount of 84 mmol (in terms of Al atom) and 150 mg (0.229 mmol) of dimethylsilylene (2-methyl-4-phenyl-indenyl)(2-isopropyl-4-phenyl-indenyl) zirconium dichloride prepared according to the method as described in WO97/40075 as a metallocene compound. The reactor was maintained at 25° C. for 15 minutes at stirring to allow for reaction and a reaction product of the metallocene compound and aluminoxane was obtained.

Subsequently, to the reactor was added 5 g of silica (MD747JR, manufactured by Crossfield Chemicals) having an average particle diameter of 20 μm which had been fired at 500° C. for 8 hours under reduced pressure. The temperature of the reactor was raised to 110° C. and maintained for 120 minutes at stirring. Contact reaction between the reaction product obtained above and silica was thus carried out to produce slurry containing a crude supported metallocene catalyst on which the reaction product was deposited.

Subsequently, the reactor was cooled to −10° C. and to this was added 250 ml of n-hexane while the temperature was maintained at −10° C. and stirring continued for 10 minutes. The stirrer was then stopped and solvent was separated by decantation. Without interruption, while the temperature of the reactor was maintained at −10° C., 250 ml of n-hexane was poured into the reactor and stirring and washing continued for 5 minutes. The stirrer was then stopped and a washing operation for separating the wash solvent through decantation was repeated four times. Subsequently, filtration and drying gave the supported metallocene catalyst.

Polymerization of Propylene Using Dimethylsilylene(2-methyl-4-phenyl-indenyl)(2-isopropyl-4-phenyl-indenyl)zirconium Dichloride as a Supported Catalyst After a reactor having a internal volume of 1.8 l and sufficiently purged with nitrogen was charged with triethylamluminium (1.0 mmol) and 0.7 l of liquefied propylene, the internal temperature was raised to 70° C. and stabilized. Subsequently, 26 mg of the supported metallocene catalyst prepared above accompanied by 0.3 l of liquefied propylene was fed into the reactor instantaneously to initiate polymerization. Propylene homopolymerization was carried out at 70° C. for 60 minutes. Consequently, 210 g of a propylene polymer was obtained and its polymerization activity was 8,080 g-polymer/g-catalyst-hr per g of the supported metallocene catalyst. The obtained propylene polymer was analyzed: MFR=0.3 g/10 min; mp 152° C.; and the bulk specific gravity of powder (BD)=450 kg/m$^3$.

When these results are compared with those of Example 4, it is obvious that the catalyst of this invention described in Example 4 produces a propylene homopolymer having a lower MFR (i.e., higher molecular weight) and a higher melting point with a higher polymerization activity.

Comparative Example 4

Copolymerization of Propylene/Ethylene Using Dimethylsilylene(2-methyl-4-phenyl-indenyl)(2-isopropyl-4-phenyl-indenyl)zirconium Dichloride as a Supported Catalyst After a reactor having a internal volume of 1.8 l and sufficiently purged with nitrogen was charged with triethylamluminium (1.0 mmol) and one liter of liquefied propylene, the internal temperature was raised to 60° C. and stabilized. Subsequently, ethylene was fed until such time that the internal pressure (gage pressure) of the reactor increased 0.3 Mpa compared to the pressure prior to the charging and stabilized, after which the internal temperature of the reactor was raised to 70° C. and stabilized. The supported metallocene catalyst prepared in Comparative Example 3 (12.0 mg) was then fed into the reactor to initiate polymerization. Copolymerization of propylene and ethylene was carried out at 70° C. for 30 minutes. Consequently, 69.0 g of a propylene/ethylene copolymer was obtained and its polymerization activity was 11,500 g-polymer/g-catalyst-hr. The obtained propylene/ethylene copolymer was analyzed: MFR=2.6 g/10 min; the content of ethylene unit=3.5 wt %; the bulk specific gravity of powder (BD)=430 kg/m$^3$; and mp 138° C.

Between Comparative Example 3 and Comparative Example 4, propylene homopolymerization and propylene/ethylene copolymerization were compared under the same conditions where hydrogen was not present. The propylene/ethylene copolymer produced in Comparative Example 4 displays a far higher MRF than does the propylene homopolymer produced in Comparative Example 3.

Comparative Example 5

Preparation of Dimethylsilylene(2-methyl-4-(p-t-butylphenyl)-indenyl)(2-isopropyl-4-(p-t-butylphenyl)-indenyl)zirconium Dichloride as Supported Catalyst A glass reactor having an internal volume of 500 ml and sufficiently purged with nitrogen and equipped with a stirrer was charged with 30 ml of a toluene solution of methylaluminoxane (concentration: 2.8 mol/liter, manufactured by Albemarle Corporation) in an amount of 84 mmol (in terms of Al atom) and 150 mg (0.195 mmol) of dimethylsilylene (2-methyl-4-(p-t-butylphenyl)-indenyl)(2-isopropyl-4-(p-t-butylphenyl)-indenyl)zirconium dichloride prepared according to the method as described in WO01/48034 as a metallocene compound. The reactor was maintained at 25° C. for 15 minutes at stirring to allow for reaction and a reaction product of the metallocene compound and aluminoxane was obtained.

Subsequently, to the reactor was added 5 g of silica (MD747JR, manufactured by Crossfield Chemicals) having an average particle diameter of 20 µm which had been fired at 500° C. for 8 hours under reduced pressure. The temperature of the reactor was raised to 110° C. and maintained for 120 minutes at stirring. Contact reaction between the reaction product obtained above and silica was thus carried out to produce slurry containing a crude supported metallocene catalyst on which the reaction product was deposited.

Subsequently, the reactor was cooled to −10° C. and to this was added 250 ml of n-hexane while the temperature was maintained at −10° C. and stirring continued for 10 minutes. The stirrer was then stopped and solvent was separated by decantation. Without interruption, while the temperature of the reactor was maintained at −10° C., 250 ml of n-hexane was poured into the reactor and stirring and washing continued for 5 minutes. The stirrer was then stopped and a washing operation for separating the wash solvent through decantation was repeated four times. Subsequently, filtration and drying gave the supported metallocene catalyst.

Polymerization of Propylene Using Dimethylsilylene(2-methyl-4-(p-t-butylphenyl)-indenyl)(2-isopropyl-4-(p-t-butylphenyl)-indenyl)zirconium Dichloride as a Supported Catalyst After a reactor having a internal volume of 1.8 l and sufficiently purged with nitrogen was charged with triethylamluminium (1.0 mmol) and 0.7 l of liquefied propylene, the internal temperature was raised to 70° C. and stabilized. Subsequently, 27 mg of the supported metallocene catalyst prepared above accompanied by 0.3 l of liquefied propylene was fed into the reactor instantaneously to initiate polymerization. Propylene homopolymerization was carried out at 70° C. for 60 minutes. Consequently, 220 g of a propylene polymer was obtained and its polymerization activity was 8,150 g-polymer/g-catalyst-hr per g of the supported metallocene catalyst. The obtained propylene polymer was analyzed: the melting point=159° C., and the bulk specific gravity of powder (BD)=480 kg/m$^3$.

Copolymerization of Propylene/Ethylene Using Dimethylsilylene(2-methyl-4-(p-t-butylphenyl)-indenyl)(2-isopropyl-4-(p-t-butylphenyl)-indenyl)zirconium Dichloride as a Supported Catalyst After a reactor having a internal volume of 1.8 l and sufficiently purged with nitrogen was charged with triethylamluminium (1.0 mmol) and one liter of liquefied propylene, the internal temperature was raised to 60° C. and stabilized. Subsequently, ethylene was fed until such time that the internal pressure (gage pressure) of the reactor increased 0.3 Mpa compared to the pressure prior to the charging and stabilized, after which the internal temperature of the reactor was raised to 70° C. and stabilized. The supported metallocene catalyst prepared above (12.1 mg) was then fed into the reactor to initiate polymerization. Copolymerization of propylene and ethylene was carried out at 70° C. for 30 minutes. Consequently, 75.0 g of a propylene/ethylene copolymer was obtained and its polymerization activity was 12,400 g-polymer/g-catalyst-hr. The obtained propylene/ethylene copolymer was analyzed: the content of ethylene unit=6 wt %; mp 140° C.; and the bulk specific gravity of powder (BD)=430 kg/m$^3$.

From the results it is understood that the catalyst described above requires an extremely large amount of ethylene to lower the melting point from 159° c to 140° C. The copolymer displays a far higher MFR than does the propylene homopolymer produced in Comparative Example 3.

Example 9

Synthesis of Dimethylsilylene(2-methyl-4-(1-naphtyl)-indenyl)(2-(2-(5-methylfuryl)-4-(1-naphtyl)-indenyl)zirconium Dichloride (1) Synthesis of 4-(1-naphtyl)indene To one liter egg-plant type flask were added 55 g (0.27 mmol) of 1-bromonaphthalene and 300 ml of diethyl ether. The mixture was cooled to −70° C. on a dry ice/methanol bath, to which 170 ml (0.27 mmol) of a n-butyllithium/hexane solution (1.56 mol/l) was added dropwise. After addition was completed, the mixture was stirred for 6 hours while it was gradually brought to room temperature. The mixture was further cooled to −40° C. and to this were added dropwise 70 ml (0.30 mmol) of triisopropylborate and 100 ml of diethyl ether, and stirred overnight. To the reaction solution was added 200 ml of 2 N hydrochloric acid to cause hydrolysis. Diethyl ether (200 ml) was added to the reaction solution, which was washed with brine until it turned neutral. After drying over anhydrous sulfate, the solvent was distilled off under reduced pressure to give light yellow crystals of naphthyl boric acid.

Naphthyl boric acid was dissolved in 500 ml of dioxane in a one liter egg-plant type flask. To this were added 115 g (0.54 mol) of tripotassium phosphate, 20 g (0.13 mol) of 4-chloroindene, 1.6 g (4.1 mmol) of 2-dimethylamino-2'-dichlorohexylphosphinobiphenyl and 0.7 g (3.1 mmol) of palladium acetate, and the mixture was heated at 80° C. for 7 hours.

The reaction solution was added to one liter of water and was extracted with 500 ml of ether. The ether layer was successively washed with an aqueous ammonium chloride solution and brine. Anhydrous sulfate was added and the solution was dried overnight. Ether was distilled off under reduced pressure. Purification on a silica gel column gave 31.6 g (98% yield) of 4-(1-naphthyl)indene as a light yellow crystal.

(2) Synthesis of 2-bromo-4-(1-naphthyl)indene

A one liter glass reaction vessel was charged with 17 g (70 mmol) of 4-(1-naphthyl)indene, 350 ml of DMSO and 3 ml of water and cooled to 0° C. on a ice bath. To the mixture was added 15 g (84.3 mmol) of N-bromosuccinimide and the mixture was stirred at room temperature for 1 hour. The reaction solution was added to one liter of water and was extracted with 500 ml of ether. The ether layer was washed with brine. Ether was distilled off under reduced pressure. To this were added 700 ml of toluene and 2 g (11 mmol) of p-toluenesulfonic acid and the mixture was heated at reflux while water was removed occasionally. Purification on a silica gel column gave 21. 1 g (94% yield) of 2-bromo-4-(1-naphthyl)indene as a light yellow crystal.

(3) Synthesis of 2-(2-(5-methyl)furyl)-4-(1-naphthyl)indene

To 500 ml egg-plant type flask were added 6.7 g (82 mmol) of 2-methylfuran and 150 ml of DME. The mixture was cooled to −70° C. on a dry ice/methanol bath, to which 53 ml (83 mmol) of a n-butyllithium/hexane solution (1.56 mol/l) was added dropwise. After addition was completed, the mixture was stirred for 6 hours while it was gradually brought to room temperature. The mixture was further cooled to −40° C., and to this were added dropwise 20 ml (87 mmol) of triisopropylborate and 20 ml of DME, and stirred overnight. To the reaction solution was added 150 ml of distilled water to cause hydrolysis. To this were further added 13 g (1.2 mol) of sodium carbonate, 21.1 g (65 mmol) of 2-bromo-4-(1-naphthyl)indene, 200 ml of DME and 5 g (4.3 mmol) of tetrakis(triphenylphosphine)palladium, and the mixture was heated at 80° C. for 2 hours.

After allowing cooling, the reaction solution was added to 500 ml of water and was extracted with 500 ml of ether. The ether layer was successively washed with an aqueous ammonium chloride solution and brine. Anhydrous sulfate was added and the solution was dried overnight. Ether was distilled off under reduced pressure. Purification on a silica gel column gave 19 g (91% yield) of 2-(2-(5-methyl)furyl)-4-(1-naphthyl)indene as a light yellow crystal.

(4) Synthesis of dimethyl(2-methyl-4-(1-naphthyl)indenyl)(2-(2-(5-methylfuryl)-4-(1-naphthyl)indenyl)silane A 500 ml glass reaction vessel was charged with 14.8 g (58 mmol) of 2-methyl-4-(1-naphthyl)indene and 100 ml of THF and cooled to −70° C. on a dry ice/methanol bath. To the mixture was added dropwise 37 ml (59 mmol) of a n-butyllithium/hexane solution (1.58 mol/l). After addition was completed, the mixture was stirred overnight while it was gradually brought to room temperature, and thus a lithium solution of 2-methyl-4-(1-naphthyl)indene was prepared.

A separate 500 ml glass reaction vessel was charged with 17 ml (0.14 mol) of dimethyldichlorosilane and 200 ml of THF, and cooled to −70° C. on a dry ice/methanol bath. To the mixture was added dropwise the lithium solution of 2-methyl-4-(1-naphthyl)indene prepared before slowly. After addition was completed, the mixture was stirred at room temperature for 1 hour and the solvent and excessive dimethyldichlorosilane was distilled off under reduced pressure. To this was added 100 ml of THF and thus a chlorosilane solution was prepared.

A different 500 ml glass reaction vessel was charged with 18.6 g (58 mmol) of 2-(2-(5-methylfuryl))-4-(1-naphthyl) indene and 200 ml of THF, and cooled to −70° C. on a dry ice/methanol bath. To the mixture was added dropwise 37 ml (59 mmol) of a n-butyllithium/hexane solution (1.58 mol/l). After addition was completed, the mixture was stirred for 4 hours while it was gradually brought to room temperature. The mixture was again cooled to −70° C. on a dry ice/methanol bath and after addition of 0.4 ml (5 mmol) of 1-methylimidazole, the chlorosilane solution prepared previously was added dropwise. After addition was completed, the mixture was stirred overnight while it was gradually brought to room temperature.

To the reaction solution was added distilled water and it was transferred to a separatory funnel and washed with brine until it turned neutral. Anhydrous sodium sulfate was added and the solution was dried overnight. The anhydrous sodium sulfate was filtered off and the solvent was distilled off under reduced pressure. Purification on a silica gel column gave 33 g (89% yield) of dimethyl(2-methyl-4-(1-naphthyl)indenyl)(2-(2-(5-methylfuryl)-4-(1-naphthyl)indenyl)silane as a light yellow solid.

(5) Synthesis of dimethylsilylene(2-methyl-4-(1-naphthyl)indenyl)(2-(2'-(5'-methylfuryl))-4-(1-naphthyl)indenyl)zirconium Dichloride A 500 ml glass reaction vessel was charged with 8.1 g (12 mmol) of dimethyl(2-methyl-4-(1-naphthyl)indenyl)(2-(2-(5-methylfuryl))-4-(1-naphthyl)indenyl)silane and 200 ml of diethyl ether and cooled to −70° C. on a dry ice/methanol bath. To the mixture was added dropwise 15 ml (23 mmol) of a n-butyllithium/hexane solution (1.56 mol/l). After addition was completed, the mixture was stirred overnight while it was gradually brought to room temperature. The solvent of the reaction solution was concentrated to about 20 ml under reduced pressure and, upon addition of 400 ml of toluene, the reaction solution was cooled to −70° C. on a dry ice/methanol bath. To this was added 2.7 g (12 mmol) of tetrachlorozirconium. Subsequently, the mixture was stirred overnight while it was gradually brought to room temperature.

The solvent was distilled off under reduced pressure and recrystallization from methylene chloride/hexane gave 5.4 g (55% yield) of dimethylsilylene(2-methyl-4-(1-naphthyl)indenyl)(2-(2-(5-methylfuryl))-4-(1-naphthyl)indenyl)zirconium dichloride (racemic-like form/meso-like form=50/50) as an orange crystal.

$^1$H-NMR data (CDCl$_3$) (racemic-like form/meso-like form=50/50): δ1.10 (s, 3H), δ1.27 (s, 3H), δ1.41 (s, 3H), δ1.59 (s, 3H), δ1.77 (s, 3H), δ2.34 (s, 3H), δ2.45 (s, 3H), δ5.98 (dd, 1H), δ6.03 (dd, 1H), δ6.08 (d, 1H), δ6.34 (s, 1H), δ6.43 (s, 1H), δ6.49 (s, 1H), δ6.51 (d, 1H), δ6.57 (s, 1H), δ7.04–7.89 (m, 40H)

Example 10

Synthesis of Dimethylsilylene(2-methyl-4-phenyl-indenyl)(2-(2-(5-methylthienyl))-4-phenyl-indenyl) zirconium Dichloride (1) Synthesis of 2-(2-(5-methylthienyl)-4-phenylindene To one liter egg-plant type flask were added 23 g (0.23 mmol) of 2-methythiophene and 300 ml of DME. The mixture was cooled to −70° C. on a dry ice/methanol bath, to which 150 ml (0.23 mol) of a n-butyllithium/hexane solution (1.56 mol/l) was added dropwise. After addition was completed, the mixture was stirred for 3 hours while it was gradually brought to room temperature. The mixture was further cooled to −50° C., and to this were added dropwise 54 ml (0.23 mol) of triisopropylborate and 100 ml of DME, and stirred overnight. To the reaction solution was added 250 ml of distilled water to cause hydrolysis. To this were further added 37 g (0.35 mol) of sodium carbonate, 50 g (0.18 mol) of 2-bromo-4-phenylindene and 5 g (4.3 mmol) of tetrakis(triphenylphosphine)palladium, and the mixture was heated at 80° C. for 2 hours.

After allowing cooling, the reaction solution was added to 500 ml of water and was extracted with 500 ml of diethyl ether. The ether layer was washed with brine. Sodium sulfate was added and the solution was dried overnight. After removal of sodium sulfate by filtration, the solvent was distilled off under reduced pressure. Purification on a silica gel column gave 52 g (98% yield) of 2-(2-(5-methylthienyl)-4-phenylindene as a light yellow crystal.

(2) Synthesis of dimethyl(2-methyl-4-phenyl-indenyl)(2-(2-(5-methylthienyl)-4-phenyl-indenyl)silane A 500 ml glass reaction vessel was charged with 17.9 g (87 mmol) of 2-methyl-4-phenylindene and 100 ml of THF and cooled to −70° C. on a dry ice/methanol bath. To the mixture was added dropwise 56 ml (87 mmol) of a n-butyllithium/hexane solution (1.56 mol/l). After addition was completed, the mixture was stirred overnight while it was gradually brought to room temperature, and thus a lithium solution of 2-methyl-4-phenylindene was prepared.

A separate 500 ml glass reaction vessel was charged with 25 ml (0.20 mol) of dimethyldichlorosilane and 100 ml of THF, and cooled to −70° C. on a dry ice/methanol bath. To the mixture was added dropwise the lithium solution of 2-methyl-4-phenylindene prepared before slowly. After addition was completed, the mixture was stirred at room temperature for 1 hour and the solvent and excessive dimethyldichlorosilane was distilled off under reduced pressure. To this was added 100 ml of THF and thus a chlorosilane solution was prepared.

A different 500 ml glass reaction vessel was charged with 25.0 g (87 mmol) of 2-(2-(5-methylthienyl))-4-phenylindene and 150 ml of THF, and cooled to −70° C. on a dry ice/methanol bath. To the mixture was added dropwise 56 ml (87 mmol) of a n-butyllithium/hexane solution (1.56 mol/l). After addition was completed, the mixture was stirred for 4 hours while it was gradually brought to room temperature. The mixture was again cooled to −70° C. on a dry ice/methanol bath and after addition of 0.4 ml (5 mmol) of 1-methylimidazole, the chlorosilane solution prepared previously was added dropwise. After addition was completed, the mixture was stirred overnight while it was gradually brought to room temperature.

To the reaction solution was added distilled water and it was transferred to a separatory funnel and washed with brine until it turned neutral. Anhydrous sodium sulfate was added and the solution was dried overnight. The anhydrous sodium sulfate was filtered off and the solvent was distilled off under reduced pressure. Purification on a silica gel column gave 36 g (84% yield) of dimethyl(2-methyl-4-phenyl-indenyl)(2-(2-(5-methylthienyl))-4-phenyl-indenyl)silane as a light yellow solid.

(3) Synthesis of Dimethylsilylene(2-methyl-4-phenyl-indenyl)(2-(2-(5-methylthienyl))-4-phenyl-indenyl)zirconium Dichloride A 500 ml glass reaction vessel was charged with 15.6 g (32 mmol) of dimethyl(2-methyl-4-phenyl-indenyl)(2-(2'-(5'-methylthienyl))-4-phenyl-indenyl)silane and 300 ml of diethyl ether and cooled to −70° C. on a dry ice/methanol bath. To the mixture was added dropwise 40 ml (63 mmol) of a n-butyllithium/hexane solution (1.58 mol/l). After addition was completed, the mixture was stirred overnight while it was gradually brought to room temperature. The solvent of the reaction solution was concentrated to about 20 ml under reduced pressure and, upon addition of 400 ml of toluene, the reaction solution was cooled to −70° C. on a dry ice/methanol bath. To this was added 7.3 g (32 mmol) of tetrachlorozirconium. Subsequently, the mixture was stirred overnight while it was gradually brought to room temperature.

The solvent was distilled off under reduced pressure and recrystallization from dichloromethane/hexane gave 1.8 g (8% yield) of dimethylsilylene(2-methyl-4-phenyl-indenyl)(2-(2-(5-methylthienyl))-4-phenyl-indenyl)zirconium dichloride in a racemic-like form (purity of 99%) as an orange crystal.

$^1$H-NMR data (CDCl$_3$) (racemic-like form): δ1.15 (s, 3H), δ1.38 (s, 3H), δ2.28 (s, 3H), δ2.49 (s, 3H), δ6.64 (dd, 1H), δ6.80–6.82 (m, 2H), δ6.81 (s, 1H), δ6.95 (d, 1H), δ7.15 (dd, 1H), δ7.31–7.36 (m, 3H), δ7.38–7.45 (m, 5H), δ7.38–7.45 (m, 5H), δ7.60–7.65 (m, 4H), δ7.76 (d, 1H).

What is claimed is:

1. A metallocene compound represented by the following general formula (1):

wherein

M represents a titanium atom, a zirconium atom or a hafnium atom;

Y represents a linking group bridging K and L and is a methylene group, an ethylene group, a tetraalkylethylene group having alkyl of 1–6 carbon atoms, a dialkylmethylene group having alkyl of 1–6 carbon atoms, a divalent linking group containing within a backbone thereof, an aryl group of 6–16 carbon atoms or a halogenated aryl group of 6–16 carbon atoms, or a divalent linking group containing a silicon atom, a germanium atom, an oxygen atom, a nitrogen atom, a phosphorous atom or a boron atom, or alternatively, Y represents a divalent linking group formed by connecting in series at least two linking groups selected from the foregoing linking groups;

q is an integer representing the number of Y and is 1;

K and L each represent an indenyl group, wherein at least one hydrogen atom of the hydrogen atoms possessed by K or by L is each independently replaced by an alkyl group of 1–10 carbon atoms, a halogen-containing alkyl group of 1–10 carbon atoms, a silicon-containing alkyl group of 1–10 carbon atoms, an aryl group of 6–16 carbon atoms, a halogen-containing aryl group of 6–16 carbon atoms, an alkenyl group of 2–10 carbon atoms, an arylalkyl group of 7–40 carbon atoms, an alkylaryl group of 7–40 carbon atoms, an alicyclic hydrocarbon group of 3–16 carbon atoms, a siloxyl group, an alkoxyl group, a halogen atom, an amino group, a dialkyl-substituted amino group, a SR$^a$ group (S represents a sulfur atom and R$^a$ represents a halogen atom, an alkyl group of 1–10 carbon atoms or an aryl group of 6–16 carbon atoms), or a PR$^b_2$ group (P represents a phosphorous atom; and two R$^b$s may be the same or different and each represents a halogen atom, an alkyl group of 1–10 carbon atoms or an aryl group of 6–16 carbon atoms), with the proviso that at least the substituents at the 2-positions of K and L differ from each other; and the difference between the numbers of carbon atoms in the two substituents is in the range of from 3 to 10; and two Xs may be the same or different and each represents a halogen atom, an alkyl group of 1–6 carbon atoms, an aryl group of 6–16 carbon atoms, an alkylaryl group having alkyl of 1–6 carbon atoms and aryl of 6–16 carbon atoms, or an arylalkyl group having aryl of 6–16 carbon atoms and alkyl of 1–6 carbon atoms, which atom or group is bonded to M.

2. The metallocene compound according to claim 1, wherein at least one of said substituents at the 2-positions of K and L is an aryl group of 6–16 carbon atoms, a halogen-containing aryl group of 6–16 carbon atoms, an alkylaryl group of 7–40 carbon atoms, or an alicyclic hydrocarbon group of 3–16 carbon atoms.

* * * * *